(12) United States Patent
Kim et al.

(10) Patent No.: US 8,957,407 B2
(45) Date of Patent: Feb. 17, 2015

(54) ANTHRACENE DERIVATIVES, PREPARATION METHOD THEREOF AND ORGANIC LIGHT EMITTING DIODE USING THE SAME

(75) Inventors: Kong-Kyeom Kim, Daejeon (KR); Hye-Young Jang, Daejeon (KR); Jae-Chol Lee, Daejeon (KR); Jae-Soon Bae, Daejeon (KR); Dong-Seob Jeong, Seoul (KR); Tae-Yoon Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 930 days.

(21) Appl. No.: 12/223,154

(22) PCT Filed: Jan. 25, 2007

(86) PCT No.: PCT/KR2007/000442
§ 371 (c)(1),
(2), (4) Date: Jul. 23, 2008

(87) PCT Pub. No.: WO2007/086695
PCT Pub. Date: Aug. 2, 2007

(65) Prior Publication Data
US 2010/0252817 A1    Oct. 7, 2010

(30) Foreign Application Priority Data
Jan. 27, 2006    (KR) .................. 10-2006-0009154

(51) Int. Cl.
*H01L 51/54*    (2006.01)
*C07C 211/57*    (2006.01)
(Continued)

(52) U.S. Cl.
CPC ............ *H01L 51/0058* (2013.01); *C07C 15/20* (2013.01); *C07C 15/52* (2013.01);
(Continued)

(58) Field of Classification Search
CPC ............ H01L 51/0052; H01L 51/0054; H01L 51/0055; H01L 51/0056; H01L 51/0058
USPC ............................................................. 257/40
See application file for complete search history.

(56) References Cited

U.S. PATENT DOCUMENTS 5,635,308 A * 6/1997 Inoue et al. .................. 428/696
5,935,721 A * 8/1999 Shi et al. ...................... 428/690
(Continued)

FOREIGN PATENT DOCUMENTS

EP    0 681 019 A2    11/1995
EP    1 491 610 A2    12/2004
(Continued)

*Primary Examiner* — Shaun Campbell
*Assistant Examiner* — Raj R Gupta
(74) *Attorney, Agent, or Firm* — McKenna, Long & Aldridge LLP

(57) ABSTRACT

The present invention provides a novel anthracene derivative, a method for preparing the same, and an organic electronic device using the same. The anthracene derivative according to the invention can function alone as a light emitting host, in particular, as a blue host in an organic electronic device. Further, the anthracene derivative according to the invention can also function as a hole injecting or hole transporting material, an electron injecting or electron transporting material, or a light emitting material in an organic electronic device including a light emitting device. Therefore, the organic electronic device according to the present invention shows excellent characteristics in efficiency, drive voltage and stability.

9 Claims, 1 Drawing Sheet

(51) Int. Cl.
  *C07C 13/39* (2006.01)
  *H01L 51/00* (2006.01)
  *C07C 15/20* (2006.01)
  *C07C 15/52* (2006.01)
  *C07C 211/61* (2006.01)
  *C07D 209/86* (2006.01)
  *C07D 235/18* (2006.01)
  *C07D 333/08* (2006.01)
  *C09K 11/06* (2006.01)
  *H05B 33/14* (2006.01)
  *H01L 51/50* (2006.01)

(52) U.S. Cl.
  CPC ........... *C07C 211/61* (2013.01); *C07D 209/86* (2013.01); *C07D 235/18* (2013.01); *C07D 333/08* (2013.01); *C09K 11/06* (2013.01); *H05B 33/14* (2013.01); *C07C 2103/24* (2013.01); *C09K 2211/1011* (2013.01); *H01L 51/0054* (2013.01); *H01L 51/006* (2013.01); *H01L 51/0071* (2013.01); *H01L 51/5012* (2013.01); *H01L 51/5048* (2013.01); *Y02E 10/549* (2013.01)
  USPC ........................................................ 257/40

(56) References Cited

U.S. PATENT DOCUMENTS

| | | | |
|---|---|---|---|
| 2006/0216633 A1* | 9/2006 | Kubota et al. | 430/139 |
| 2008/0297037 A1 | 12/2008 | Vestweber et al. | |
| 2008/0303423 A1 | 12/2008 | Heil et al. | |
| 2010/0193773 A1 | 8/2010 | Yamamoto et al. | |

FOREIGN PATENT DOCUMENTS

| | | |
|---|---|---|
| EP | 1 717 875 A1 | 11/2006 |
| EP | 1 847 521 A1 | 10/2007 |
| EP | 1 926 159 A1 | 5/2008 |
| EP | 1 932 895 A1 | 6/2008 |
| EP | 1 990 844 A1 | 11/2008 |
| EP | 2 003 107 A1 | 12/2008 |
| EP | 2 008 992 A1 | 12/2008 |
| EP | 2 034 803 A1 | 3/2009 |
| JP | 11-111460 | 4/1999 |
| JP | 2000-007604 A | 1/2000 |
| JP | 2000-053677 A | 2/2000 |
| JP | 2000-344691 A | 12/2000 |
| JP | 2003-115624 | 4/2003 |
| JP | 2005-008559 | 1/2005 |
| JP | 2005-019327 A | 1/2005 |
| JP | 2005-038829 | 2/2005 |
| JP | 3 633236 B2 | 3/2005 |
| JP | 2005-108692 A | 4/2005 |
| JP | 2005-120296 | 5/2005 |
| JP | 2005-285466 | 10/2005 |
| JP | 2005-293961 A | 10/2005 |
| JP | 2005-317450 A | 11/2005 |
| JP | 2006-114844 A | 4/2006 |
| JP | 2009-518342 | 5/2009 |
| JP | 2009-518831 | 5/2009 |
| WO | WO 2004/080975 A1 | 9/2004 |
| WO | WO 2006/085434 A1 | 8/2006 |
| WO | WO 2007/065547 A1 | 6/2007 |
| WO | WO 2007/065678 A1 | 6/2007 |
| WO | WO 2007/069847 A1 | 6/2007 |
| WO | WO 2007/116828 | 10/2007 |

* cited by examiner

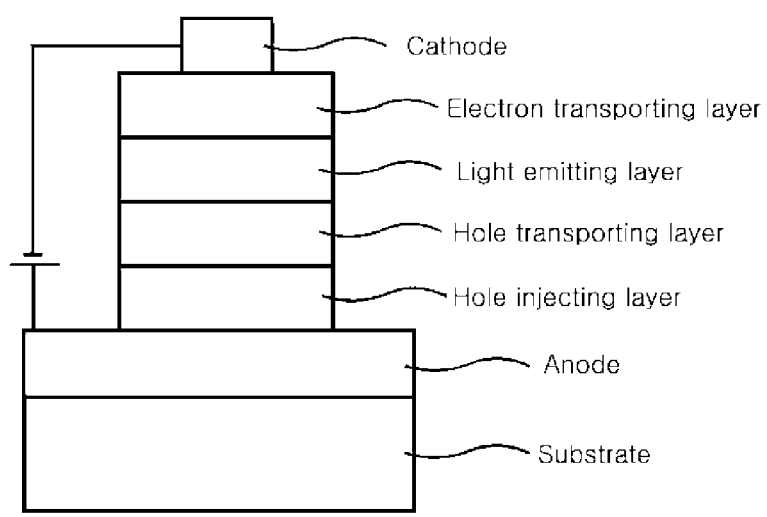

ANTHRACENE DERIVATIVES, PREPARATION METHOD THEREOF AND ORGANIC LIGHT EMITTING DIODE USING THE SAME This application claims the benefit of International Application Number PCT/KR/2007/000442 filed on Jan. 25, 2007 Korean Application No. 10-2006-0009154 filed on Jan. 27, 2006, both of which are hereby incorporated by reference as if fully set forth herein.

TECHNICAL FIELD

The present invention relates to novel anthracene derivatives, preparation method thereof, and an organic electronic device using the same. This application claims priority benefits from Korean Patent Application No. 10-2006-0009154, filed on Jan. 27, 2006, the entire content of which is fully incorporated herein by reference.

BACKGROUND ART

The term "organic electronic device" refers to a device requiring charge exchange between an electrode using holes and/or electrons and an organic material. The organic electronic device can be largely classified into two types according to its operational principle as follows: one type is an electronic device having a configuration in which an exciton is formed in an organic material layer by photons flown from an external light source into the device and the exciton is separated into an electron and a hole, the electron and the hole formed are transported to a different electrode, respectively and used as a current source (voltage source), and the other type is an electronic device having a configuration in which a hole and/or electron are/is injected into an organic material semiconductor forming an interface with an electrode by applying a voltage or current to two or more electrodes to allow the device to operate by means of the injected electron and hole.

Examples of the organic electronic device include an organic light emitting device, an organic solar cell, an organic photoconductor (OPC) drum and an organic transistor, all of which require a hole injecting or hole transporting material, an electron injecting or electron transporting material, or a light emitting material for driving the device. Hereinafter, the organic light emitting device will be mainly and specifically described, but in the above-mentioned organic electronic devices, the hole injecting or hole transporting material, the electron injecting or electron transporting material, or the light emitting material injection functions according to a similar principle.

In general, the term "organic light emitting phenomenon" refers to a phenomenon in which electric energy is converted to light energy by means of an organic material. The organic light emitting device using the organic light emitting phenomenon has a structure usually comprising an anode, a cathode and organic material layers interposed therebetween. Herein, the organic material layer may be mostly formed in a multilayer structure comprising layers of different materials, for example, the hole injecting layer, the hole transporting layer, the light emitting layer, the electron transporting layer, the electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast and high-speed response.

The materials used for the organic material layer of the organic light emitting device can be classified into a light emitting material and a charge transporting material, for example, a hole injecting material, a hole transporting material, an electron transporting material and an electron injecting material, according to their functions. The light emitting material can be divided into a high molecular weight type and a low molecular weight type according to their molecular weight, and divided into a fluorescent material from singlet excited states and a phosphorescent material from triplet excited states according to their light emitting mechanism. Further, the light emitting material can be divided into a blue, green or red light emitting material and a yellow or orange light emitting material required for giving more natural color, according to a light emitting color.

On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer. It is based on the principle that if a small amount of a dopant having a smaller energy band gap than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material and an electron injecting material should be essentially composed of a stable and efficient material. However, the development of a stable and efficient organic material layer material for the organic light emitting device has not yet been fully realized. Accordingly, the development of new materials is continuously desired. The development of such a material is equally required to the above-mentioned other organic electronic devices.

DISCLOSURE

Technical Problem

It is an object of the present invention to provide a novel anthracene derivative.

It is another object of the present invention to provide a method for preparing the anthracene derivative.

It is still another object of the present invention to provide an organic electronic device using the anthracene derivative.

Technical Solution

The present inventors have synthesized a novel anthracene derivative, and then have found that the compound can exhibit effects of increased efficiency, lower operating voltage and higher stability, by using as a light emitting host of a light emitting layer in an organic electronic device, thus completing the present invention.

Advantageous Effects

The anthracene derivative according to the present invention can function alone as a light emitting host, in particular, as a blue host in an organic electronic device. Further, the anthracene derivative according to the present invention can serve as hole injecting, hole transporting, electron injecting, electron transporting, or a light emitting materials in an organic electronic device including an organic light emitting device, and the device according to the present invention exhibits excellent characteristics in efficiency, operating voltage, and stability.

DESCRIPTION OF DRAWINGS

FIG. 1 is a diagram for illustrating the structures of the organic light emitting devices applicable to the present invention.

MODE FOR INVENTION

The present invention provides an anthracene derivative represented by the following formula 1:

[Formula 1]

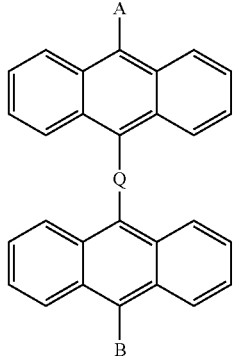

wherein A and B may be the same as or different from each other, and are each a $C_5$ to $C_{20}$ aryl group which is substituted or unsubstituted with at least one group selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_1$ to $C_{20}$ alkylthio group, a $C_2$ to $C_{20}$ alkenyl group, a $C_2$ to $C_{20}$ alkynyl group, a $C_3$ to $C_{20}$ cycloalkyl group, a $C_5$ to $C_{20}$ aryl group, a substituted or unsubstituted silane group and $C_5$ to $C_{20}$ heterocyclic group having O, N or S; a $C_5$ to $C_{20}$ heterocyclic group having O, N or S which is substituted or unsubstituted with at least one group selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_1$ to $C_{20}$ alkylthio group, a $C_2$ to $C_{20}$ alkenyl group, a $C_2$ to $C_{20}$ alkynyl group, a $C_3$ to $C_{20}$ cycloalkyl group, a $C_5$ to $C_{20}$ aryl group, a substituted or unsubstituted silane group and $C_5$ to $C_{20}$ heterocyclic group having O, N or S; or a $C_5$ to $C_{20}$ arylamine group which is substituted or unsubstituted with at least one group selected from the group consisting of an alkyl group and alkylsilyl group, and Q is a group selected from the group consisting of the following structural formulae:

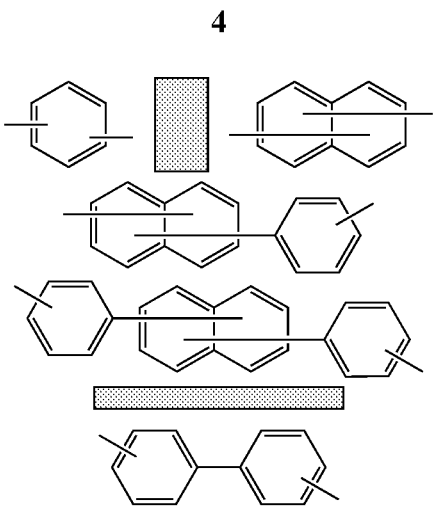

In the formula 1, A and B may be preferably the same as or different from each other, and are each a $C_5$ to $C_{20}$ aryl group which is substituted or unsubstituted with at least one group selected from the group consisting of F, Cl, Br, CN, $NO_2$, a methyl group, an ethyl group, a propyl group, an isopropyl group, a butyl group, a t-butyl group, a pentyl group, a hexyl group, a heptyl group, a methoxy group, an ethoxy group, a methylthio group, an ethylthio group, a stilbenyl group, a styrenyl group, a cyclopentyl group, a cyclohexyl group, a phenyl group, a naphthyl group, an anthracenyl group, a thiophene group, a puran group, a pyran group, a pyrrole group, an imidazole group, a pyrazole group, a thiazole group, a pyridine group, a pyrazine group, a pyrimidine group, a silole group, a pyridazine group; or a $C_5$ to $C_{20}$ heterocyclic group having O, N or S which is substituted or unsubstituted with at least one group selected from the group consisting of F, Cl, Br, CN, $NO_2$, a methyl group, an ethyl group, a propyl group, an isopropyl group, a butyl group, a t-butyl group, a pentyl group, a hexyl group, a heptyl group, a methoxy group, an ethoxy group, a methylthio group, an ethylthio group, a stilbenyl group, a styrenyl group, a cyclopentyl group, a cyclohexyl group, a phenyl group, a naphthyl group, an anthracenyl group, a thiophene group, a puran group, a pyran group, a pyrrole group, an imidazole group, a pyrazole group, a thiazole group, a pyridine group, a pyrazine group, a pyrimidine group, a silole group, a pyridazine group.

More preferably, in the formula 1, A and B may be the same as or different from each other, and are each a group selected from the group consisting of a phenyl group, a naphthyl group, an anthracenyl group, a pyrenyl group, a perylenyl group, a pyridyl group, a bipyridyl group, a carbazole group, a thiophenyl group, a quinolinyl group and an isoquinolinyl group, and Q is a group selected from the group consisting of the following structural formulae:

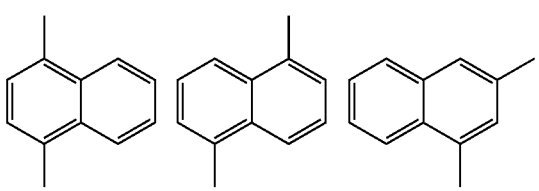

-continued
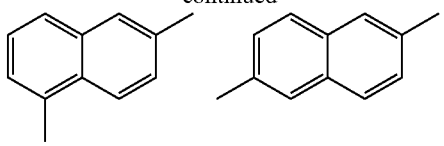
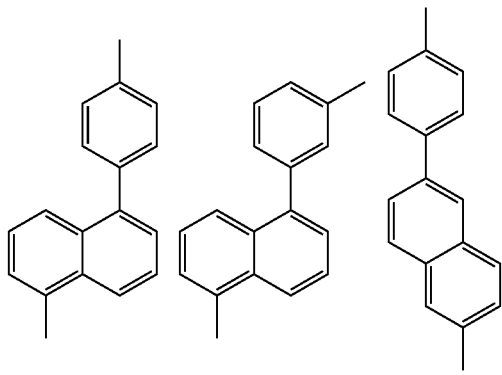
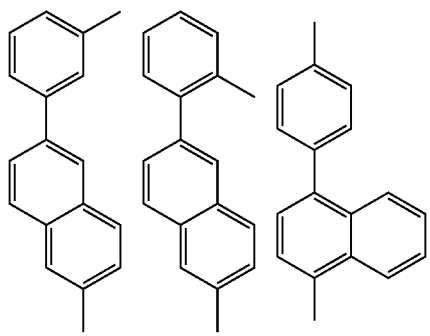
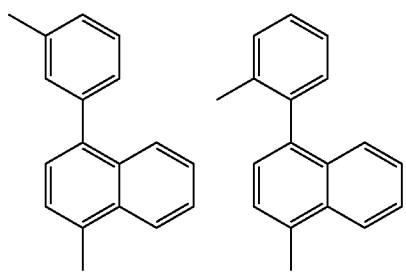
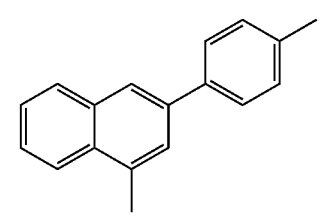
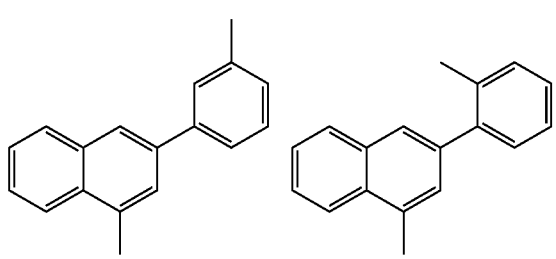
-continued
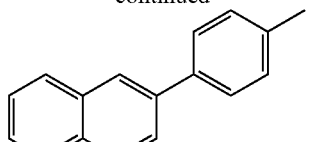
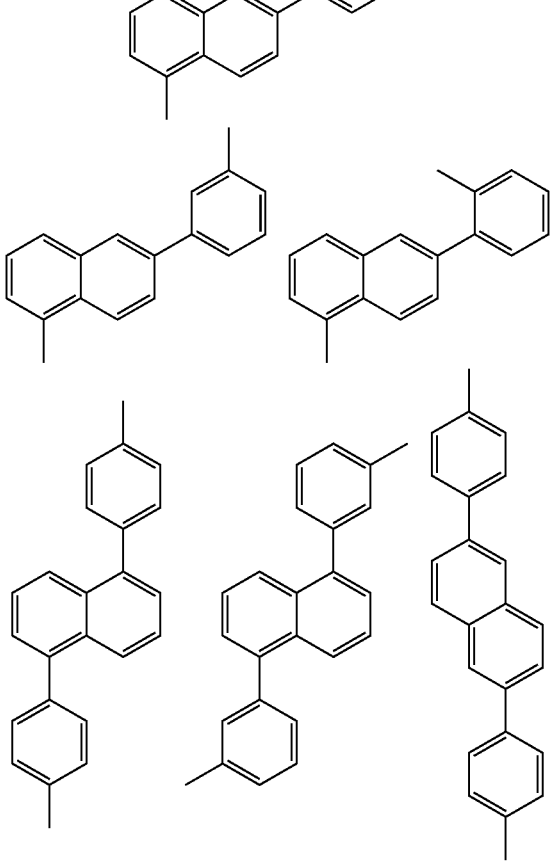
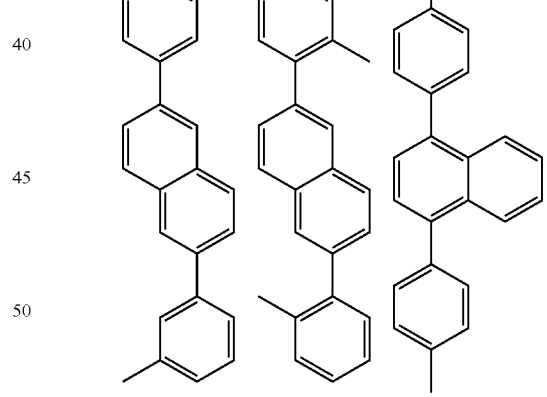
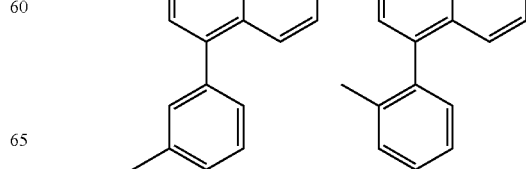

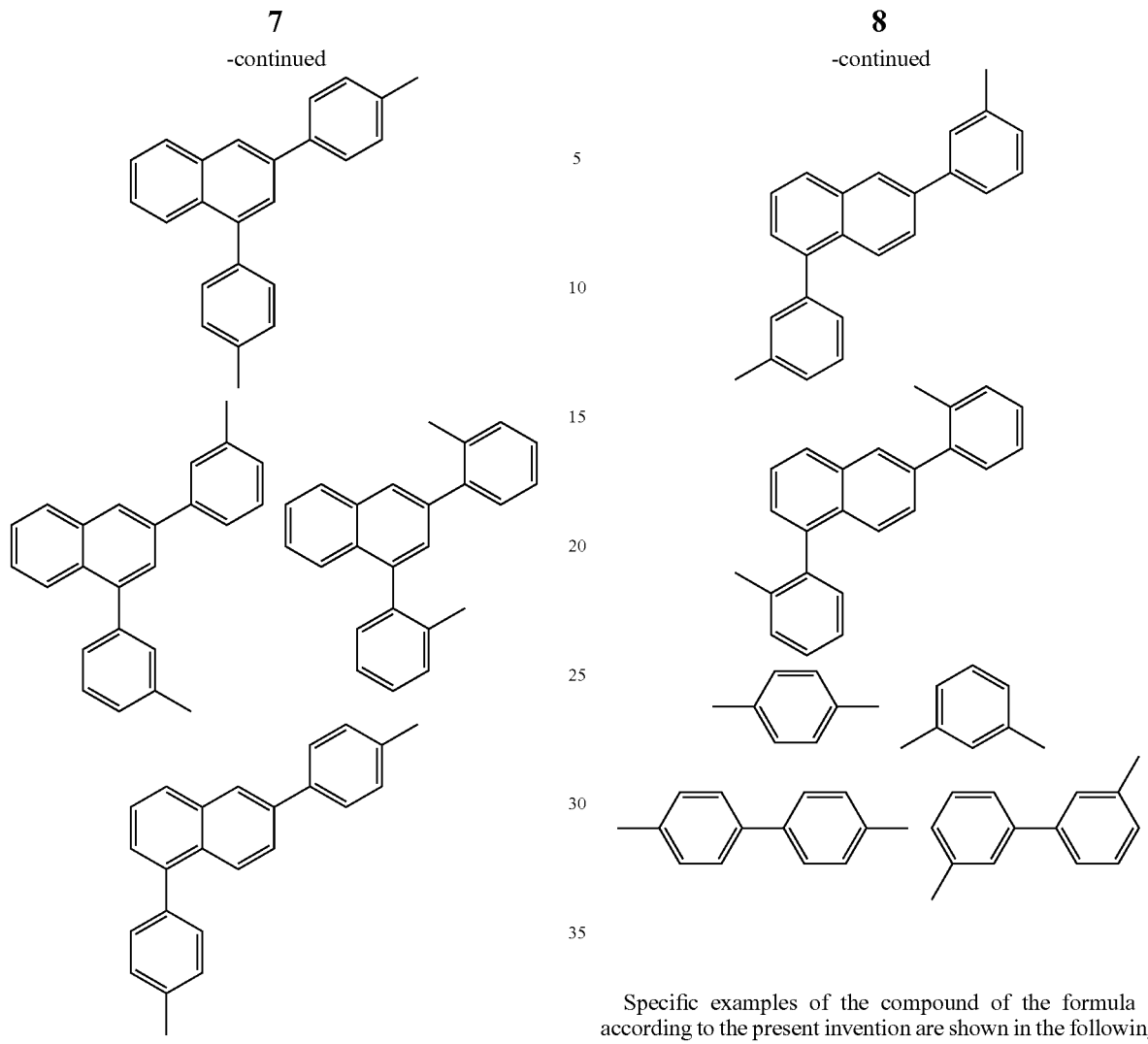
Specific examples of the compound of the formula 1 according to the present invention are shown in the following table 1, but not limited thereto.

TABLE 1-continued
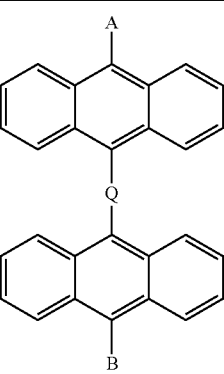
| Q | A | B |
|---|---|---|
| 2 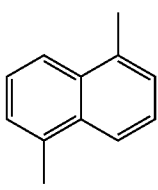 | 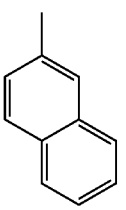 | 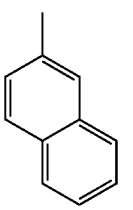 |
| 3 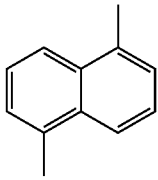 | 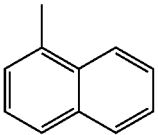 | 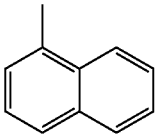 |
| 4 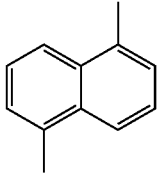 | 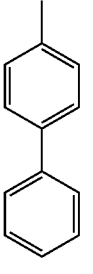 | 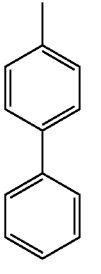 |
| 5 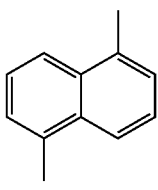 | 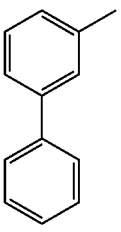 | 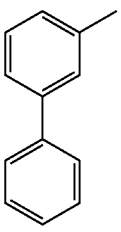 |

TABLE 1-continued
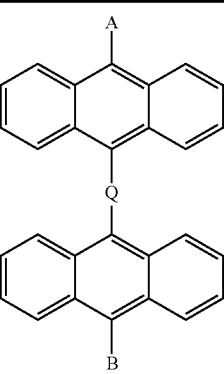
| Q | A | B |
|---|---|---|
| 6 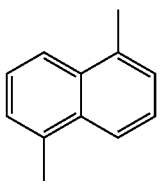 | 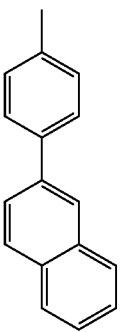 | 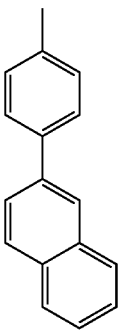 |
| 7 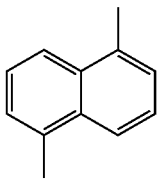 | 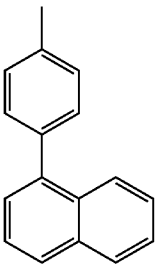 | 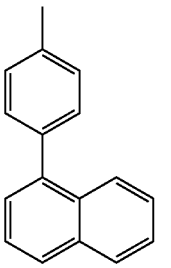 |
| 8 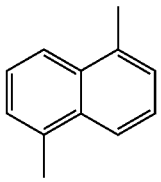 | 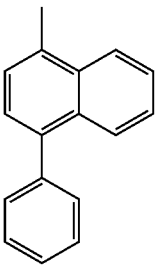 | 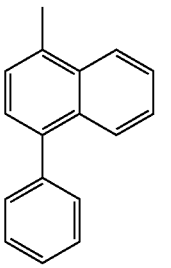 |
| 9 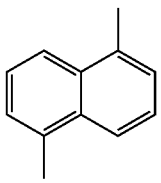 | 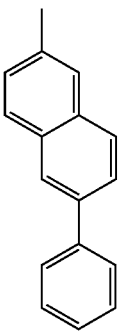 | 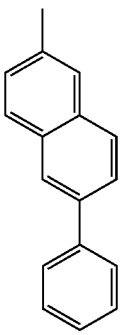 |

TABLE 1-continued
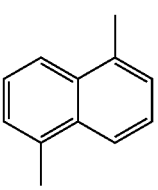
| Q | A | B |
|---|---|---|
| 10 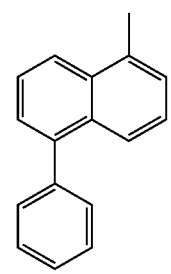 | 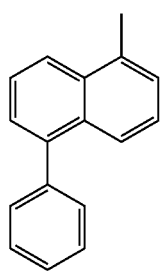 | 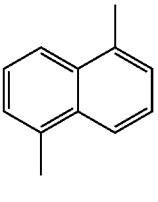 |
| 11 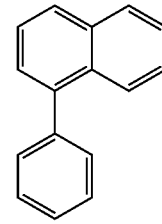 | 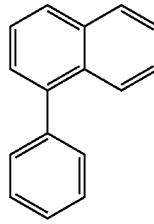 | 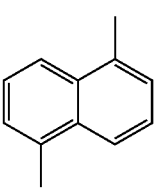 |
| 12 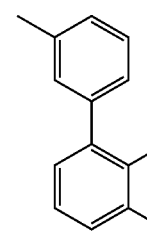 | 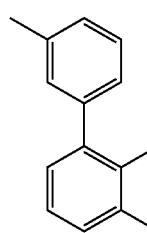 | 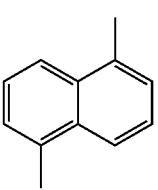 |
| 13 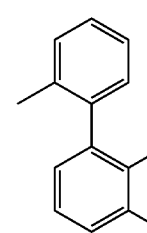 | 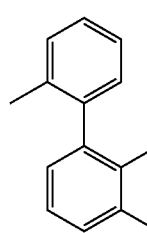 |  |

TABLE 1-continued
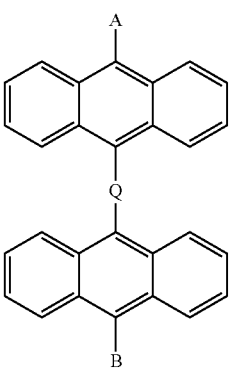
| Q | A | B |
|---|---|---|
| 14 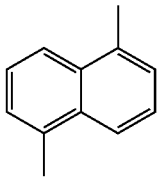 | 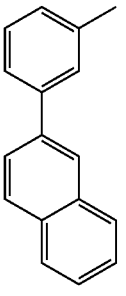 | 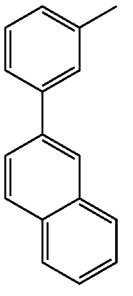 |
| 15 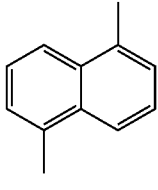 | 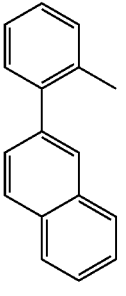 | 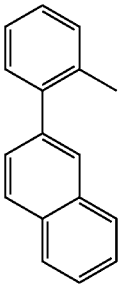 |
| 16 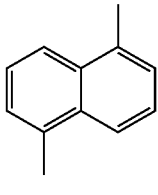 | 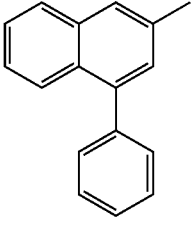 | 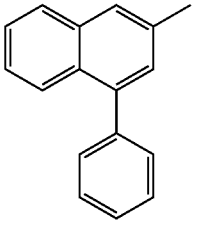 |
| 17 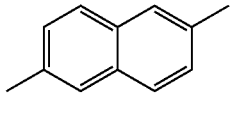 | 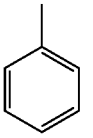 | 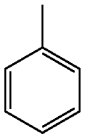 |
| 18 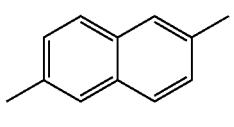 | 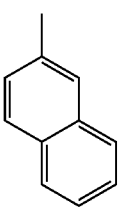 | 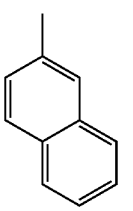 |

TABLE 1-continued
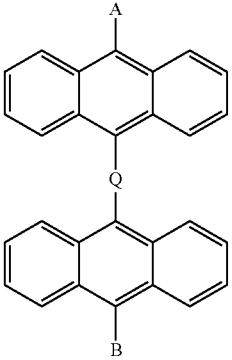
| | Q | A | B |
|---|---|---|---|
| 19 | 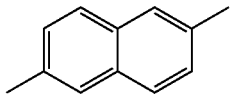 | 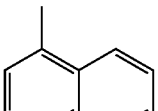 | 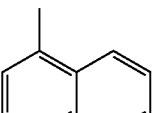 |
| 20 | 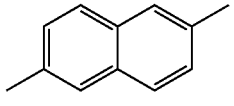 | 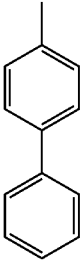 | 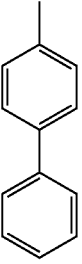 |
| 21 | 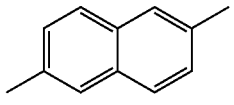 | 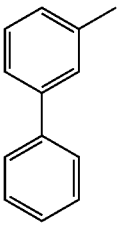 | 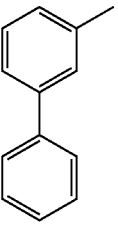 |
| 22 | 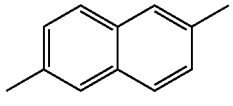 | 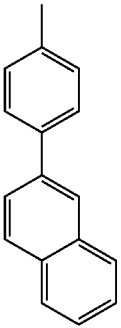 | 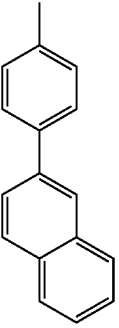 |

TABLE 1-continued
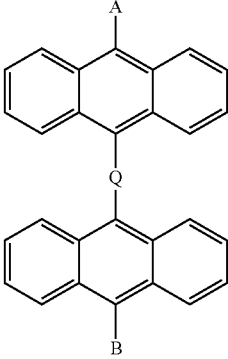
| | Q | A | B |
|---|---|---|---|
| 23 | 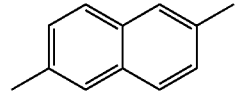 | 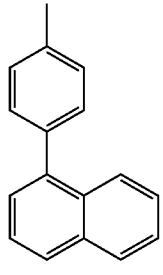 | 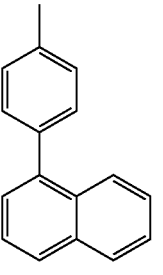 |
| 24 | 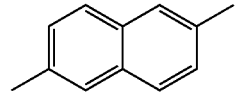 | 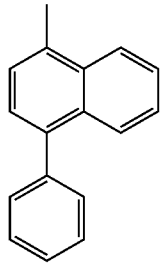 | 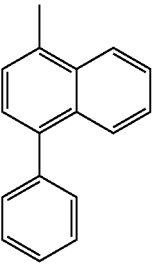 |
| 25 | 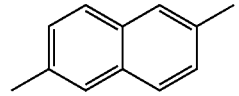 | 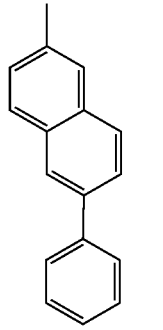 | 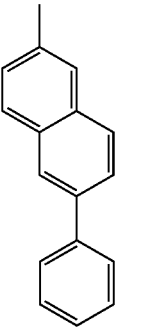 |
| 26 | 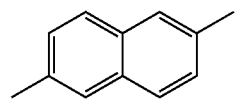 | 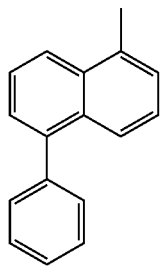 | 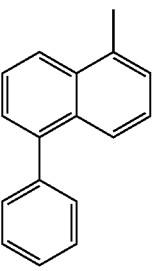 |

TABLE 1-continued
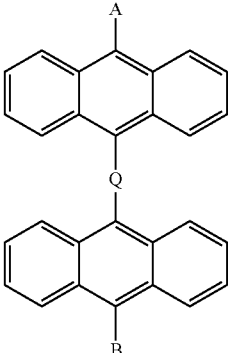
| | Q | A | B |
|---|---|---|---|
| 27 | 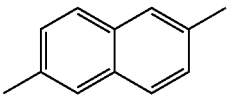 | 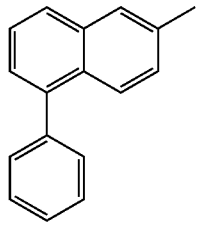 | 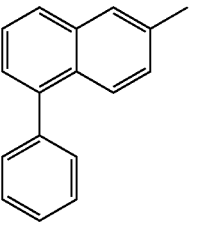 |
| 28 | 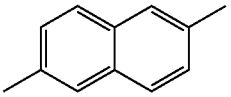 | 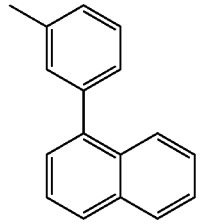 | 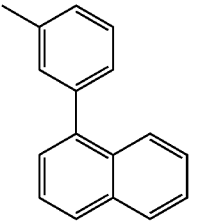 |
| 29 | 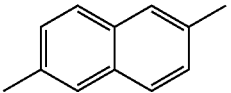 | 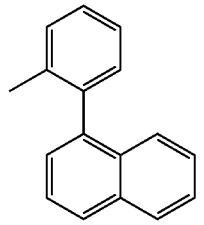 | 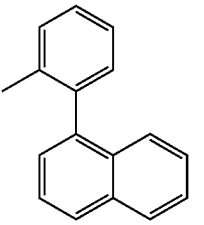 |
| 30 | 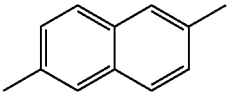 | 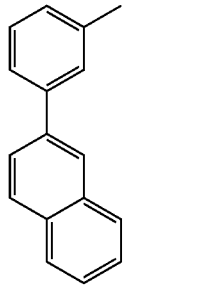 | 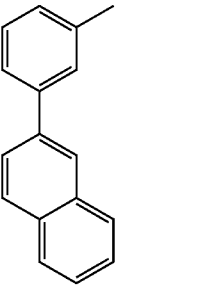 |

TABLE 1-continued
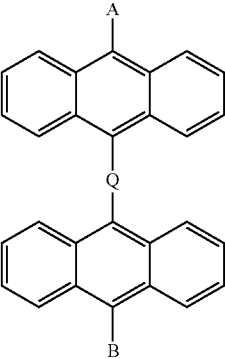
| | Q | A | B |
|---|---|---|---|
| 31 | 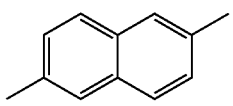 | 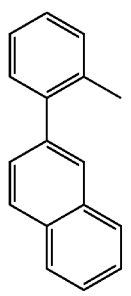 | 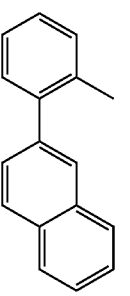 |
| 32 | 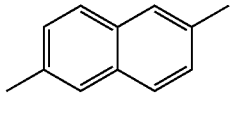 | 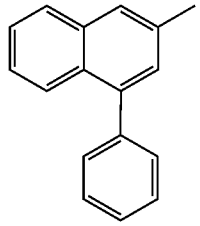 | 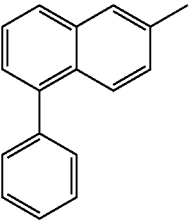 |
| 33 | 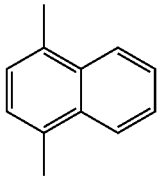 | 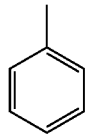 | 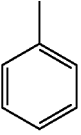 |
| 34 | 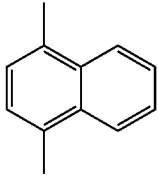 | 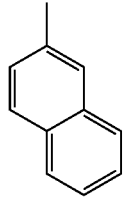 | 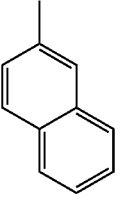 |
| 35 | 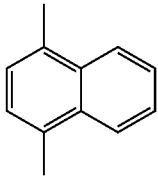 | 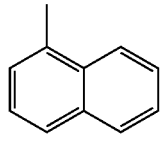 | 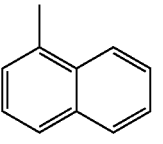 |

TABLE 1-continued
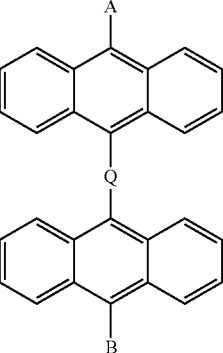
| Q | A | B |
|---|---|---|
| 36 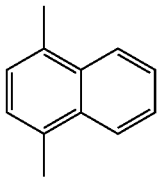 | 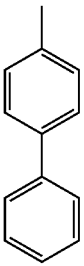 | 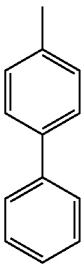 |
| 37 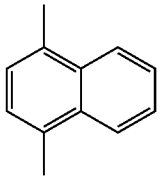 | 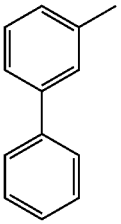 | 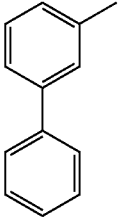 |
| 38 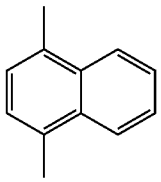 | 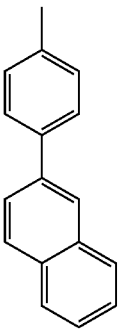 | 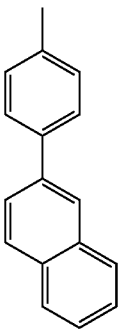 |
| 39 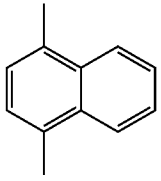 | 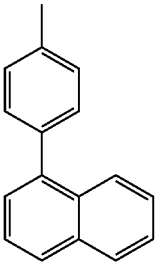 | 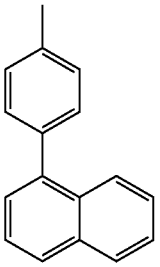 |

TABLE 1-continued
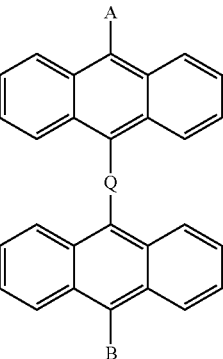
| Q | A | B |
|---|---|---|
| 40 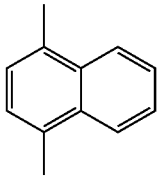 | 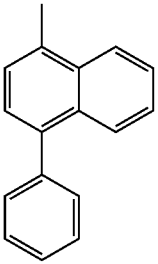 | 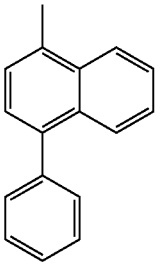 |
| 41 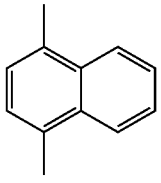 | 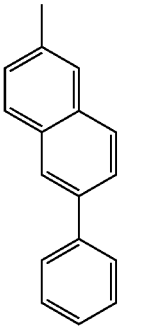 | 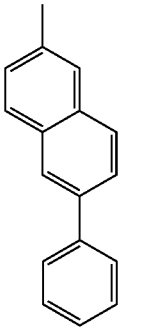 |
| 42 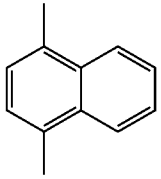 | 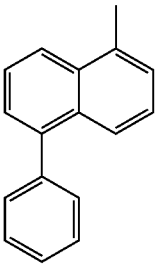 | 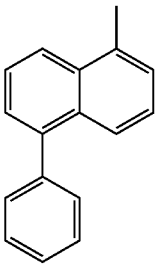 |
| 43 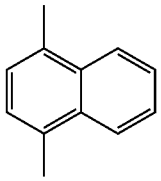 | 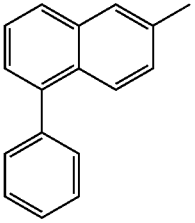 | 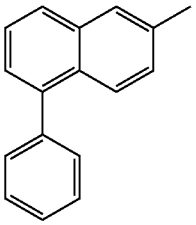 |

TABLE 1-continued
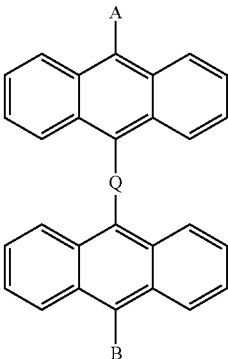
| | Q | A | B |
|---|---|---|---|
| 44 | 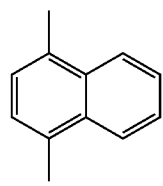 | 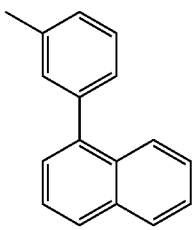 | 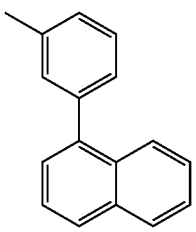 |
| 45 | 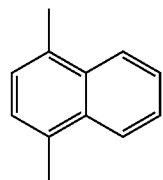 | 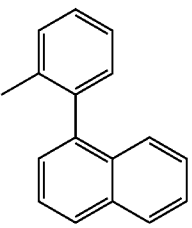 | 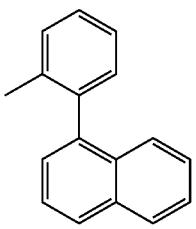 |
| 46 | 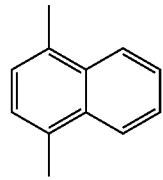 | 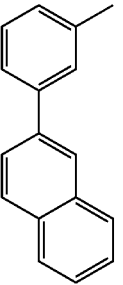 | 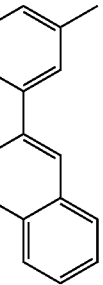 |
| 47 | 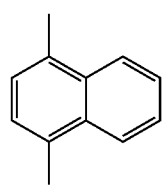 | 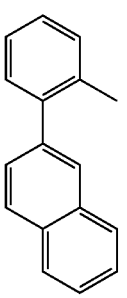 | 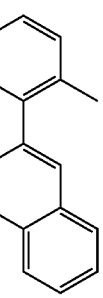 |

TABLE 1-continued
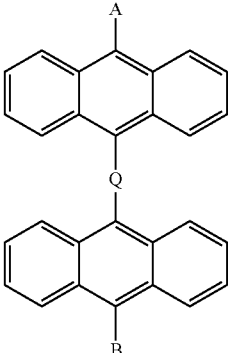
| | Q | A | B |
|---|---|---|---|
| 48 | 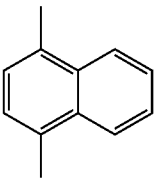 | 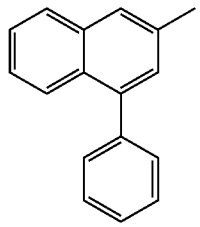 | 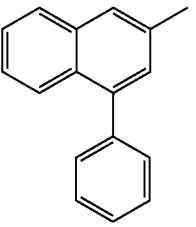 |
| 49 | 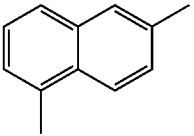 | 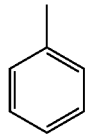 | 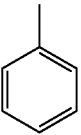 |
| 50 | 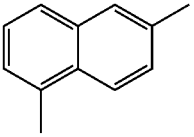 | 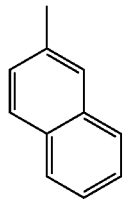 | 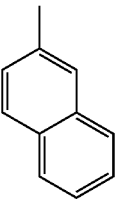 |
| 51 | 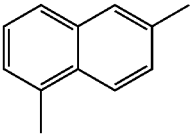 | 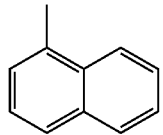 | 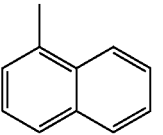 |
| 52 | 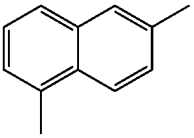 | 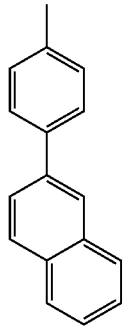 | 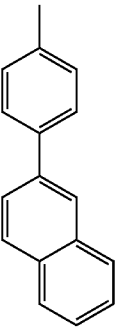 |

TABLE 1-continued
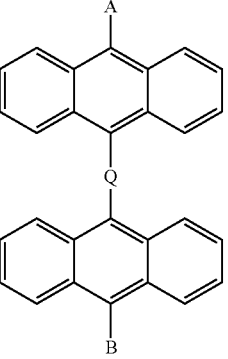
| | Q | A | B |
|---|---|---|---|
| 53 | 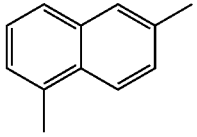 | 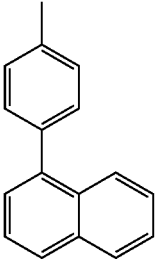 | 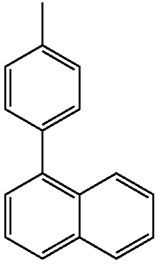 |
| 54 | 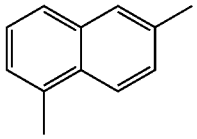 | 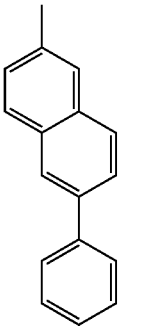 | 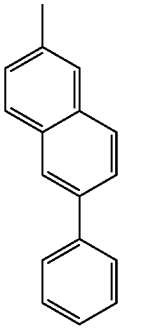 |
| 55 | 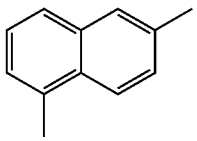 | 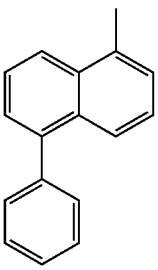 | 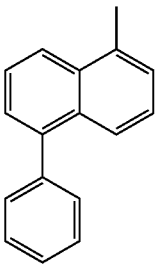 |
| 56 | 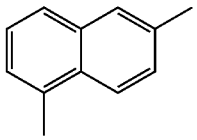 | 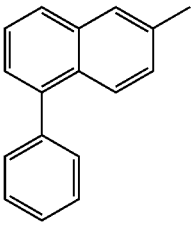 | 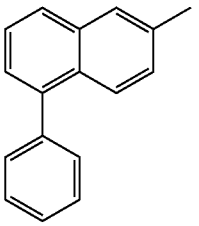 |

TABLE 1-continued
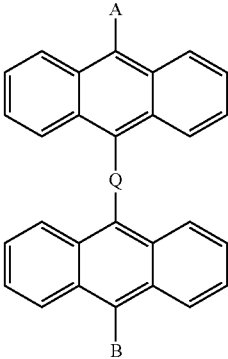
| | Q | A | B |
|---|---|---|---|
| 57 | 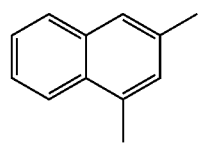 | 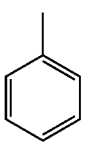 | 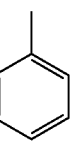 |
| 58 | 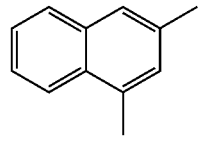 | 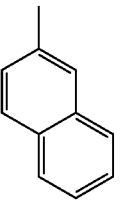 | 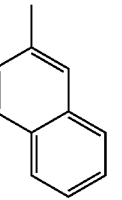 |
| 59 | 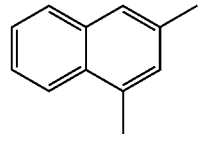 | 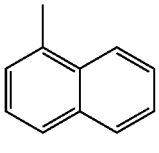 | 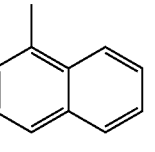 |
| 60 | 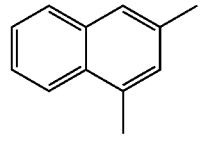 | 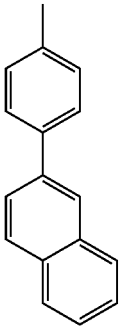 | 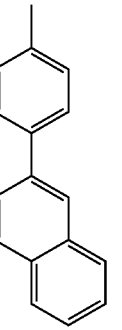 |
| 61 | 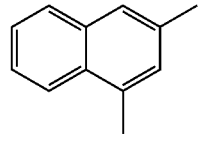 | 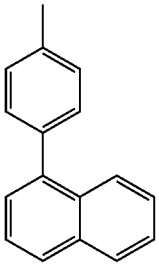 | 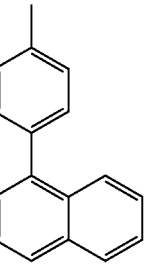 |

TABLE 1-continued
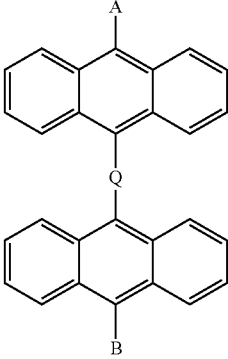
| | Q | A | B |
|---|---|---|---|
| 62 | 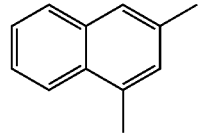 | 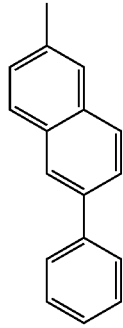 | 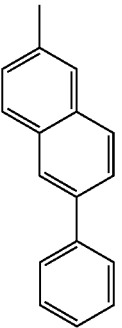 |
| 63 | 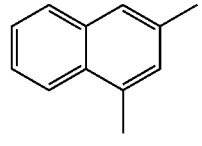 | 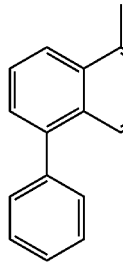 | 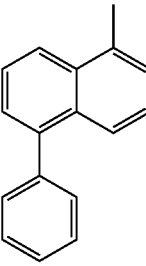 |
| 64 | 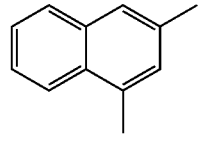 | 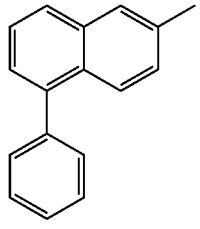 | 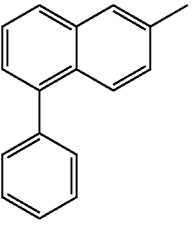 |
| 65 | 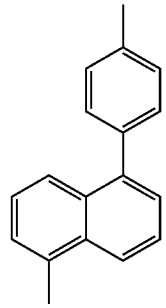 | 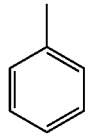 | 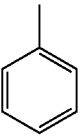 |

TABLE 1-continued
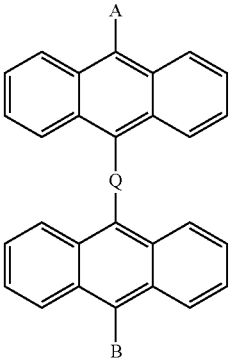
| | Q | A | B |
|---|---|---|---|
| 66 | 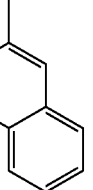 | 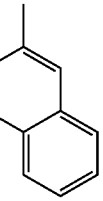 | 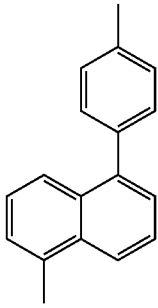 |
| 67 | 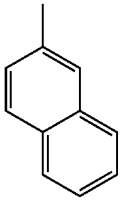 | 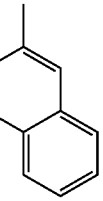 | 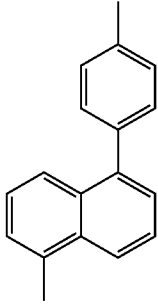 |
| 68 | 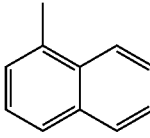 | 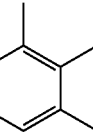 | 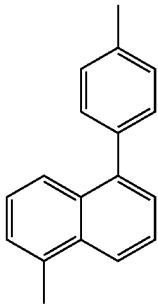 |

TABLE 1-continued
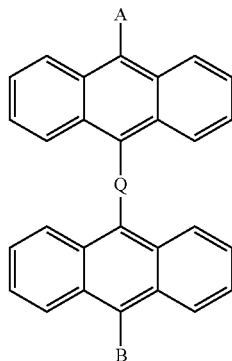
| | Q | A | B |
|---|---|---|---|
| 69 | 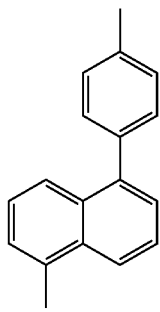 | 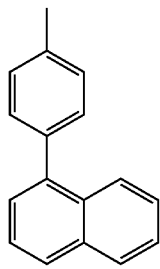 | 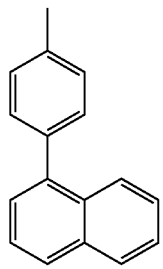 |
| 70 | 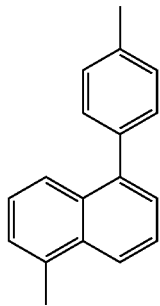 | 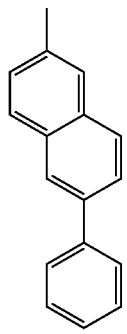 | 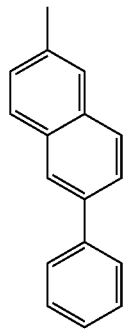 |
| 71 | 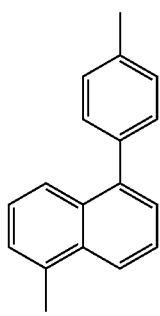 | 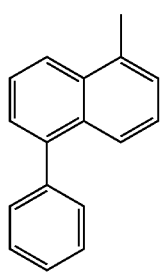 | 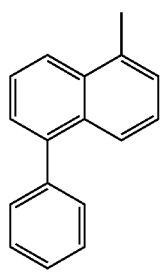 |

TABLE 1-continued
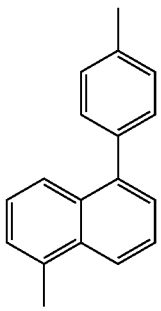 [SMILES: Cc1ccc(-c2cccc3c(C)cccc23)cc1]
| | Q | A | B |
|---|---|---|---|
| 72 | 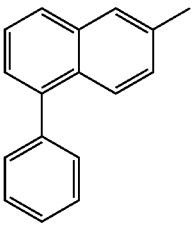 | 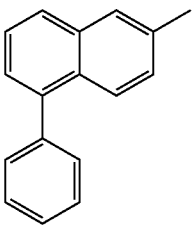 | 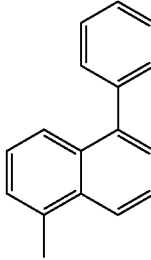 |
| 73 | 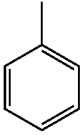 | 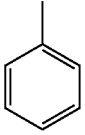 | 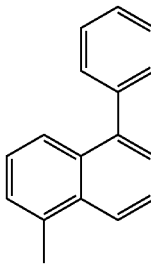 |
| 74 | 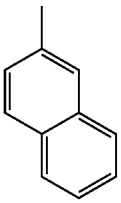 | 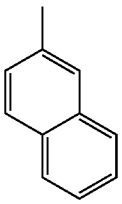 | 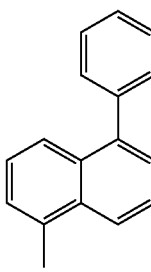 |
| 75 | 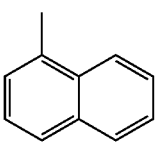 | 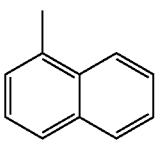 | |

TABLE 1-continued
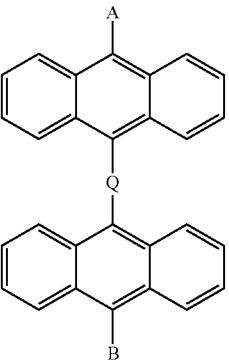
| Q | A | B |
|---|---|---|
| 76 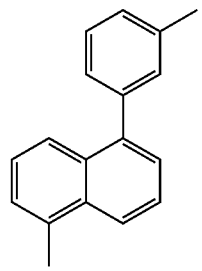 | 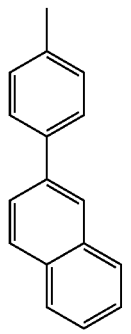 | 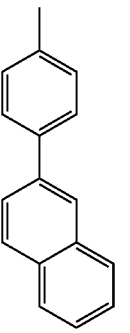 |
| 77 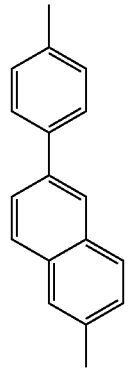 | 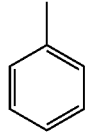 | 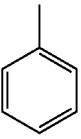 |
| 78 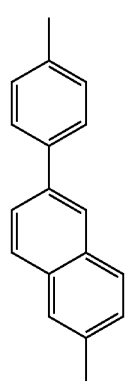 | 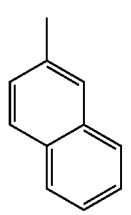 | 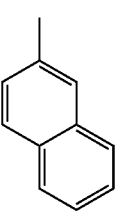 |

TABLE 1-continued
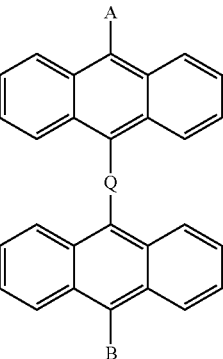
| Q | A | B |
|---|---|---|
| 79 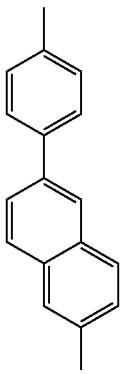 | 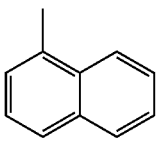 | 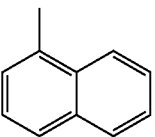 |
| 80 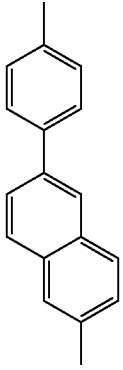 | 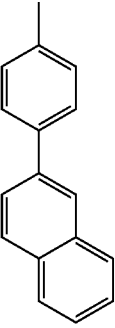 | 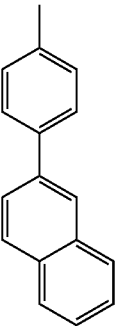 |
| 81 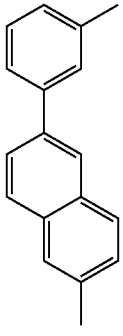 | 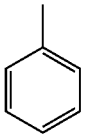 | 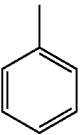 |

TABLE 1-continued
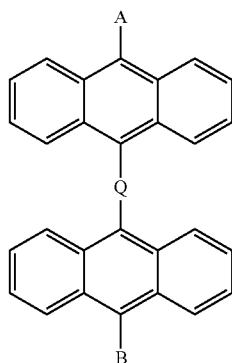
| | Q | A | B |
|---|---|---|---|
| 82 | 3-methylphenyl-2,6-dimethylnaphthyl | 2-methylnaphthyl | 2-methylnaphthyl |
| 83 | 3-methylphenyl-2,6-dimethylnaphthyl | 1-methylnaphthyl | 1-methylnaphthyl |
| 84 | 2-methylphenyl-2,6-dimethylnaphthyl | 4-(2-naphthyl)phenyl | 4-(2-naphthyl)phenyl |

TABLE 1-continued
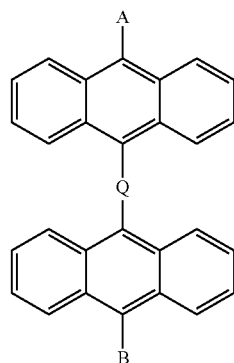
| | Q | A | B |
|---|---|---|---|
| 85 | 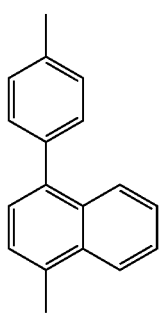 | 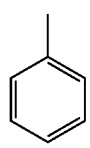 | 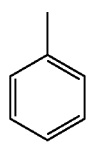 |
| 86 | 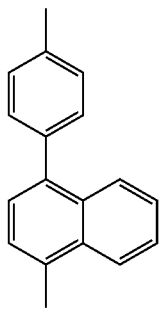 | 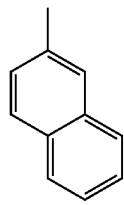 | 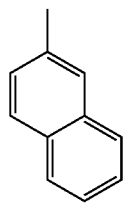 |
| 87 | 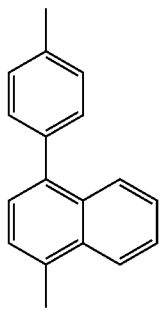 | 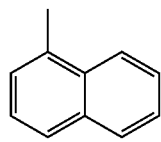 | 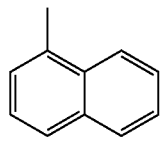 |

TABLE 1-continued

| Q | A | B |
|---|---|---|
| 88 | | |
| 89 | | |
| 90 | | |
| 91 | | |

TABLE 1-continued
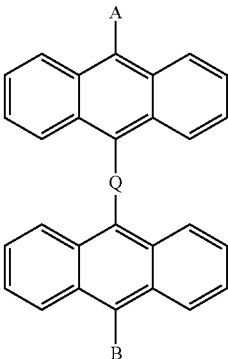
| Q | A | B |
|---|---|---|
| 92 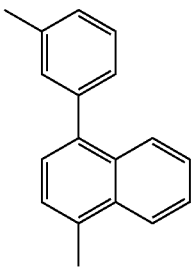 | 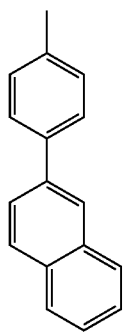 | 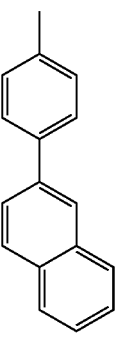 |
| 93 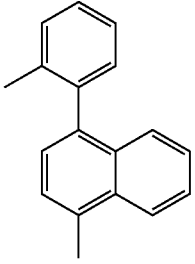 | 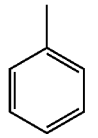 | 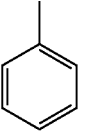 |
| 94 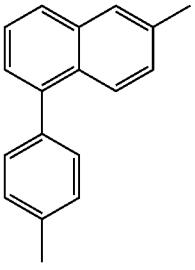 | 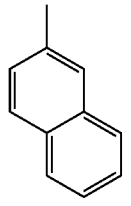 | 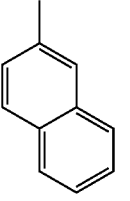 |
| 95 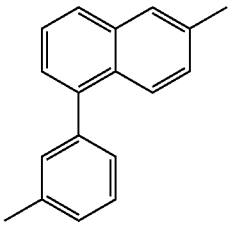 | 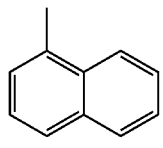 | 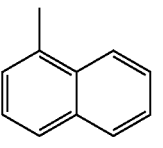 |

TABLE 1-continued
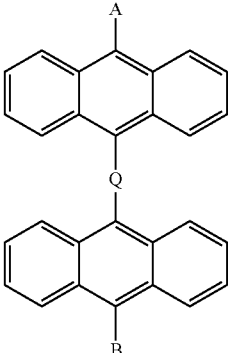
| | Q | A | B |
|---|---|---|---|
| 96 | 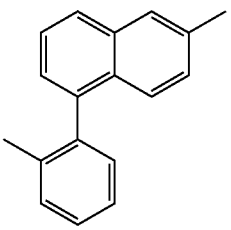 | 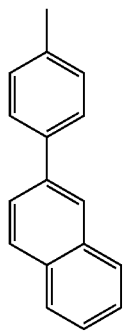 | 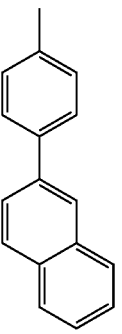 |
| 97 | 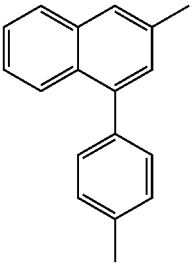 | 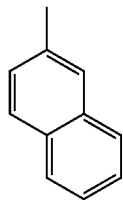 | 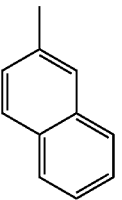 |
| 98 | 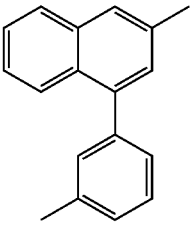 | 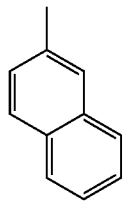 | 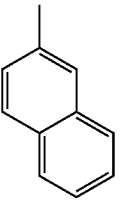 |
| 99 | 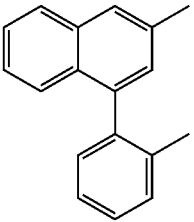 | 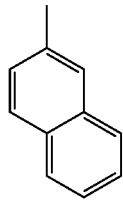 | 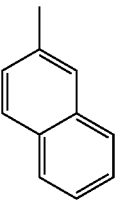 |

TABLE 1-continued
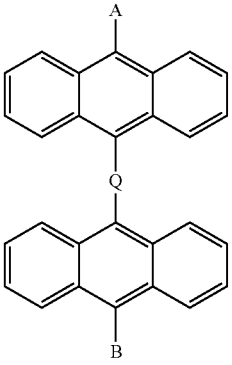
| | Q | A | B |
|---|---|---|---|
| 100 | 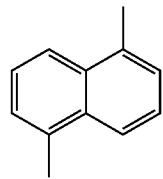 | 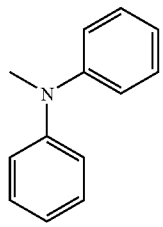 | 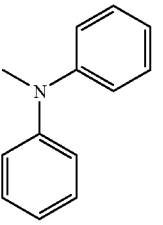 |
| 101 | 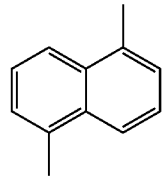 | 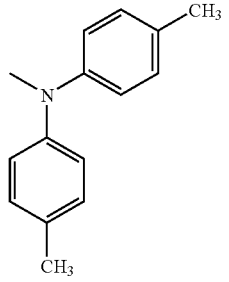 | 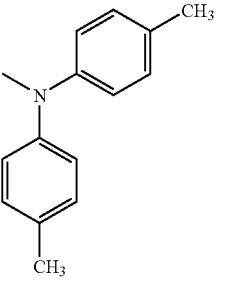 |
| 102 | 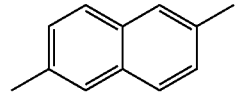 | 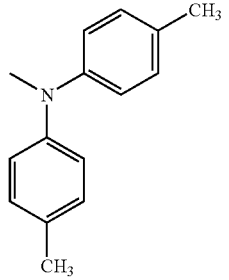 | 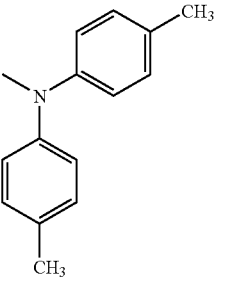 |
| 103 | 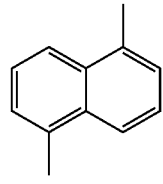 | 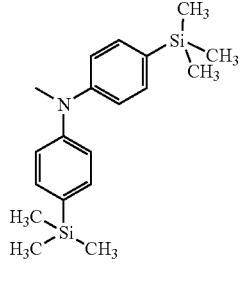 | 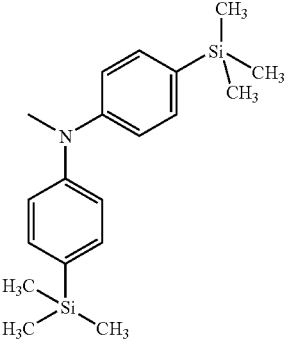 |

TABLE 1-continued
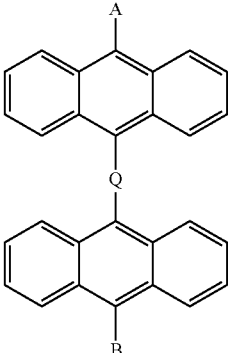
| | Q | A | B |
|---|---|---|---|
| 104 | 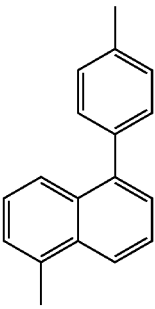 | 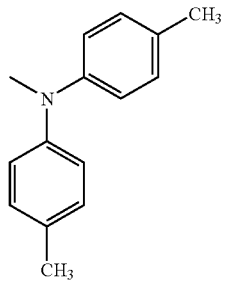 | 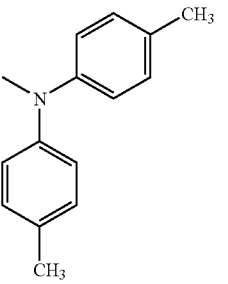 |
| 105 | 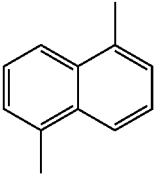 | 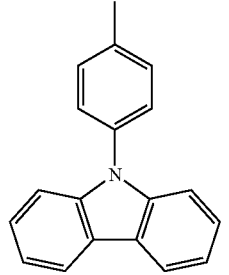 | 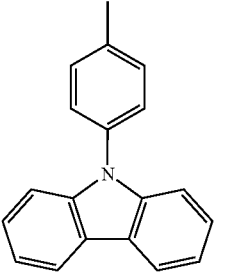 |
| 106 | 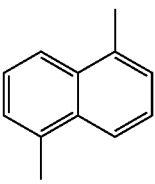 | 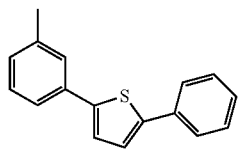 | 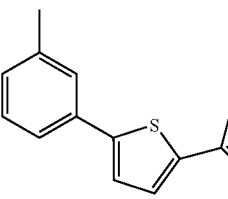 |
| 107 | 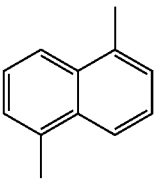 | 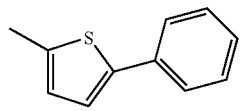 | 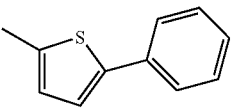 |

TABLE 1-continued
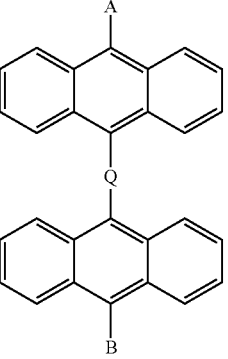
| | Q | A | B |
|---|---|---|---|
| 108 | 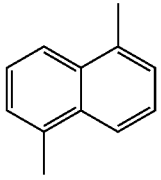 | 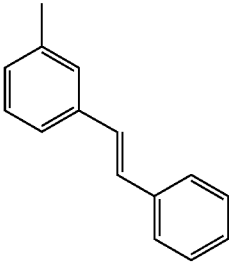 | 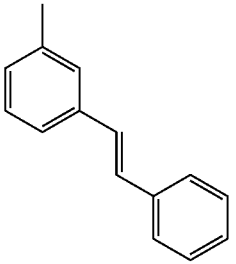 |
| 109 | 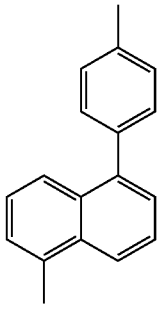 | 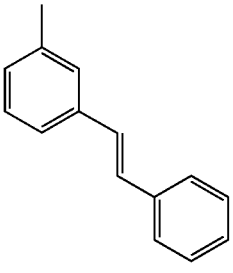 | 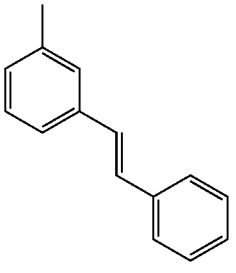 |
| 110 | 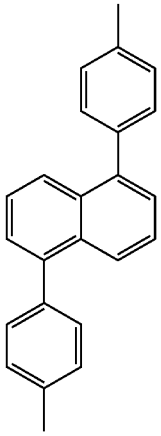 | 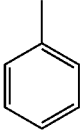 | 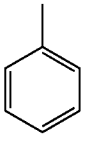 |

TABLE 1-continued
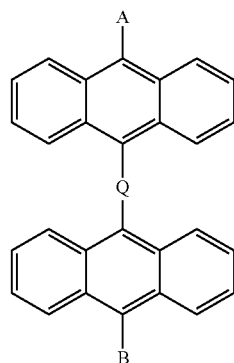
| Q | A | B |
|---|---|---|
| 111 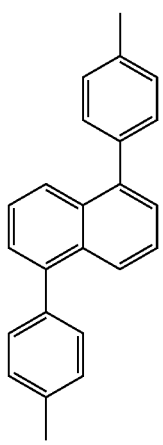 | 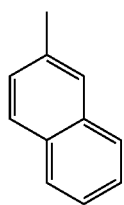 | 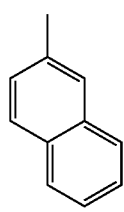 |
| 112 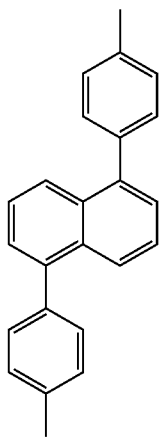 | 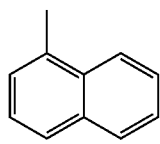 | 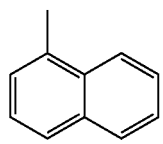 |

TABLE 1-continued
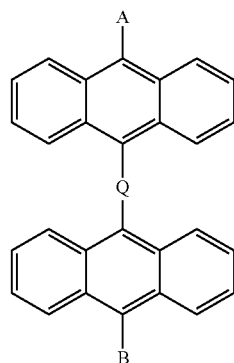
| Q | A | B |
|---|---|---|
| 113 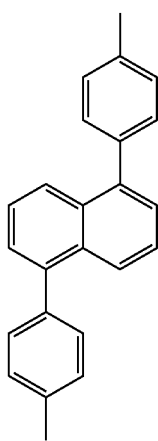 | 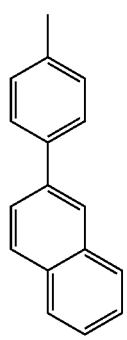 | 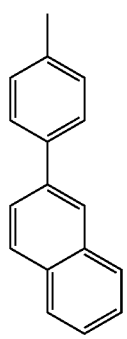 |
| 114 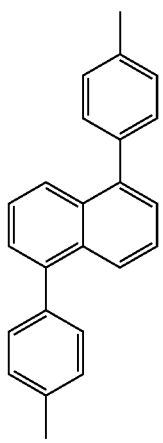 | 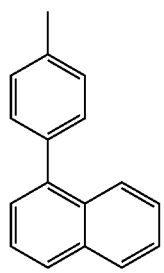 | 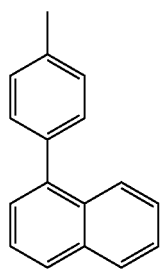 |

TABLE 1-continued
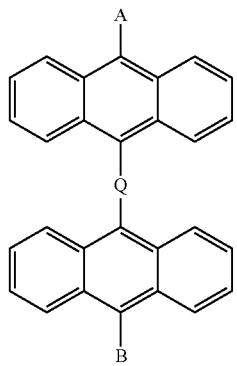
| Q | A | B |
|---|---|---|
| 115 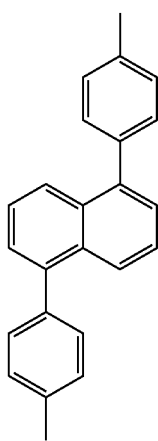 | 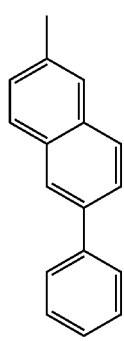 | 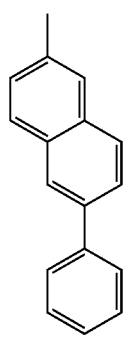 |
| 116 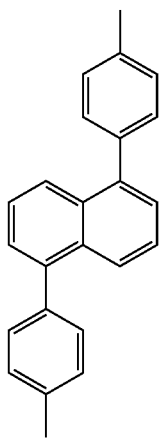 | 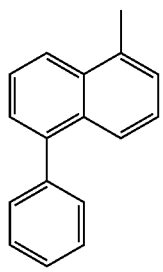 | 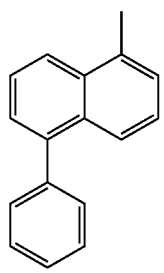 |

TABLE 1-continued
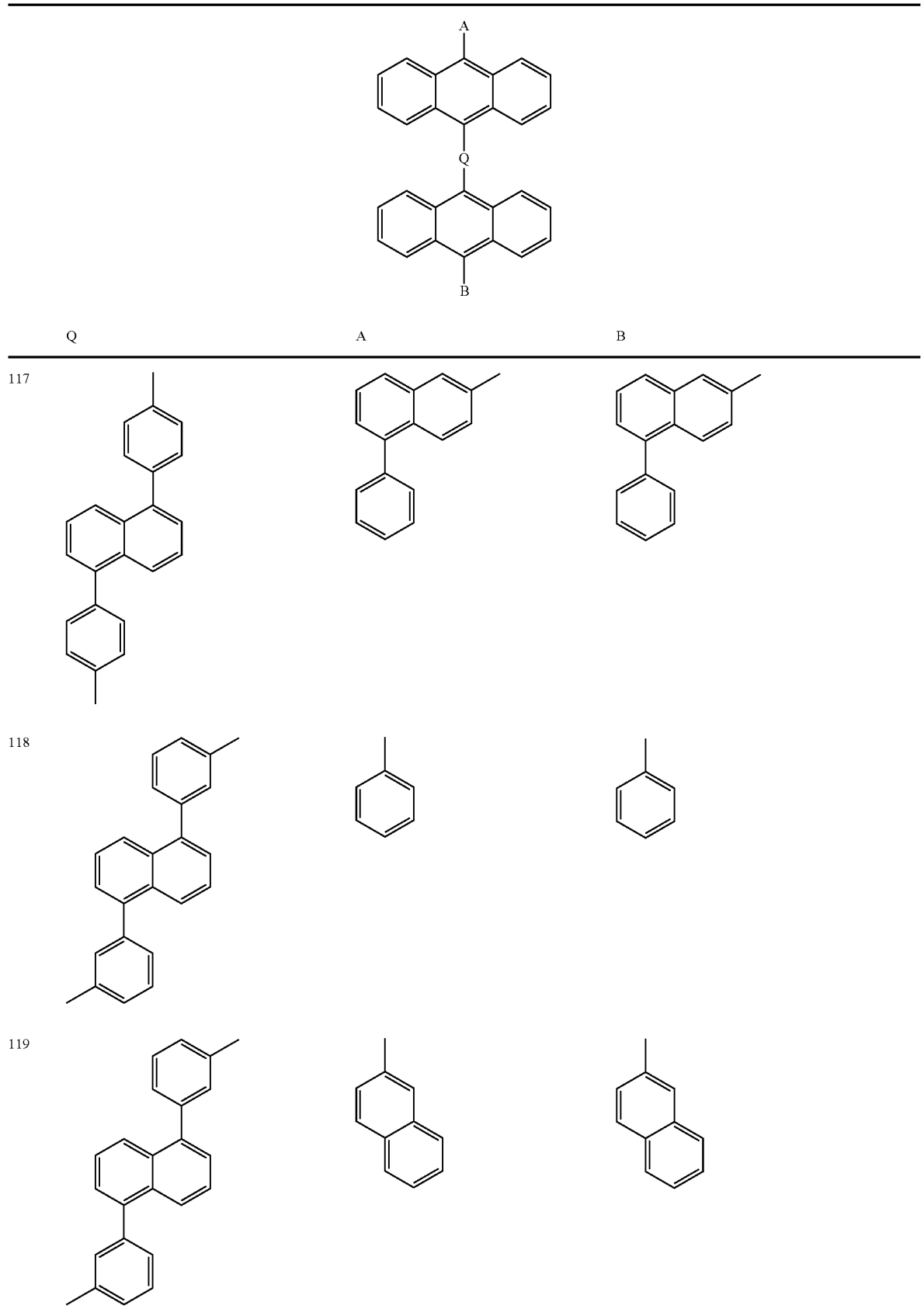

TABLE 1-continued
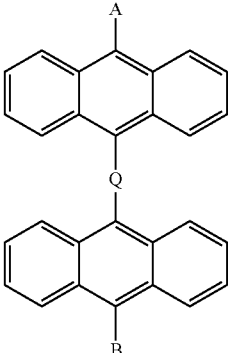
| | Q | A | B |
|---|---|---|---|
| 120 | 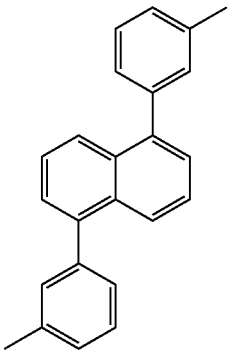 | 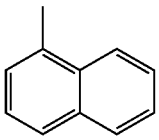 | 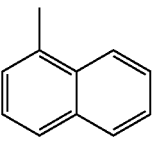 |
| 121 | 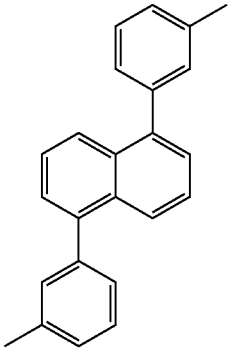 | 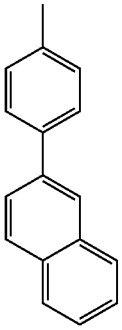 | 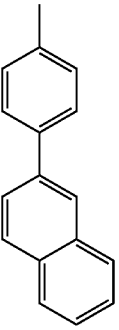 |
| 122 | 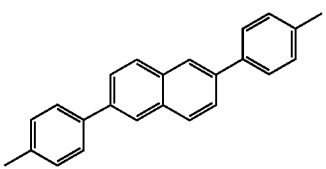 | 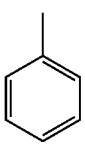 | 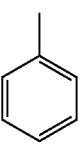 |
| 123 | 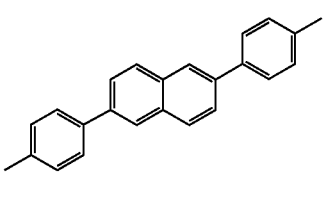 | 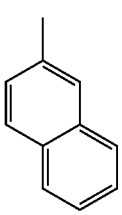 | 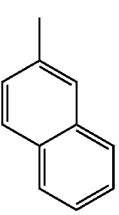 |

TABLE 1-continued
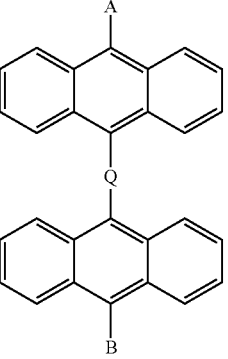
| | Q | A | B |
|---|---|---|---|
| 124 |  |  | 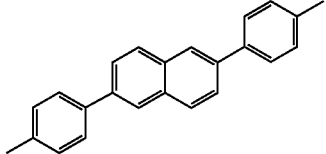 |
| 125 | 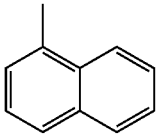 | 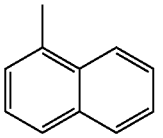 | 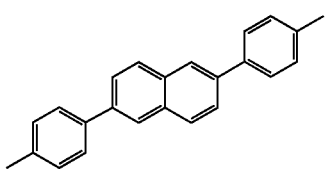 |
| 126 | 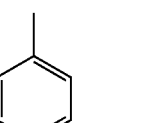 | 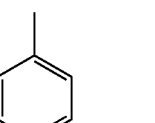 | 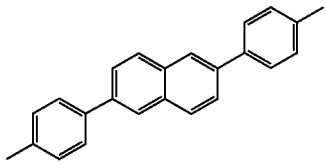 |
| 127 | 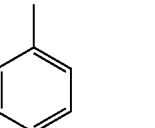 | 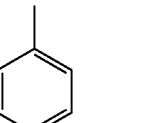 | 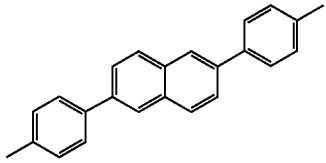 |

TABLE 1-continued
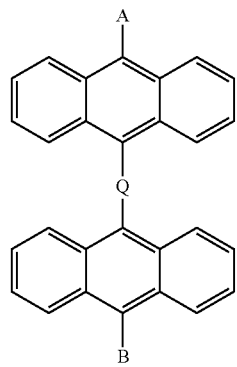
| | Q | A | B |
|---|---|---|---|
| 128 | 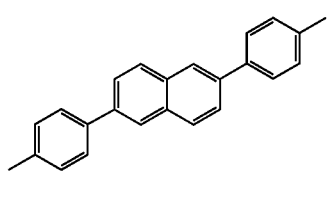 | 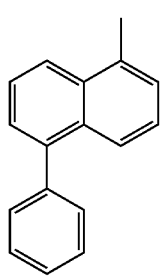 | 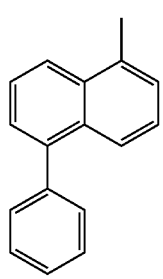 |
| 129 | 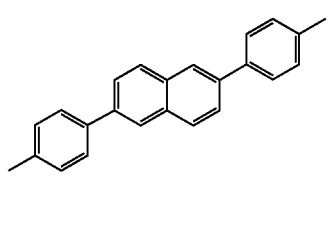 | 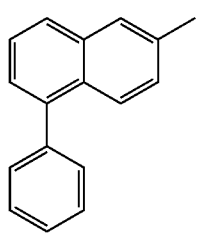 | 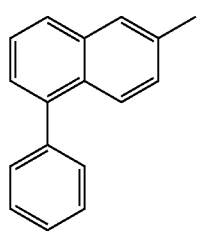 |
| 130 | 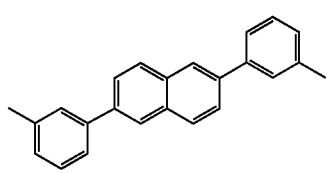 | 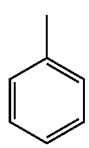 | 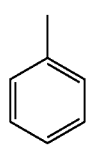 |
| 131 | 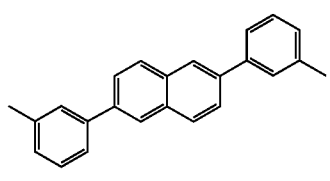 | 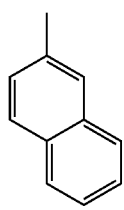 | 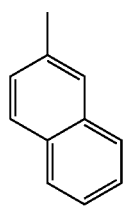 |
| 132 | 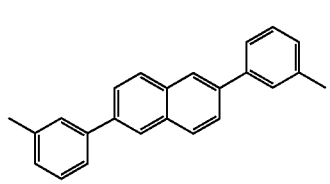 | 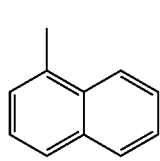 | |

TABLE 1-continued
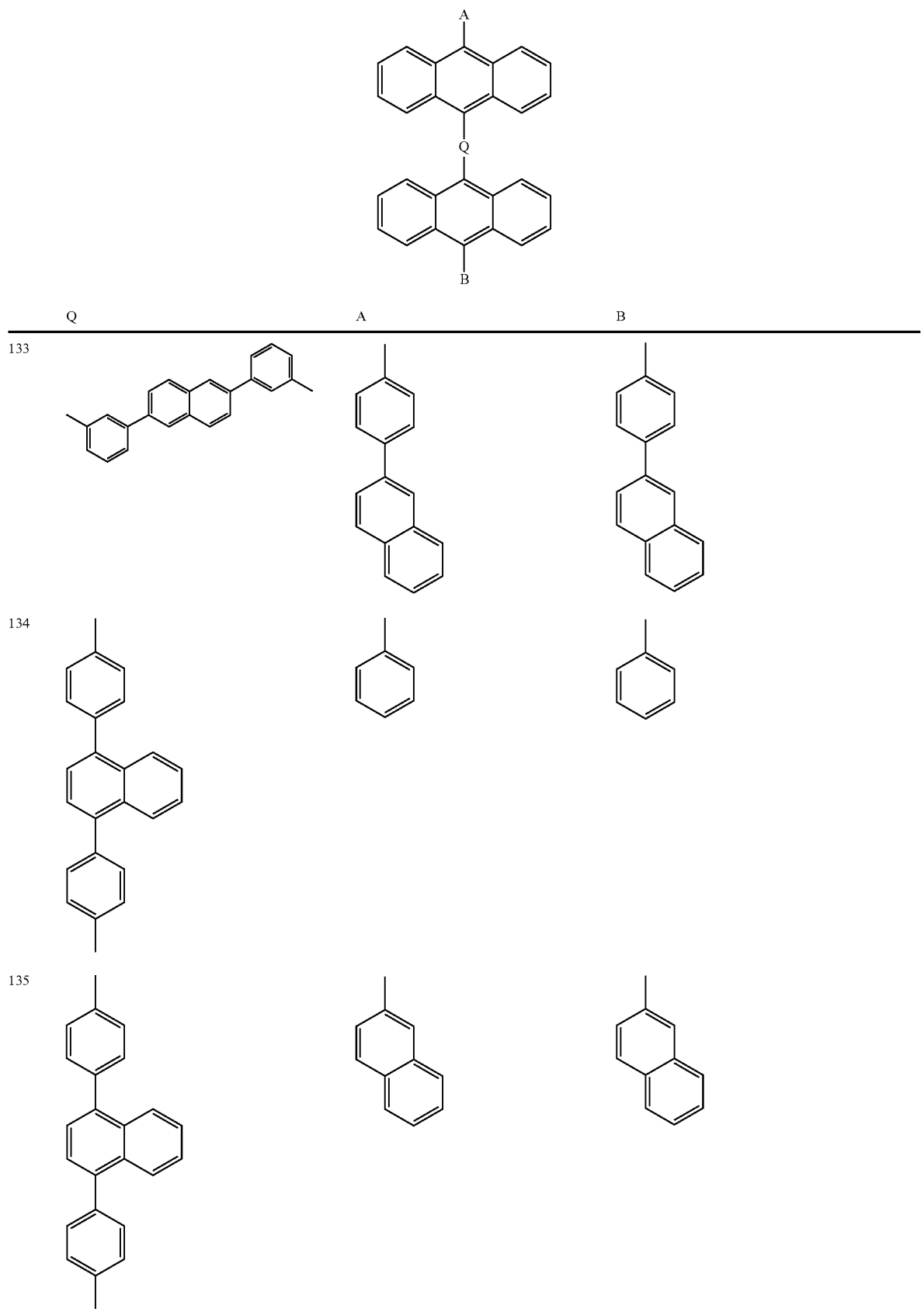

TABLE 1-continued
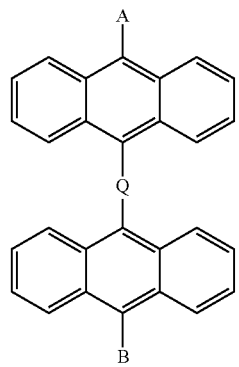
| | Q | A | B |
|---|---|---|---|
| 136 | 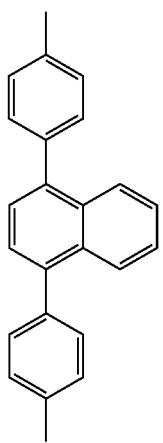 | 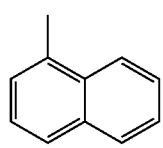 | 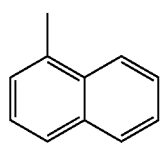 |
| 137 | 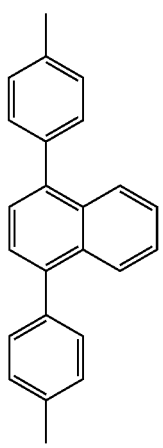 | 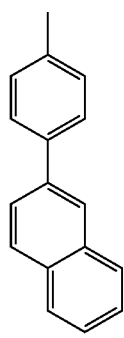 | 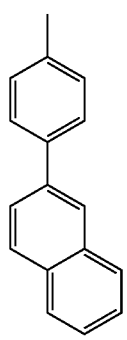 |

TABLE 1-continued

| Q | A | B |
|---|---|---|
| 138 | | |
| 139 | | |

TABLE 1-continued
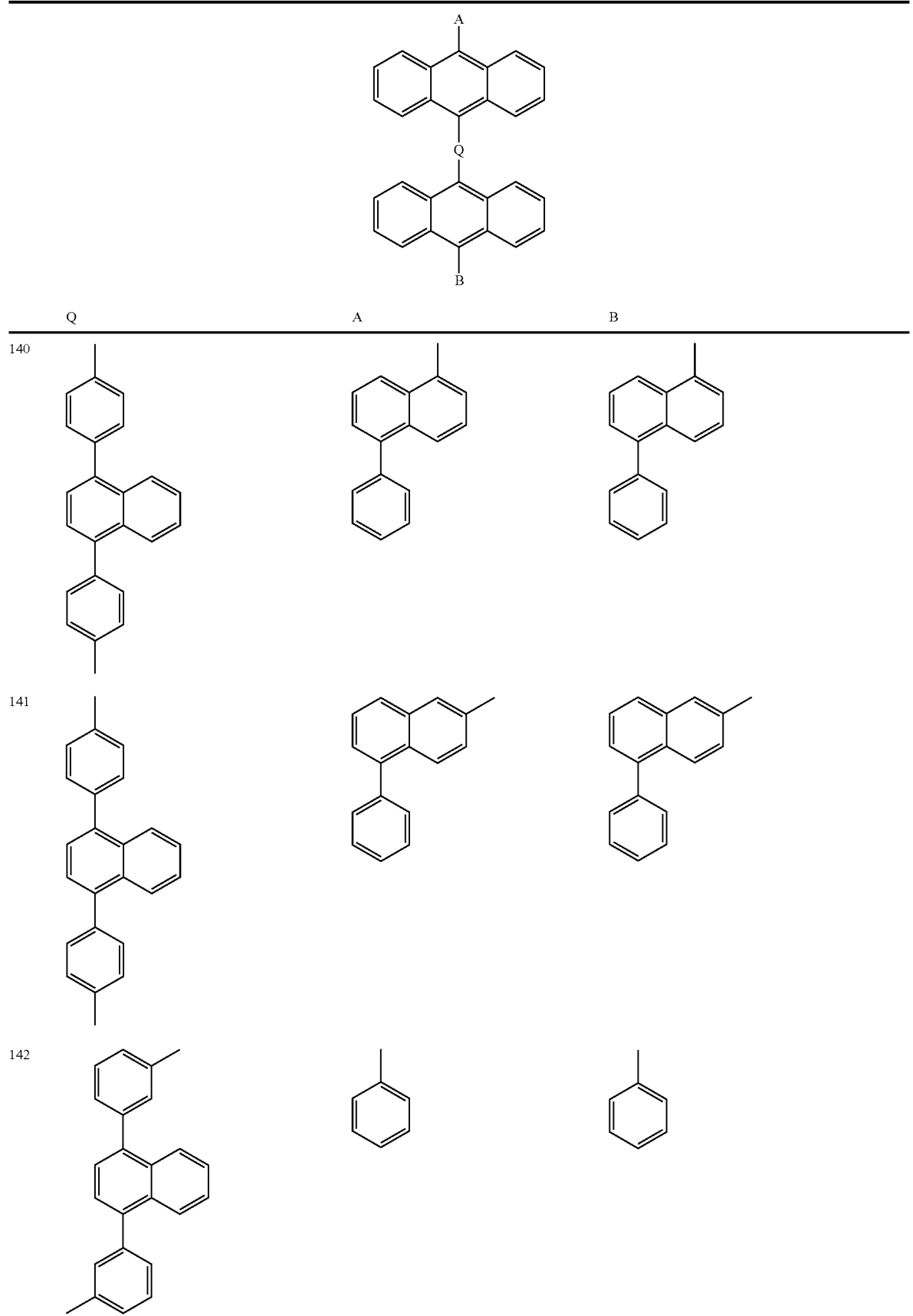

TABLE 1-continued
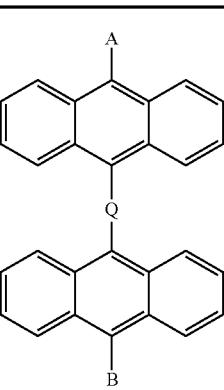
| Q | A | B |
|---|---|---|
| 143 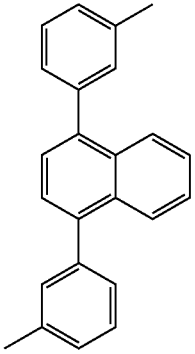 | 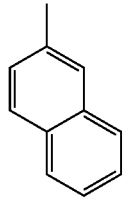 | 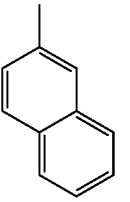 |
| 144 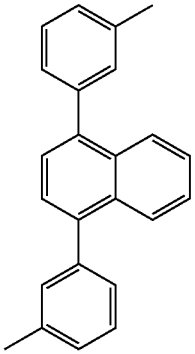 | 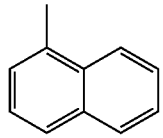 | 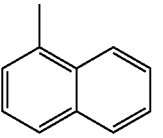 |
| 145 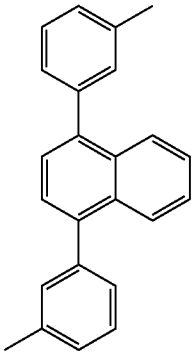 | 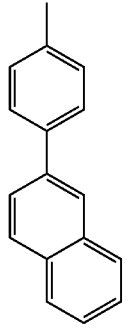 | 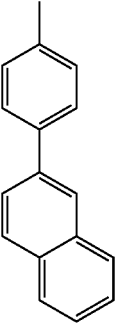 |

TABLE 1-continued

| | Q | A | B |
|---|---|---|---|
| 146 | 5-(4-methylphenyl)-6-(4-methylphenyl)naphthalene | phenyl | phenyl |
| 147 | 5-(4-methylphenyl)-6-(4-methylphenyl)naphthalene | 2-naphthyl | 2-naphthyl |
| 148 | 5-(4-methylphenyl)-6-(4-methylphenyl)naphthalene | 1-naphthyl | 1-naphthyl |

TABLE 1-continued
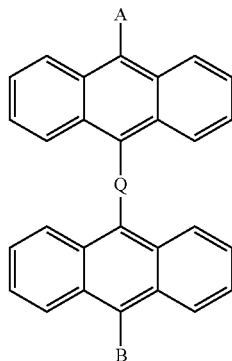
| | Q | A | B |
|---|---|---|---|
| 149 | 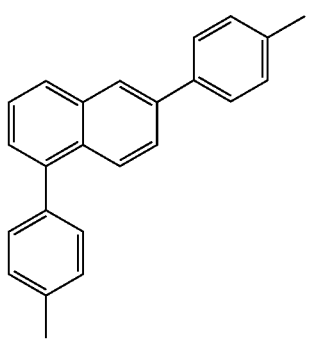 | 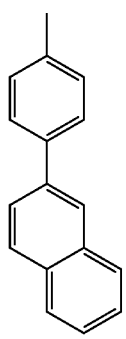 | 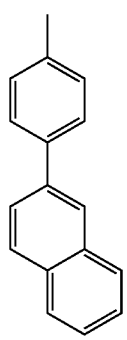 |
| 150 | 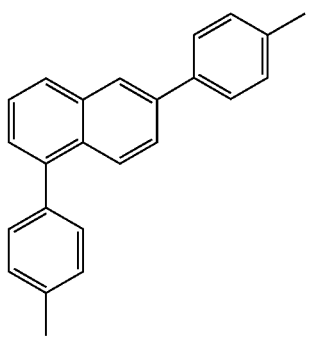 | 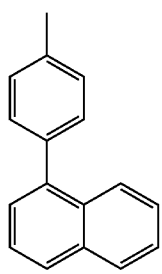 | 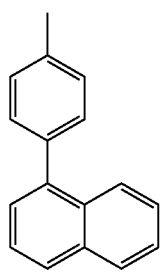 |
| 151 | 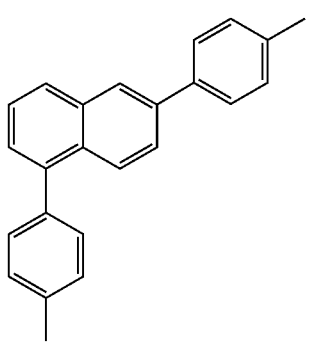 | 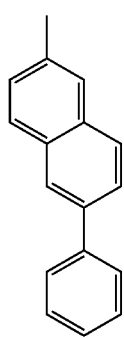 | 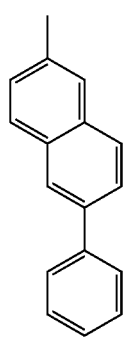 |

TABLE 1-continued
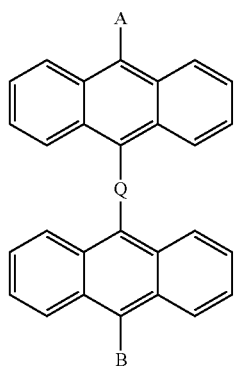
| | Q | A | B |
|---|---|---|---|
| 152 | 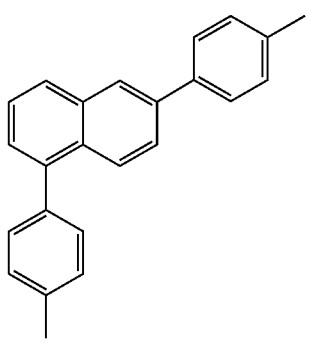 | 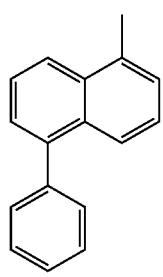 | 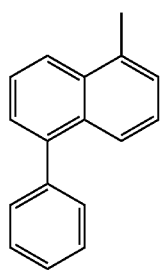 |
| 153 | 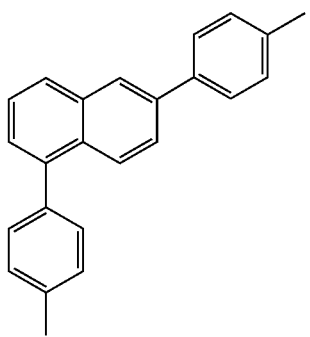 | 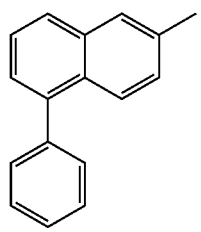 | 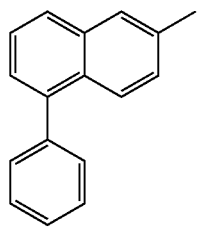 |
| 154 | 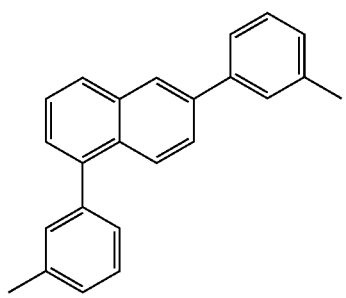 | 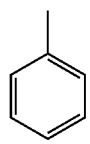 | 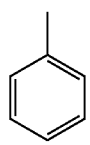 |

TABLE 1-continued
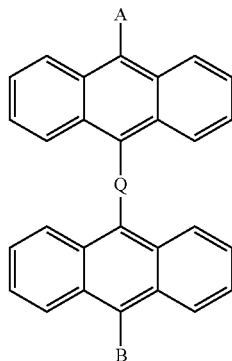
| Q | A | B |
|---|---|---|
| 155 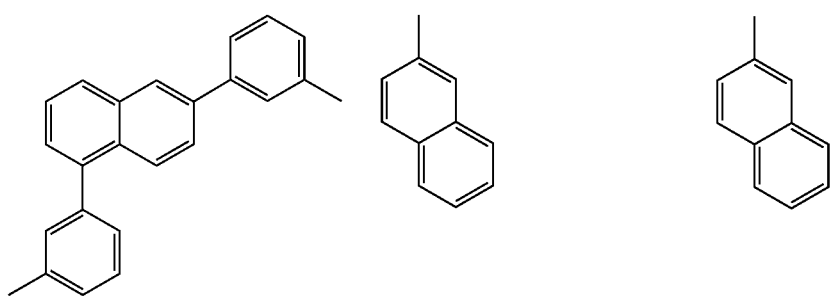 | | |
| 156 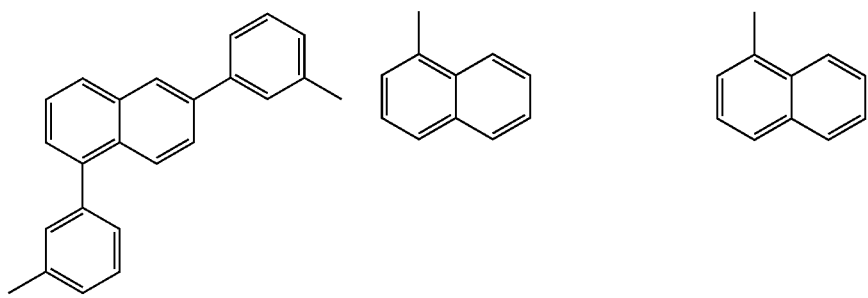 | | |
| 157 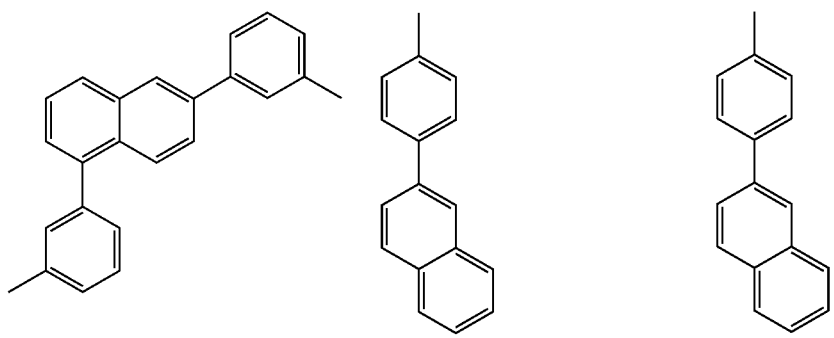 | | |

TABLE 1-continued
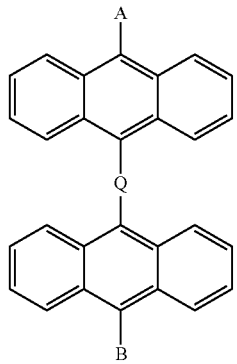
| | Q | A | B |
|---|---|---|---|
| 158 | 3-(p-tolyl)-1-(p-tolyl)naphthalen-2-yl | phenyl | phenyl |
| 159 | 3-(p-tolyl)-1-(p-tolyl)naphthalen-2-yl | naphthalen-2-yl | naphthalen-2-yl |
| 160 | 3-(p-tolyl)-1-(p-tolyl)naphthalen-2-yl | naphthalen-1-yl | naphthalen-1-yl |

TABLE 1-continued
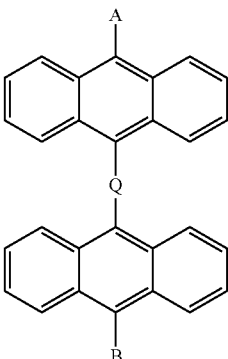
| | Q | A | B |
|---|---|---|---|
| 161 | 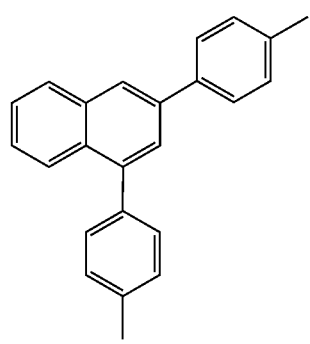 | 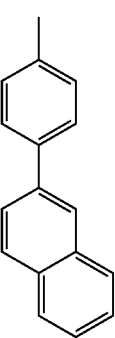 | 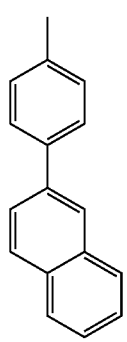 |
| 162 | 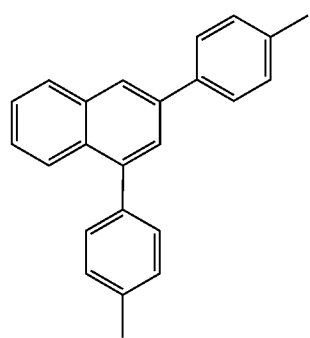 | 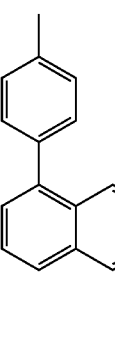 | 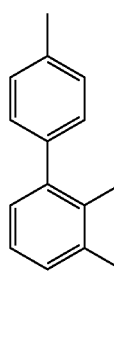 |
| 163 | 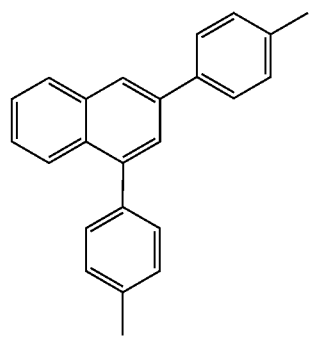 | 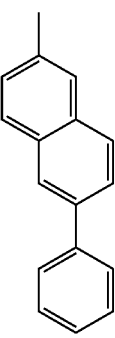 | 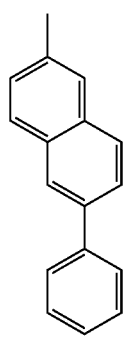 |

TABLE 1-continued
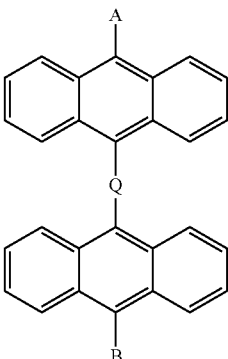
| | Q | A | B |
|---|---|---|---|
| 164 | 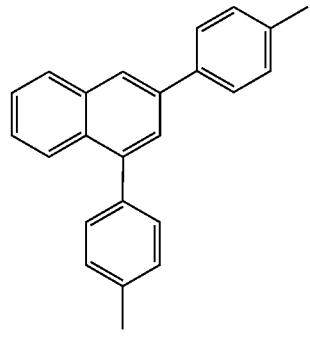 | 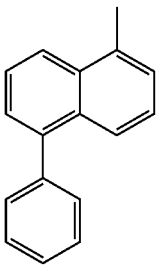 | 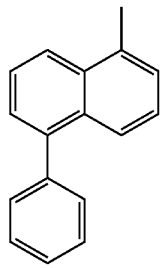 |
| 165 | 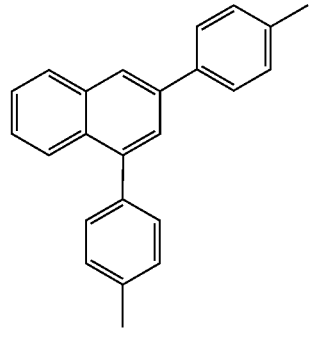 | 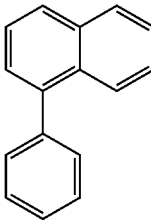 | 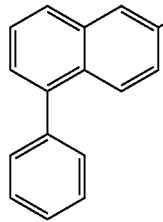 |
| 166 | 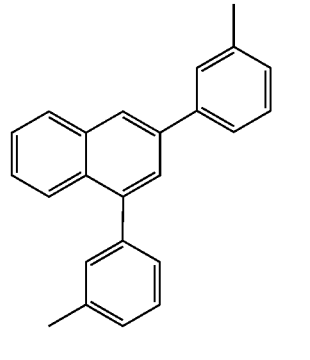 | 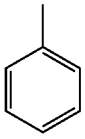 | 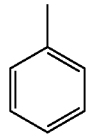 |

TABLE 1-continued
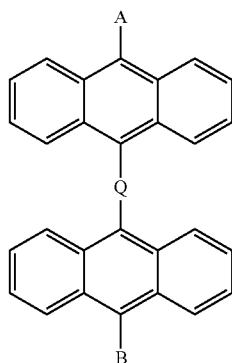
| Q | A | B |
|---|---|---|
| 167 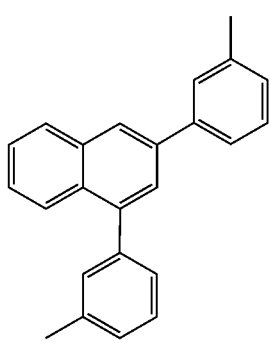 | 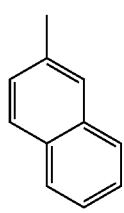 | 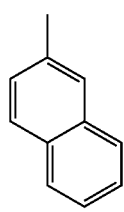 |
| 168 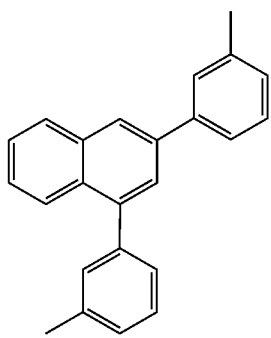 | 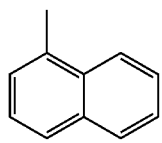 | 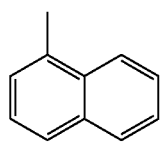 |
| 169 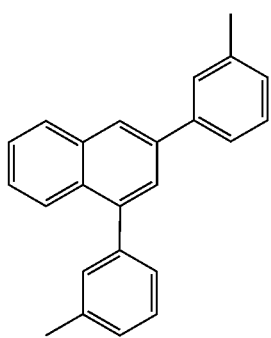 | 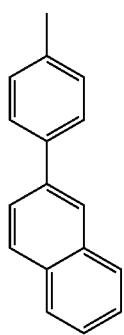 | 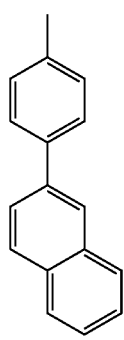 |

TABLE 1-continued
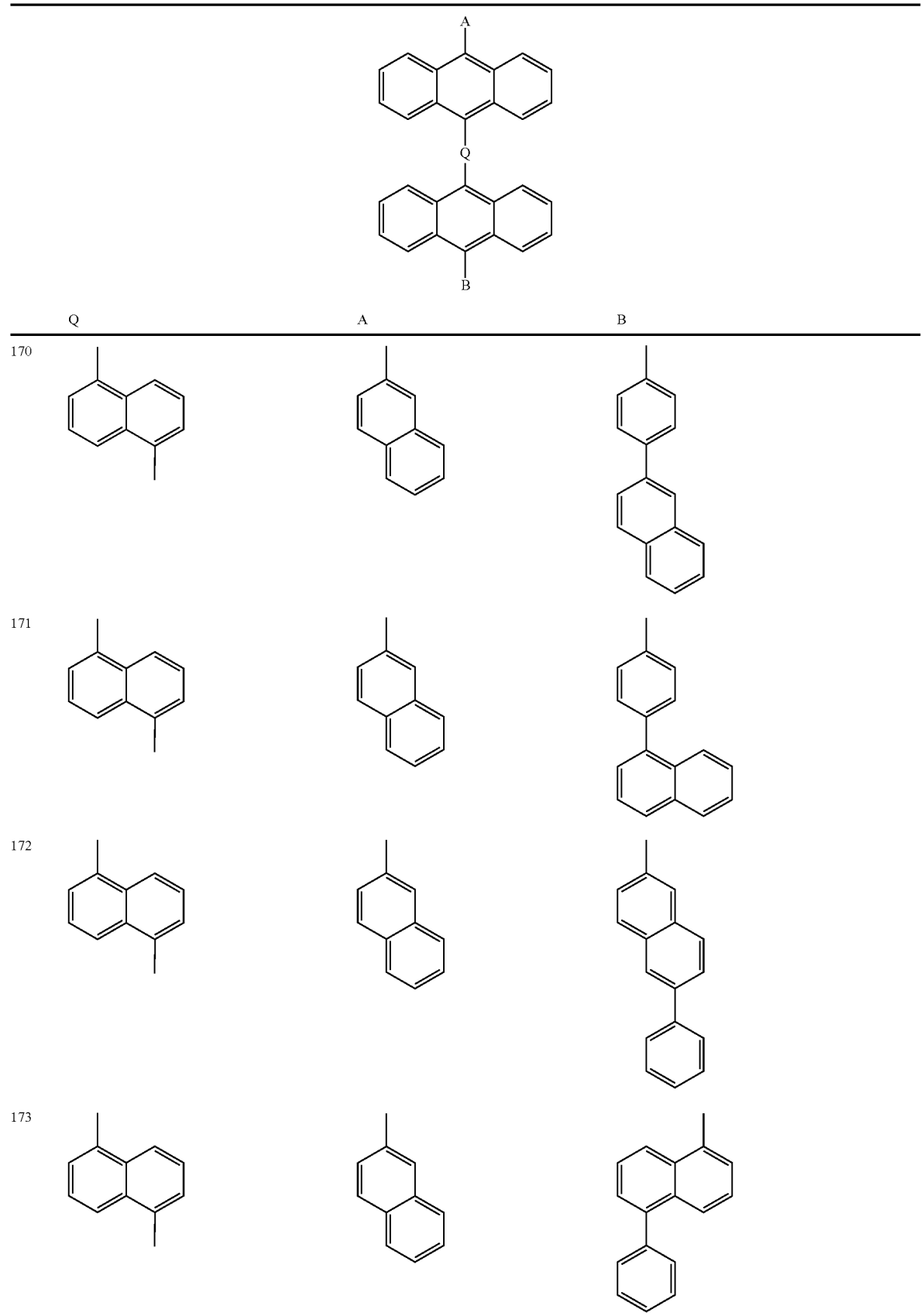

TABLE 1-continued
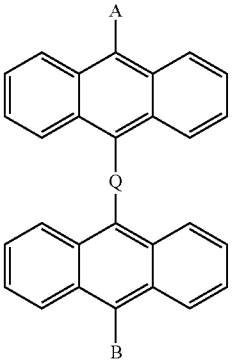
| Q | A | B |
|---|---|---|
| 174 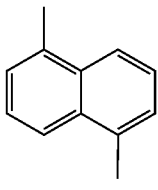 | 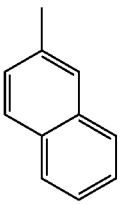 | 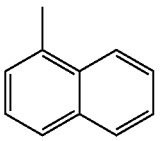 |
| 175 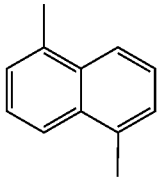 | 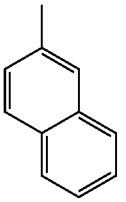 | 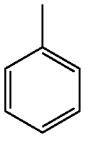 |
| 176 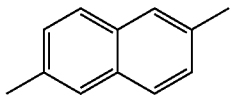 | 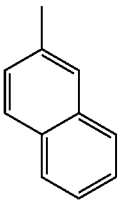 | 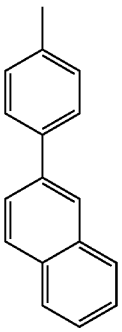 |
| 177 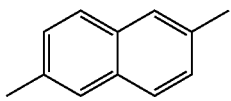 | 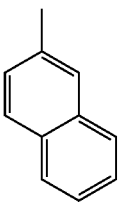 | 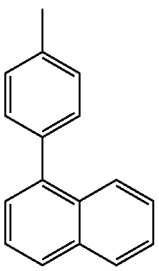 |

TABLE 1-continued
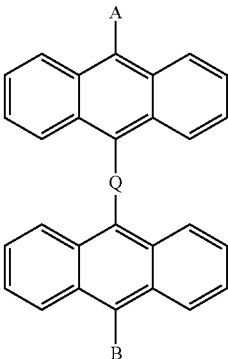
| | Q | A | B |
|---|---|---|---|
| 178 | 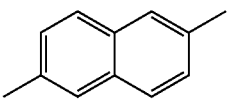 | 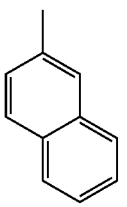 | 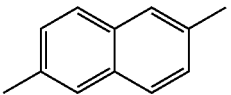 |
| 179 | 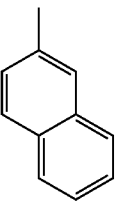 | 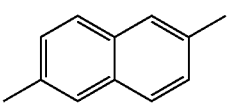 | 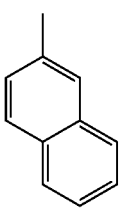 |
| 180 | 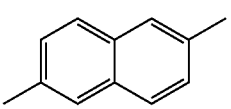 | 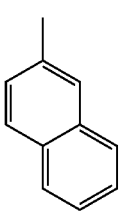 |  |
| 181 |  |  |  |

TABLE 1-continued
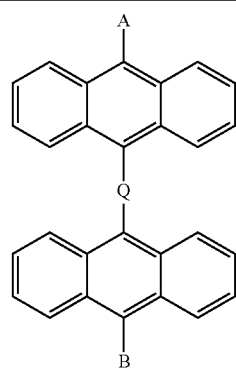
| | Q | A | B |
|---|---|---|---|
| 182 | 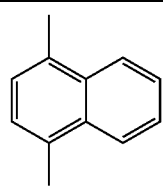 | 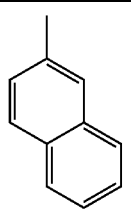 | 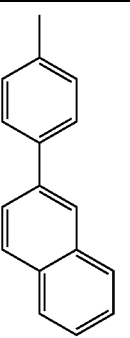 |
| 183 | 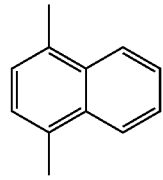 | 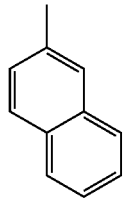 | 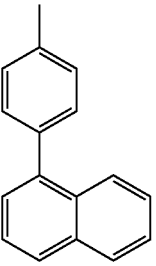 |
| 184 | 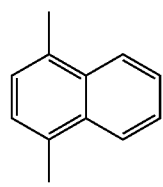 | 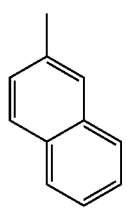 | 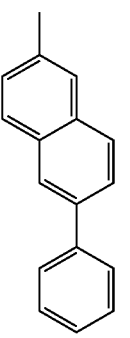 |
| 185 | 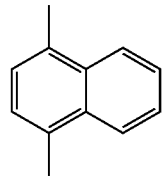 | 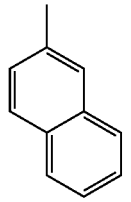 | 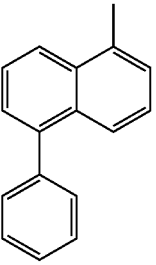 |

TABLE 1-continued
| | Q | A | B |
|---|---|---|---|
| 186 | 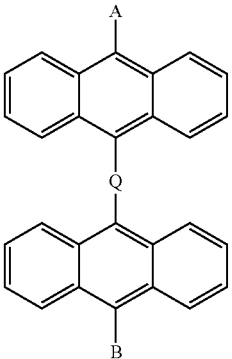 | 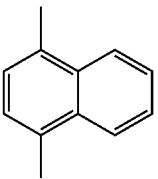 | 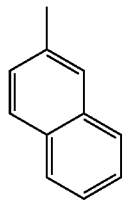 |
| 187 | 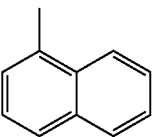 | 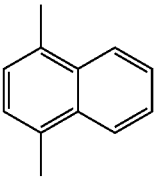 | 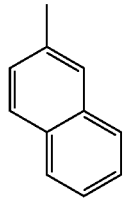 |
| 188 | 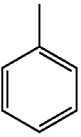 | 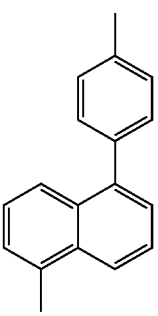 | 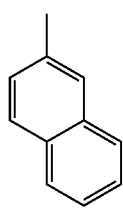 |
| 189 | 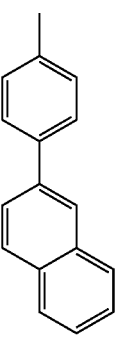 | 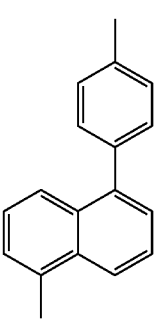 | 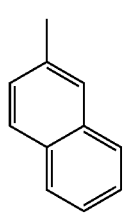 |

TABLE 1-continued
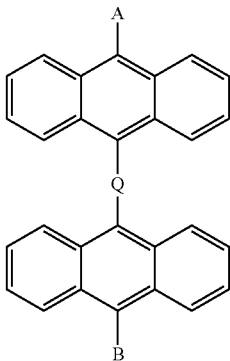
| Q | A | B |
|---|---|---|
| 190 | | |
| 191 | | |
| 192 | | |

TABLE 1-continued
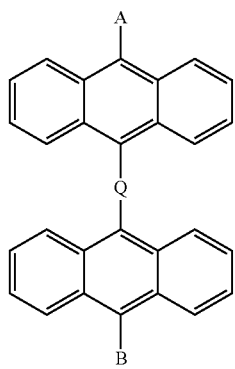
| Q | A | B |
|---|---|---|
| 193 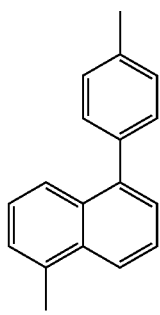 | 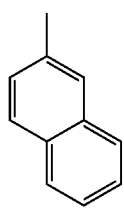 | 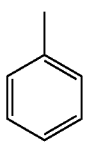 |
| 194 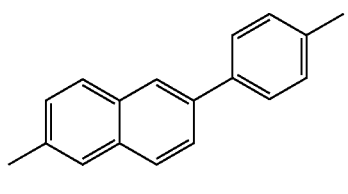 | 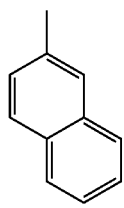 | 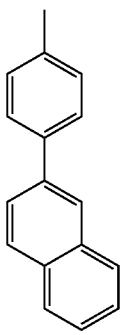 |
| 195 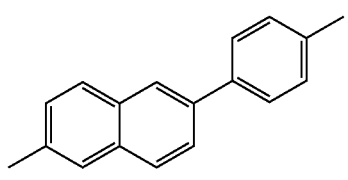 | 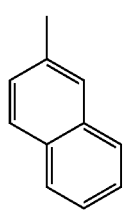 | 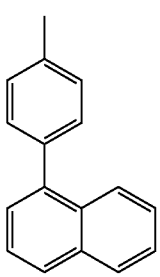 |

TABLE 1-continued
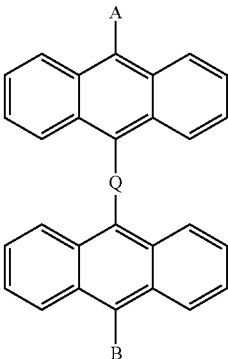
| | Q | A | B |
|---|---|---|---|
| 196 | 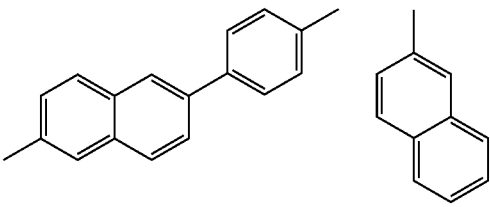 | 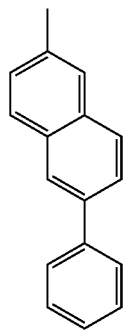 | 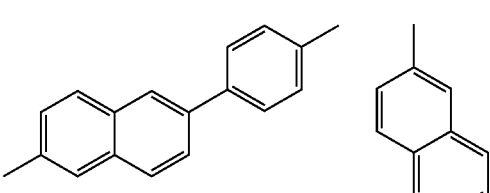 |
| 197 | 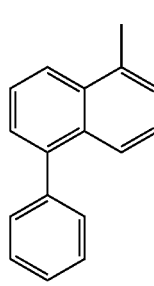 | 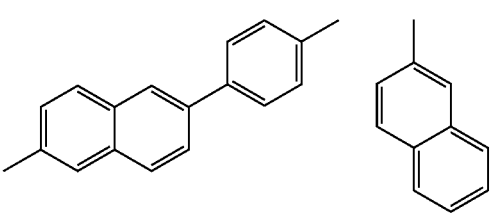 | 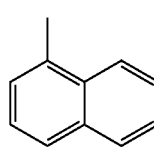 |
| 198 | 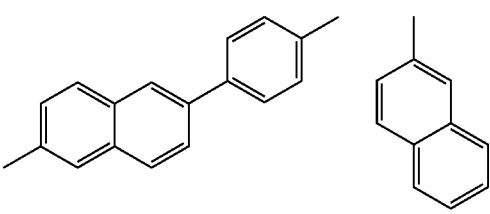 | 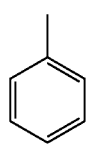 |  |
| 199 |  |  |  |

TABLE 1-continued
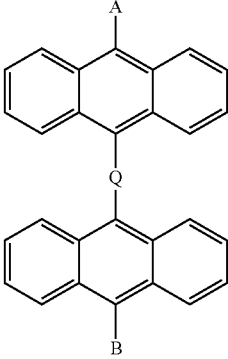
| Q | A | B |
|---|---|---|
| 200 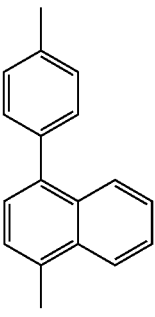 | 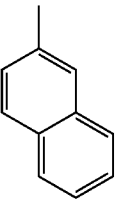 | 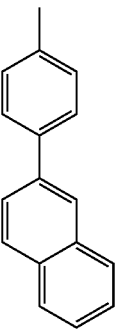 |
| 201 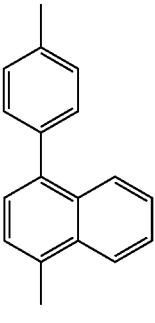 | 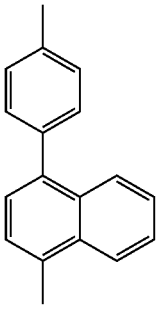 | 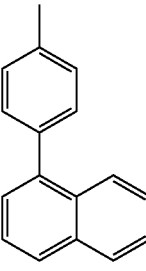 |
| 202 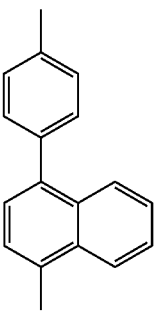 | 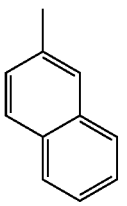 | 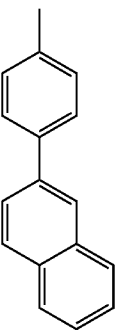 |

TABLE 1-continued
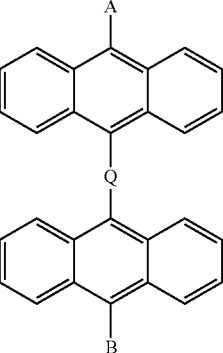
| | Q | A | B |
|---|---|---|---|
| 203 | 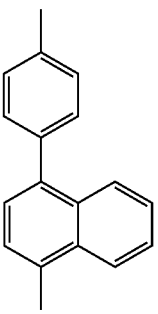 | 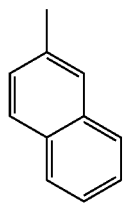 | 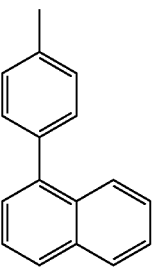 |
| 204 | 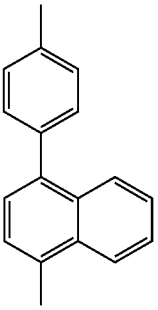 | 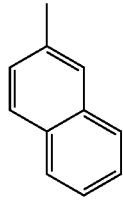 | 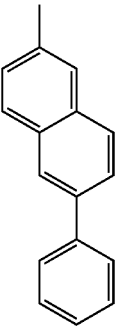 |
| 205 | 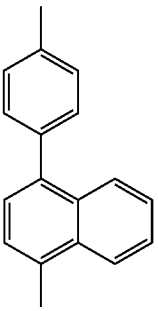 | 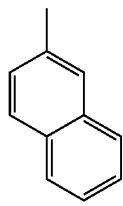 | 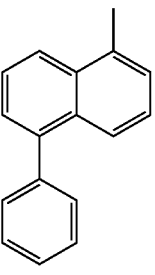 |

TABLE 1-continued
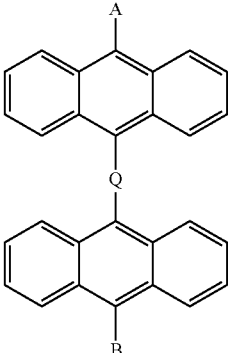
| Q | A | B |
|---|---|---|
| 206 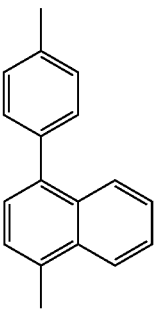 | 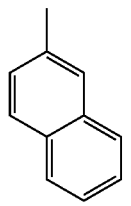 | 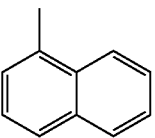 |
| 207 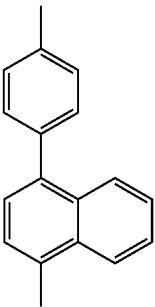 | 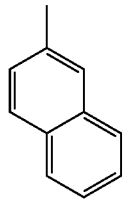 | 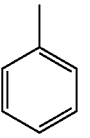 |
| 208 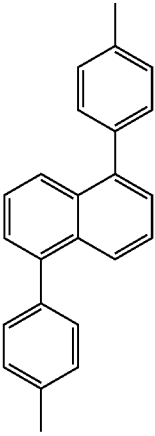 | 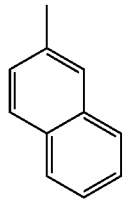 | 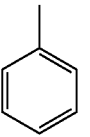 |

TABLE 1-continued
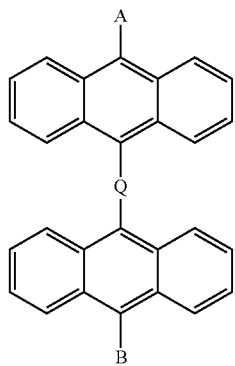
| Q | A | B |
|---|---|---|
| 209 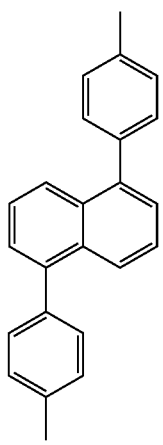 | 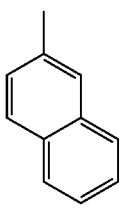 | 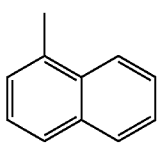 |
| 210 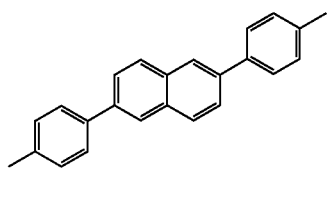 | 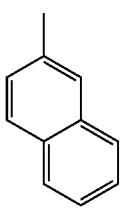 | 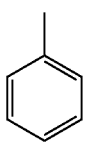 |
| 211 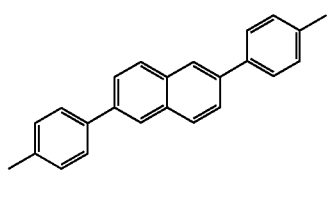 | 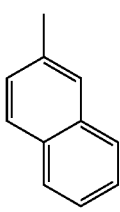 | 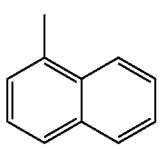 |

TABLE 1-continued
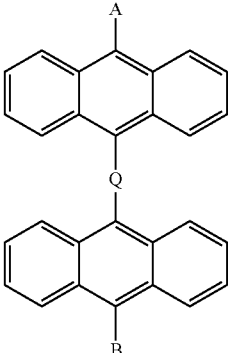
| | Q | A | B |
|---|---|---|---|
| 212 | 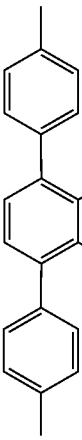 | 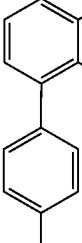 | 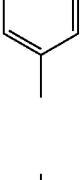 |
| 213 | 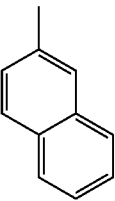 | 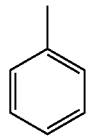 | 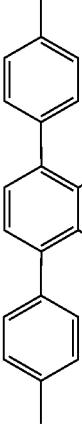 |
| 214 | 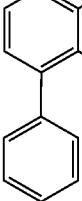 |  | 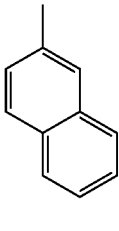 |

TABLE 1-continued
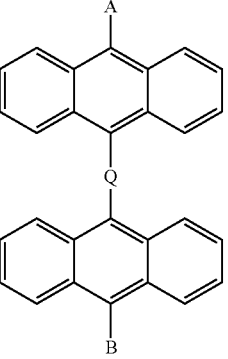

TABLE 1-continued
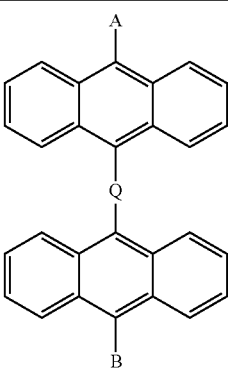
| | Q | A | B |
|---|---|---|---|
| 219 | 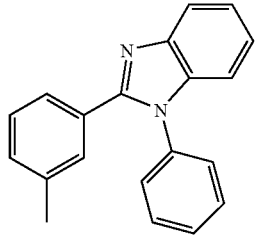 | 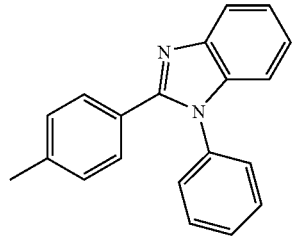 | 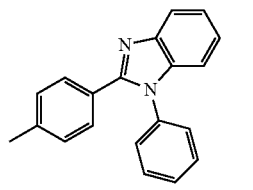 |
| 220 | 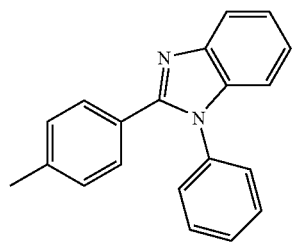 | 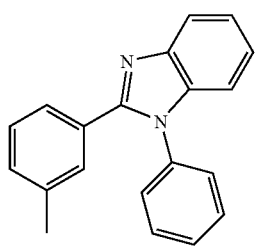 | 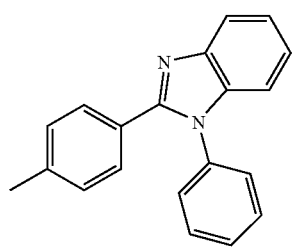 |
| 221 | 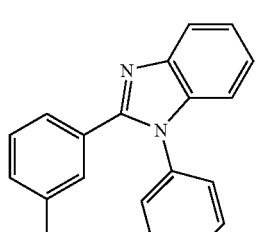 | 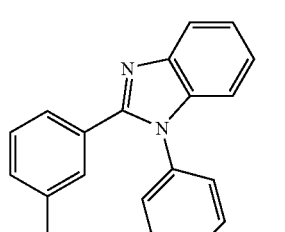 | 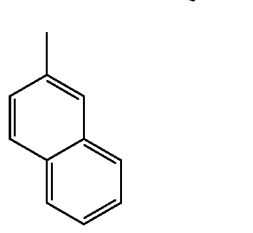 |
| 222 | | | |
| 223 | | | 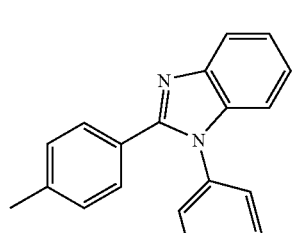 |

TABLE 1-continued
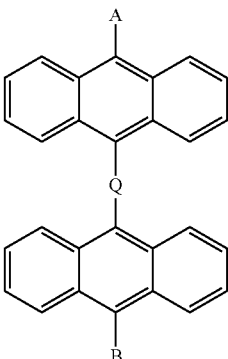
| | Q | A | B |
|---|---|---|---|
| 224 | 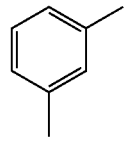 | 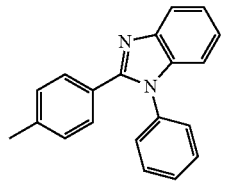 | 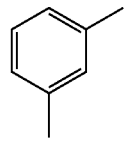 |
| 225 | 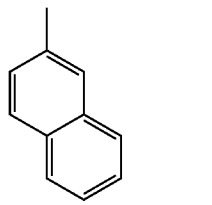 | 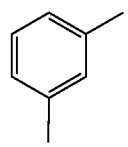 | 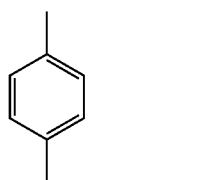 |
| 226 | 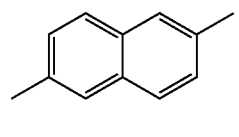 | 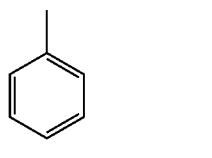 | |

TABLE 1-continued
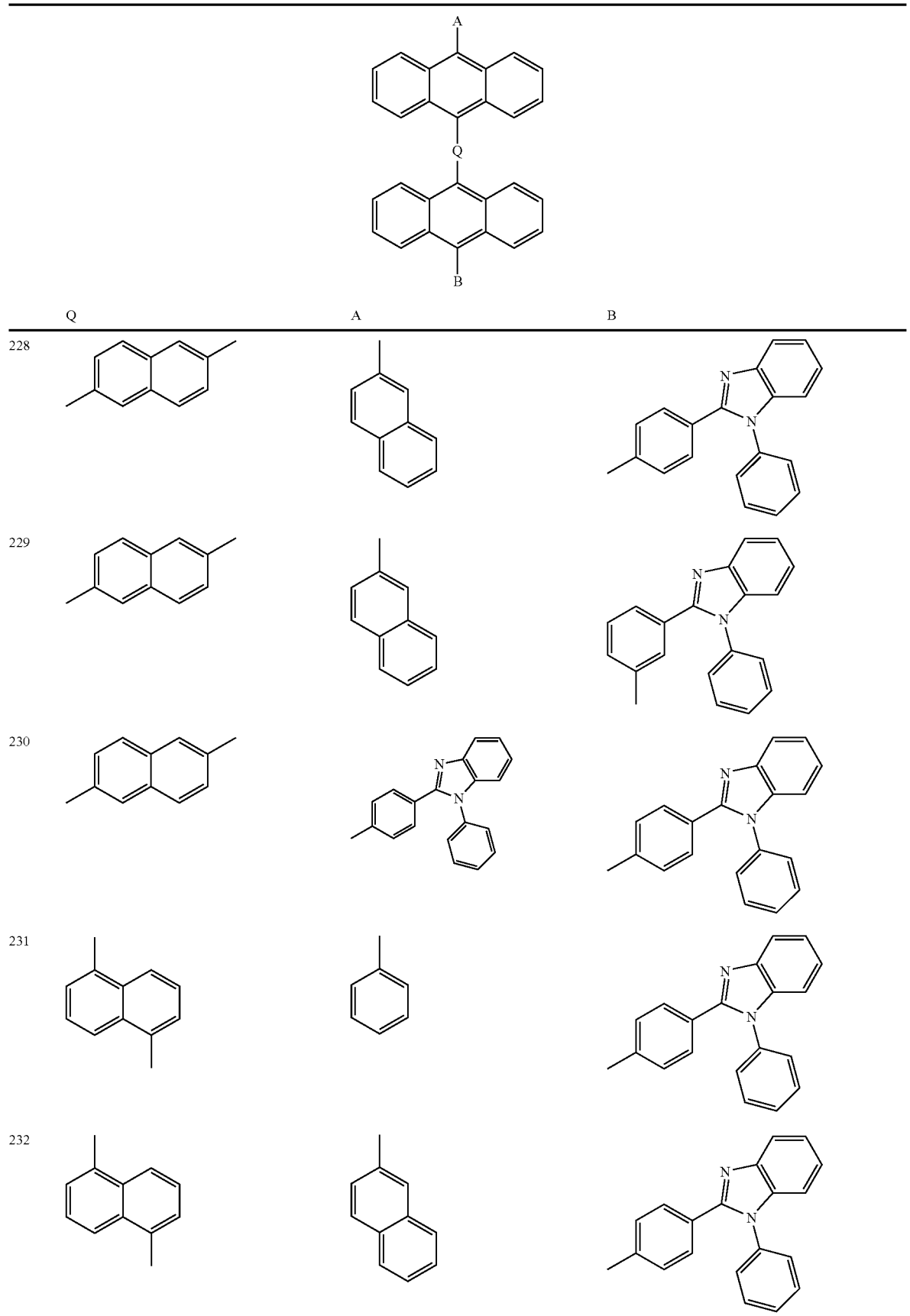

TABLE 1-continued
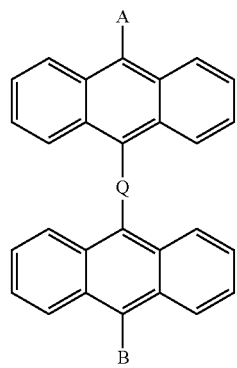
| Q | A | B |
|---|---|---|
| 233 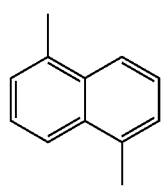 | 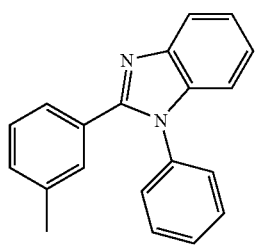 | 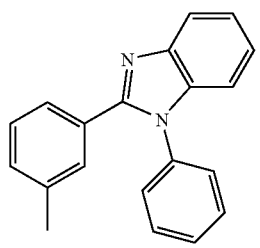 |
| 234 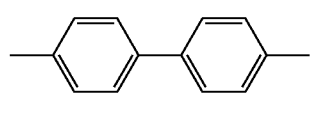 | 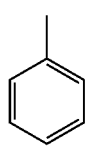 | 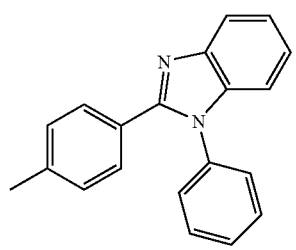 |
| 235 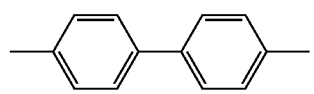 | 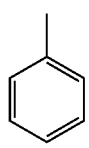 | 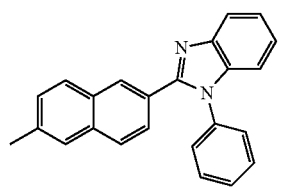 |
| 236 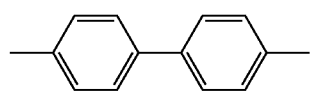 | 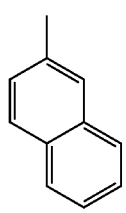 | 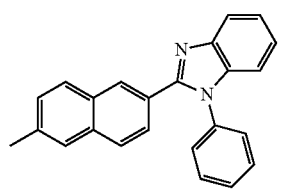 |
| 237 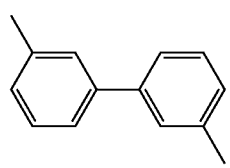 | 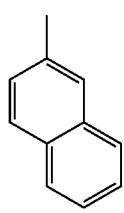 | 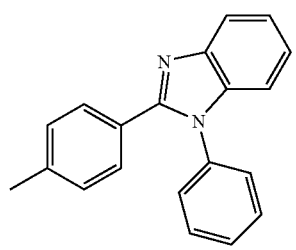 |

Further, the present invention provides a method for preparing the anthracene derivative represented by the formula 1.

The anthracene derivative according to the present invention can be prepared by subjecting a dibromoaryl compound and an anthracene boronic acid to a Suzuki coupling reaction in the presence of a Pd catalyst.

Further, the present invention provides an organic electronic device using the compound of the formula 1.

The organic electronic device of the present invention can be prepared by usual methods and materials for preparing an organic electronic device, except that the above-described compounds are used to form at least one organic material layer. Hereinbelow, the organic light emitting device will be exemplified.

The above-described compounds can function alone as a light emitting material, as well as a light emitting host with an appropriate light emitting dopant or a light emitting dopant with an appropriate light emitting host in an organic electronic device.

In another embodiment of the present invention, the organic light emitting device may be the structure that comprises a first electrode, a second electrode and organic material layers interposed therebetween, and can be prepared by usual methods and materials for preparing an organic light emitting device, except that the above-described compound according to the present invention is used to form at least one of the organic material layers in an organic light emitting device. The structure of the organic light emitting device of the present invention can be that as shown FIG. 1.

For example, the organic light emitting device according to the present invention can be prepared by depositing a metal, a metal oxide having conductivity or an alloy thereof on a substrate using a PVD (physical vapor deposition) process such as sputtering and e-beam evaporation to form an anode; forming an organic material layer comprising a hole injecting layer, a hole transporting layer, a light emitting layer and an electron transporting layer on the anode; and depositing a material, which can be used as a cathode, thereon. Alternatively, an organic light emitting device can be prepared by sequentially depositing a cathode material, an organic material layer, and an anode material on a substrate, thus preparing the above-described organic light emitting device having a reverse structure.

The organic material layer may be multi layer structure including a hole injecting layer a hole transporting layer, a light emitting layer and electron transporting layer, but is not limited thereto, it may be a single layer structure. Further, the organic material layer can be prepared to have a fewer number of layers, using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to the organic material layers. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide, such as ZnO:Al and $SnO_2$:Sb; conductive polymers such as poly(3-methylthiophene), poly[3,4-(ethylene-1,2-dioxy)thiophene] (PEDT), polypyrrole and polyaniline, but are not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin and lead, and an alloy thereof; and multilayered materials such as LiF/Al and $LiO_2$/Al, but are not limited thereto.

The hole injecting material is a material facilitating hole injection from an anode at low voltage. The HOMO (highest occupied molecular orbital) of the hole injecting material is preferably located between the work function of the anode materials and the HOMO level of its neighboring organic material layer. Specific examples of the hole injecting material include organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is a material having high hole mobility, which can transfer holes from the anode or the hole injecting layer toward the light emitting layer. Specific examples thereof include organic materials of arylamine series, conductive polymers and block copolymers having both of the conjugated portions and the non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; spiro compounds; and polyfluorene and rubrene compounds, but are not limited thereto.

The electron transporting material is suitably a material having high electron mobility, which can easily receive electrons from the cathode and then transfer them to the light emitting layer. Specific examples thereof include an Alq complex of an 8-hydroxyquinoline aluminum complex; complexes including $Alq_3$; organic radical compounds; and hydroxyflavone-metal complexes, but are not limited thereto.

The organic light emitting device according to the present invention may be of a front-sided, back-sided or double-sided light emission according to the materials used.

The compound according to the invention can also function in an organic electronic device including an organic solar cell, an organic photoconductor and an organic transistor, according to a principle similar to that applied to the organic light emitting device.

[Mode for Invention]

Hereinafter, preferable Examples are provided for the purpose of making the present invention more understandable. As such, Examples are provided for illustrating the Examples, but the scope of the invention is not limited thereto.

EXAMPLE 1

Preparation of Compound 1

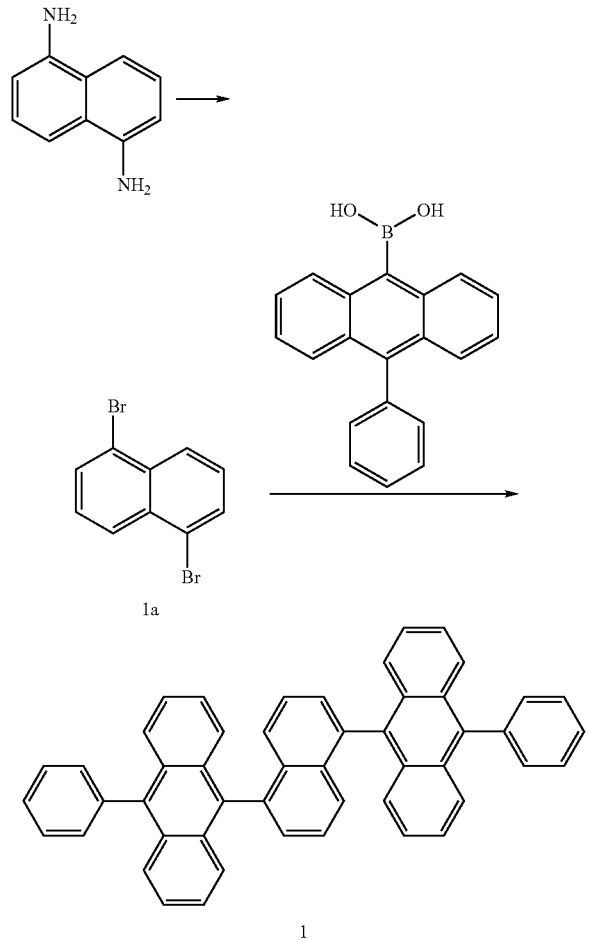

1-A. Preparation of Compound 1a

Under cooling, 1,5-diaminonaphthalene (12 g, 75.9 mmol) was dissolved in H$_2$O (300 mL) and conc. sulfuric acid (20 mL). To the solution, NaNO$_2$ dissolved in H$_2$O (300 mL) was added dropwise slowly and stirred at 0° C. for 45 minutes. After filtering the mixture, CuBr$_2$ (30 g, 52.3 mmol), HBr (48%, 450 mL) and H$_2$O (450 mL) were added to the filtrate. The solution was stirred at 0° C. for 1 hour and at room temperature for 2 hours and then stirred again at 70° C. for 30 minutes. The organic layer was separated with benzene, dried over sodium sulfate, and distilled under reduced pressure. The residue was purified by column chromatography to prepare compound 1a (5.9 g, 27%). MS [M]=286

1-B. Preparation of Compound 1

Under N$_2$ atmosphere, a compound 1a, 1,5-dibromonaphthalene (1 g, 3.5 mmol), 10-phenylanthracene-9-boronic acid (2.62 g, 8.75 mmol), and Pd(PPh$_3$)$_4$ (0.3 g, 0.3 mmol) were added to a 2 M aqueous solution of potassium carbonate (70 mL) and THF (150 mL). The mixture was refluxed under stirring for about 24 hours. After completing the reaction, the mixture was cooled to normal temperature. The organic layer was separated from the reaction mixture, and filtered to obtain a solid. The solid was recrystallized from THF and EtOH to prepare a compound 1 (1.7 g, 77%). MS [M]=632

EXAMPLE 2

Preparation of Compound 2

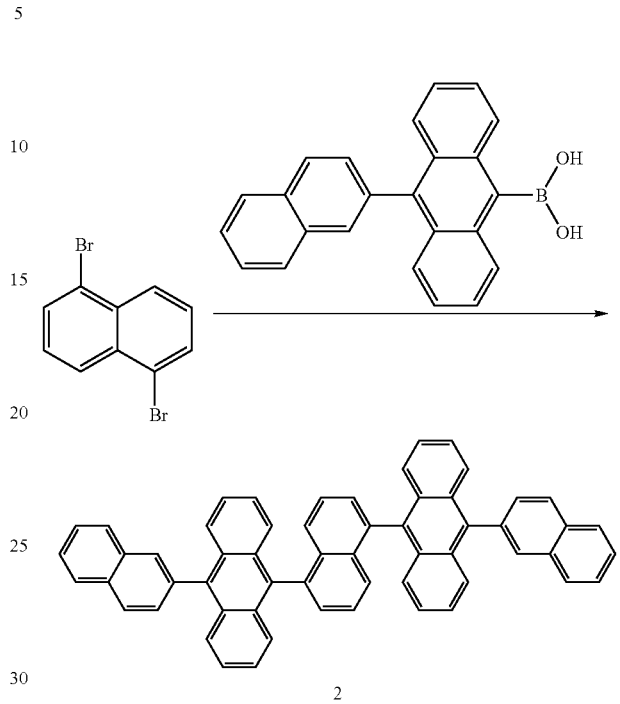

Under N$_2$ atmosphere, 1,5-dibromonaphthalene (1.5 g, 5.2 mmol), 10-(2-naphthyl)anthracene-9-boronic acid (4.0 g, 11.4 mmol) and Pd(PPh$_3$)$_4$ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, and filtered to obtain a solid. The solid was recrystallized from THF and EtOH to prepare a compound 2 (2.5 g, 66%). MS [M+H]=733

EXAMPLE 3

Preparation of Compound 3

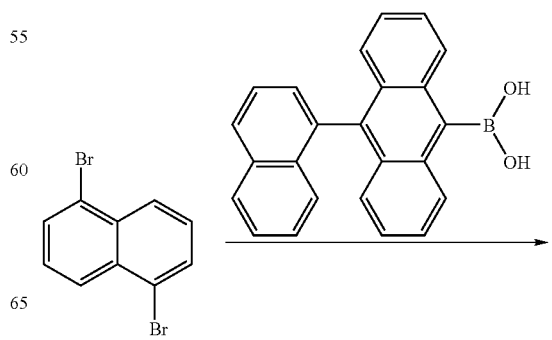

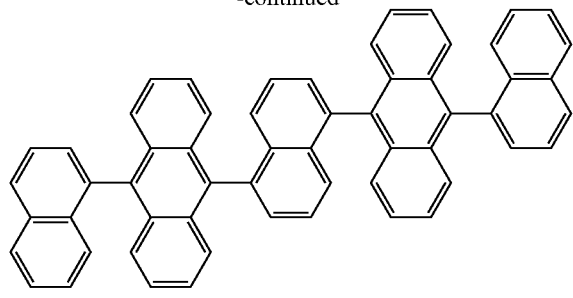

3

Under N₂ atmosphere, 1,5-dibromonaphthalene (1.5 g, 5.2 mmol), 10-(1-naphthyl)anthracene-9-boronic acid (4.0 g, 11.4 mmol), and Pd(PPh₃)₄ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, and filtered to obtain a solid. The solid was recrystallized from THF and EtOH to prepare a compound 3 (2.3 g, 63%). MS [M+H]=733

EXAMPLE 4

Preparation of Compound 4

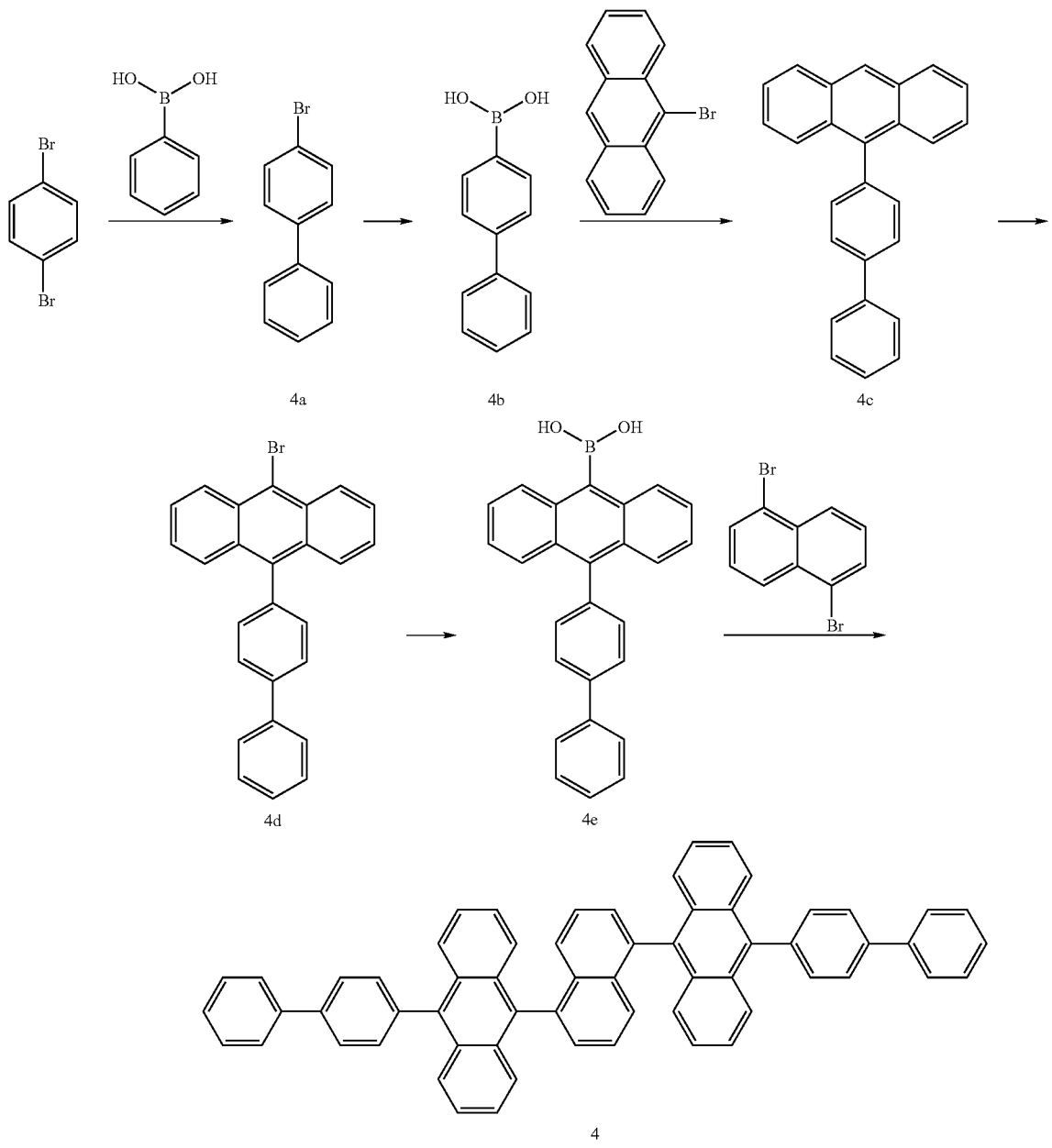

4-A. Preparation of Compound 4a

Under N₂ atmosphere, 1,4-dibromophenyl (40 g, 0.17 mol), phenyl boronic acid (20.6 g, 0.17 mol), and Pd(PPh₃)₄ (9.6 g, 8.4 mmol were added to a 2 M aqueous solution of potassium carbonate (500 mL) and THF (500 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare a compound 4a (18.4 g, 47%). MS [M]=233

4-B. Preparation of Compound 4b

Under N₂ atmosphere, to a compound 4a (18 g, 34.4 mmol), dehydrated ether (180 mL) and dehydrated toluene (180 mL) were added, and cooled to −64° C. in ice bath. A 2.5 M butyl lithium/hexane solution (24 mL) was added dropwise thereto for 30 minutes, and subjected to reaction at −64° C. for 2 hours. Boronic acid trimethyl ester (36 mL) was added dropwise thereto for 15 minutes, and then stirred at room temperature for 12 hours. After ice cooling, 2 N hydrochloric acid (140 mL) was added at 10° C. or lower and toluene (40 mL) was added. The mixture was separated, dried over magnesium sulfate, and concentrated under reduced pressure. The residue was recrystallized from EtOH to prepare a compound 4b (7.6 g).

4-C. Preparation of Compound 4c

Under N₂ atmosphere, 9-bromoanthracene (8.2 g, 31.9 mmol), the compound 4b (7.6 g, 38.6 mmol), and Pd(PPh₃)₄ (0.7 g, 0.6 mmol) were added to a 2 M aqueous solution of potassium carbonate (300 mL) and THF (300 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was recrystallized from THF and EtOH to prepare a compound 4c (8.5 g, 81%). MS [M]=330

4-D. Preparation of Compound 4d

Under N₂ atmosphere, a compound 4c (8.0 g, 24.2 mmol) was dissolved in chloroform (150 mL). Acetic acid (150 mL) was added thereto, and Br₂ (1.3 mL, 25.4 mmol) was added dropwise at 0° C. The temperature of the mixture was raised to ambient temperature, and stirred for 5 hours. After completing the reaction, the resultant was concentrated, and recrystallized from EtOH to prepare a compound 4d (7 g, 71%). MS [M]+=408

4-E. Preparation of Compound 4e

Under N₂ atmosphere, to a compound 4d (7 g, 17.1 mmol), dehydrated ether (80 mL) and dehydrated toluene (80 mL) were added, and cooled to −64° C. in ice bath. A 2.5 M butyl lithium/hexane solution (9 mL) was added dropwise thereto for 30 minutes, and subjected to reaction at −64° C. for 2 hours. Boronic acid triisoester (12 mL) was added dropwise thereto for 15 minutes, and then stirred at room temperature for 12 hours. After ice cooling, 2 N hydrochloric acid (70 mL) was added at 10° C. or lower and toluene (30 mL) was added. The mixture was separated, dried over magnesium sulfate, and concentrated under reduced pressure. The residue was recrystallized from hexane to prepare a yellow solid. To the solid, conc. hydrochloric acid (7 mL) and tetrabutylammonium bromide (0.04 g, 0.1 mmol) were added, and dissolved in THF (100 mL). The mixture was subjected to reaction at room temperature for 12 hours. After completing the reaction, the mixture was solidified in H₂O and filtered to prepare a compound 4e (3.2 g, 50%).

4-F. Preparation of Compound 4

Under N₂ atmosphere, 1,5-dibromonaphthalene (1 g, 3.6 mmol), the compound 4e (3.0 g, 8.02 mmol) and Pd(PPh₃)₄ (0.2 g, 0.18 mmol) were added to a 2 M aqueous solution of potassium carbonate (100 mL) and anisole (100 mL). The mixture was refluxed under stirring for about 24 hours. After completing the reaction, the mixture was cooled to normal temperature. The organic layer was separated from the reaction mixture, and filtered to obtain a solid. The solid was recrystallized from THF and EtOH to prepare a compound 4 (2.0 g, 70%). MS [M]=784

EXAMPLE 5

Preparation of Compound 6

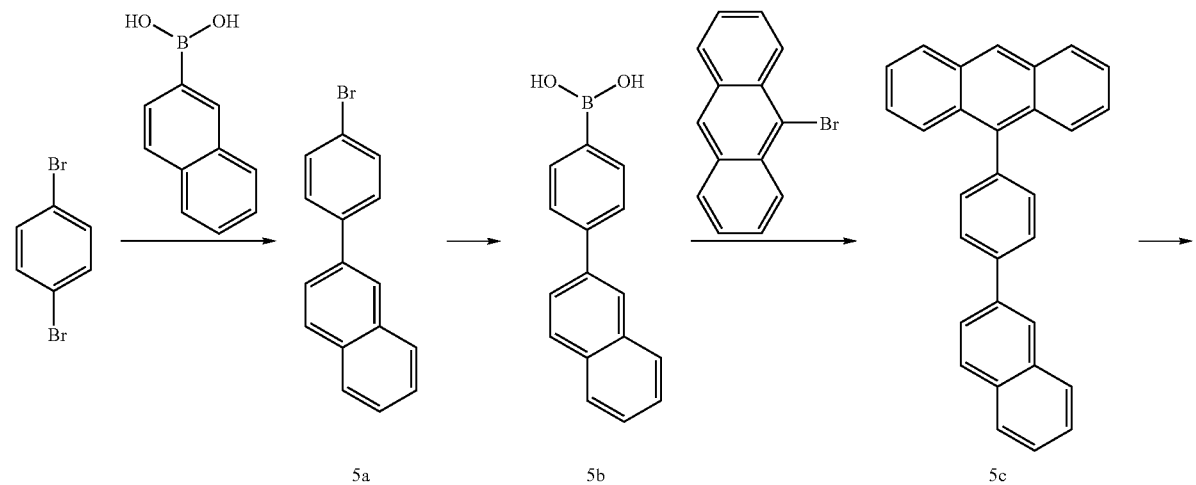

5a      5b      5c

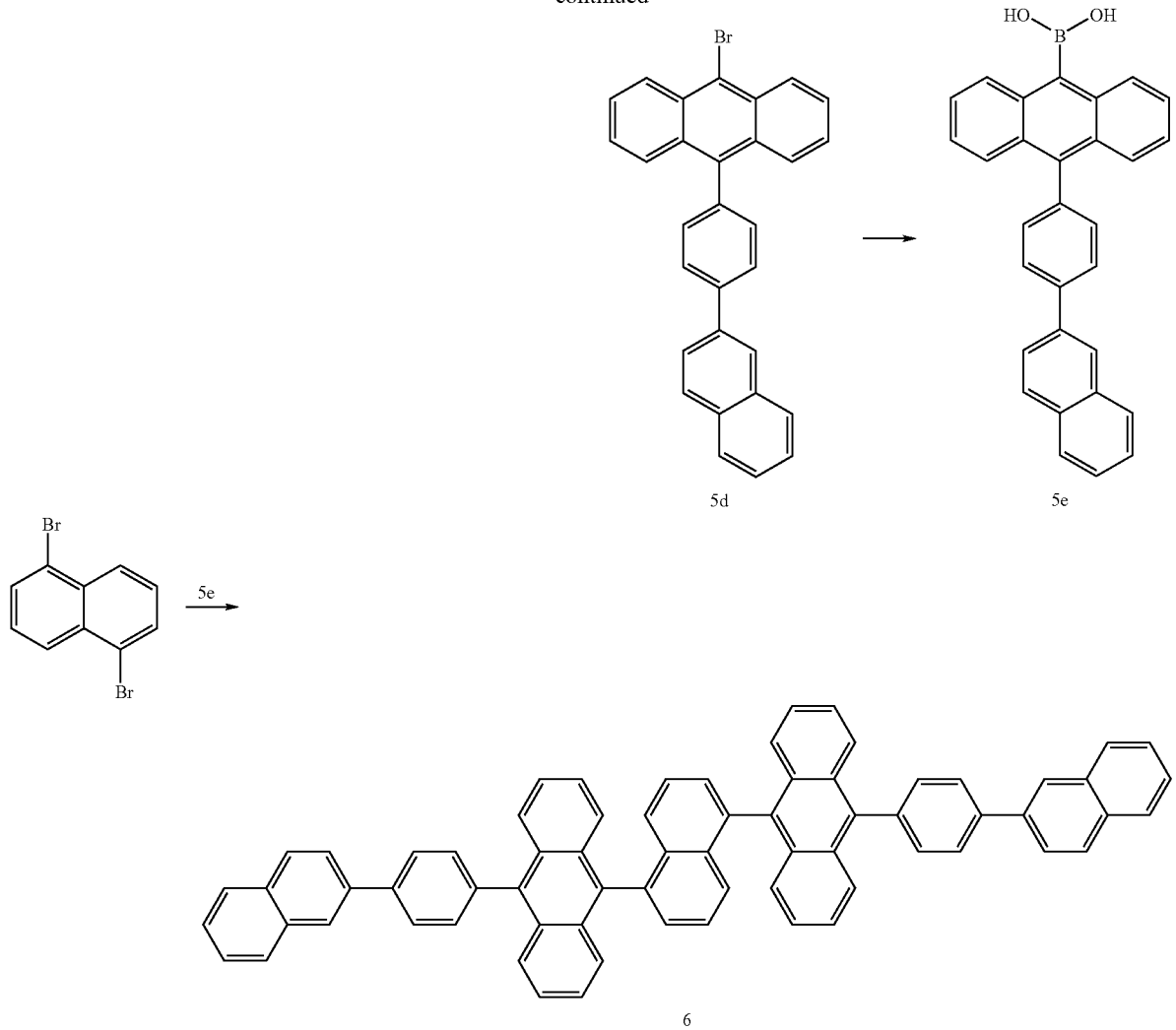

5-A. Preparation of Compound 5a

Under N₂ atmosphere, 1,4-dibromophenyl (40 g, 0.17 mol), 2-naphthyl boronic acid (29 g, 0.17 mol), and Pd(PPh₃)₄ (5.9 g, 5.1 mmol) were added to a 2 M aqueous solution of potassium carbonate (300 mL) and THF (300 mL). The mixture was refluxed under stirring for about 24 hours. After completing the reaction, the mixture was cooled to normal temperature. The organic layer was separated from the reaction mixture, dried over sodium sulfate, and distilled under reduced pressure. The residue was purified by column chromatography to prepare a compound 5a (22.6 g, 47%). MS [M]=283

5-B. Preparation of Compound 5b

Under N₂ atmosphere, to a compound 5a (20 g, 0.07 mol), dehydrated ether (100 mL) and dehydrated toluene (200 mL) were added, and cooled to −64° C. in ice bath. A 2.5 M butyl lithium/hexane solution (24 mL) was added dropwise thereto for 30 minutes, and subjected to reaction at −64° C. for 2 hours. Boronic acid trimethylester (36 mL) was added dropwise thereto for 15 minutes, and then stirred at room temperature for 12 hours. After ice cooling, 2 N hydrochloric acid (35 mL) was added at 10° C. or lower and toluene (10 mL) was added. The mixture was separated, dried over magnesium sulfate, and concentrated under reduced pressure. The residue was recrystallized from EtOH to prepare a compound 5b (8.77 g).

5-C. Preparation of Compound 5c

Under N₂ atmosphere, 9-bromoanthracene (7.34 g, 28.5 mmol), the compound 5b (8.5 g, 34.3 mmol), and Pd(PPh₃)₄ (1.0 g, 0.86 mmol) were added to a 2 M aqueous solution of potassium carbonate (200 mL) and THF (200 mL). The mixture was refluxed under stirring for about 24 hours. After completing the reaction, the mixture was cooled to normal temperature. The organic layer was separated from the reaction mixture, dried over sodium sulfate, and distilled under reduced pressure. The residue was recrystallized from THF and EtOH to prepare a compound 5c (9.2 g, 85%). MS [M]=380

5-D. Preparation of Compound 5d

Under N₂ atmosphere, a compound 5c (9 g, 23.6 mmol) was dissolved in chloroform (150 mL). Acetic acid (150 mL) was added thereto, and Br₂ (1.2 mL, 24.8 mmol) was added dropwise at 0° C. The temperature of the mixture was raised to ambient temperature, and stirred for 5 hours. After completing the reaction, the resultant was concentrated, and recrystallized from EtOH to prepare a compound 5d (7.8 g, 72%). MS [M]=459

5-E. Preparation of Compound 5e

Under $N_2$ atmosphere, to a compound 5d (7 g, 15.2 mmol)), dehydrated ether (50 mL) and dehydrated toluene (80 mL) were added, and cooled to −64° C. in ice bath. A 2.5 M butyl lithium/hexane solution (9 mL) was added dropwise thereto for 30 minutes, and subjected to reaction at −64° C. for 2 hours. Boronic acid trimethylester (12 mL) was added dropwise thereto for 15 minutes, and then stirred at room temperature for 12 hours. 2 N hydrochloric acid (70 mL) was added at 10° C. or lower and toluene (20 mL) was added. The mixture was separated, dried over magnesium sulfate, and concentrated under reduced pressure. The residue was recrystallized from hexane to prepare a yellow solid. To the solid, conc. hydrochloric acid (7 mL) and tetrabutylammonium bromide (0.04 g, 0.1 mmol) were added, and dissolved in THF (80 mL). The mixture was subjected to reaction at room temperature for 12 hours. After completing the reaction, the mixture was solidified in $H_2O$ and filtered to prepare a compound 5e (3.3 g, 51%).

5-F. Preparation of Compound 6

Under $N_2$ atmosphere, 1,5-dibromonaphthalene (0.9 g, 3.2 mmol), the compound 5e (3.0 g, 7.1 mmol), and $Pd(PPh_3)_4$ (0.17 g, 0.15 mmol) were added to a 2 M aqueous solution of potassium carbonate (50 mL) and anisole (150 mL). The mixture was refluxed under stirring for about 24 hours. After completing the reaction, the mixture was cooled to normal temperature. The organic layer was separated from the mixture and filtered to obtain a solid. The resultant was recrystallized from THF and EtOH to prepare a compound 6 (2.0 g, 72%). MS [M]=884.

EXAMPLE 6

Preparation of Compound 9

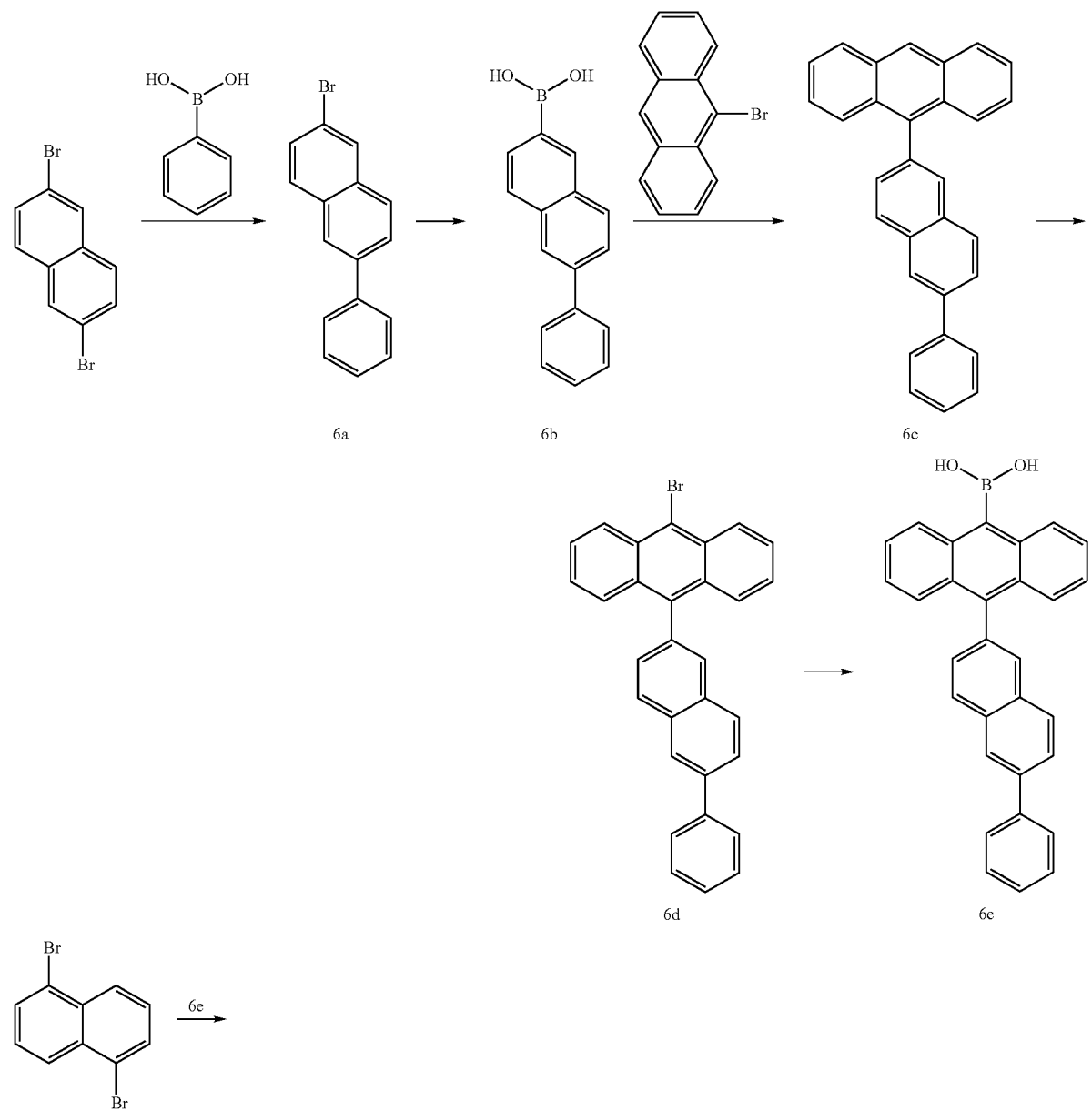

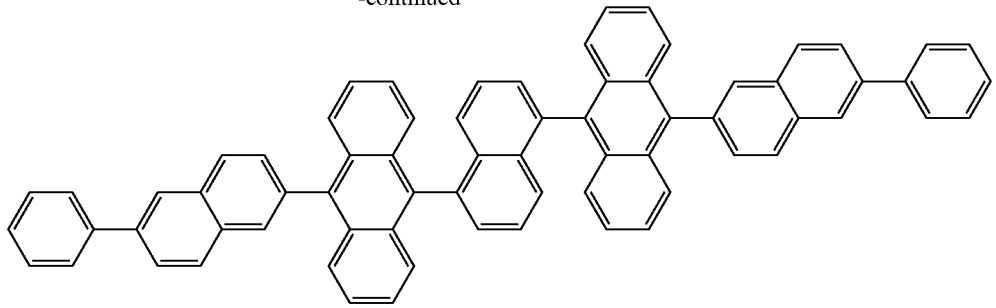

9

6-A. Preparation of Compound 6a

Under N₂ atmosphere, 2,6-dibromonaphthalene (40 g, 0.14 mol), phenyl boronic acid (17 g, 0.14 mol), and Pd(PPh₃)₄ (4.9 g, 4.2 mmol) were added to a 2 M aqueous solution of potassium carbonate (50 mL) and THF (300 mL). The mixture was refluxed under stirring for about 24 hours. After completing the reaction, the mixture was cooled to normal temperature. The organic layer was separated from the reaction mixture, dried over sodium sulfate, and distilled under reduced pressure. The residue was purified by column chromatography to prepare a compound 6a (22 g, 55%). MS [M]=283

6-B. Preparation of Compound 6b

Under N₂ atmosphere, to a compound 6a (20 g, 70.6 mmol), dehydrated ether (70 mL) and dehydrated toluene (200 mL) were added, and cooled to −64° C. in ice bath. A 2.5 M butyl lithium/hexane solution (24 mL) was added dropwise thereto for 30 minutes, and subjected to reaction at −64° C. for 2 hours. Boronic acid trimethylester (18 mL) was added dropwise thereto for 15 minutes, and then stirred at room temperature for 12 hours. After ice cooling, 2 N hydrochloric acid (500 mL) was added, and stirred for 24 hours. The mixture was separated, dried over magnesium sulfate, and concentrated under reduced pressure. The residue was recrystallized from EtOH to prepare a compound 6b (8.9 g, 51%).

6-C. Preparation of Compound 6c

Under N₂ atmosphere, 9-bromoanthracene (7.34 g, 28.5 mmol), the compound 6b (8.5 g, 34.3 mmol), and Pd(PPh₃)₄ (1.0 g, 0.86 mmol) were added to a 2 M aqueous solution of potassium carbonate (200 mL) and THF (200 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was recrystallized from THF and EtOH to prepare a compound 6c (9.2 g, 85%). MS [M]=380

6-D. Preparation of Compound 6d

Under N₂ atmosphere, a compound 6c (9 g, 23.6 mmol) was dissolved in chloroform (150 mL). Acetic acid (150 mL) was added thereto, and Br₂ (1.2 mL, 24.8 mmol) was added dropwise at 0° C. The temperature of the mixture was raised to ambient temperature, and stirred for 5 hours. After completing the reaction, the resultant was concentrated, and recrystallized from EtOH to prepare a compound 6d (7.8 g, 72%). MS [M]+=459

6-E. Preparation of Compound 6e

Under N₂ atmosphere, to a compound 6d (7 g, 15.2 mmol), dehydrated ether (50 mL) and dehydrated toluene (150 mL) were added, and cooled to −64° C. in ice bath. A 2.5 M butyl lithium/hexane solution (9 mL) was added dropwise thereto for 30 minutes, and subjected to reaction at −64° C. for 2 hours. Boronic acid triisoester (12 mL) was added dropwise thereto for 15 minutes, and then stirred at room temperature for 12 hours. After ice cooling, 2 N hydrochloric acid (70 mL) was added, and toluene (20 mL) was added. The mixture was separated, dried over magnesium sulfate, and concentrated under reduced pressure. The residue was recrystallized from hexane to prepare a yellow solid. To the solid, conc. hydrochloric acid (7 mL) and tetrabutylammonium bromide (0.04 g, 0.1 mmol) were added, and dissolved in THF (80 mL). The mixture was subjected to reaction at room temperature for 12 hours. After completing the reaction, the mixture was solidified in H₂O and filtered to prepare a compound 6e (3.3 g, 51%).

6-F. Preparation of Compound 9

Under N₂ atmosphere, 1,5-dibromonaphthalene (0.9 g, 3.2 mmol), the compound 6e (3.0 g, 7.1 mmol), and Pd(PPh₃)₄ (0.17 g, 0.15 mmol) were added to a 2 M aqueous solution of potassium carbonate (50 mL) and anisole (150 mL). The mixture was refluxed under stirring for about 24 hours. After completing the reaction, the mixture was cooled to normal temperature. The organic layer was separated from the reaction mixture, and filtered to obtain a solid. The solid was recrystallized from THF and EtOH to prepare a compound 9 (2.0 g, 72%). MS [M]=884

EXAMPLE 7

Preparation of Compound 17

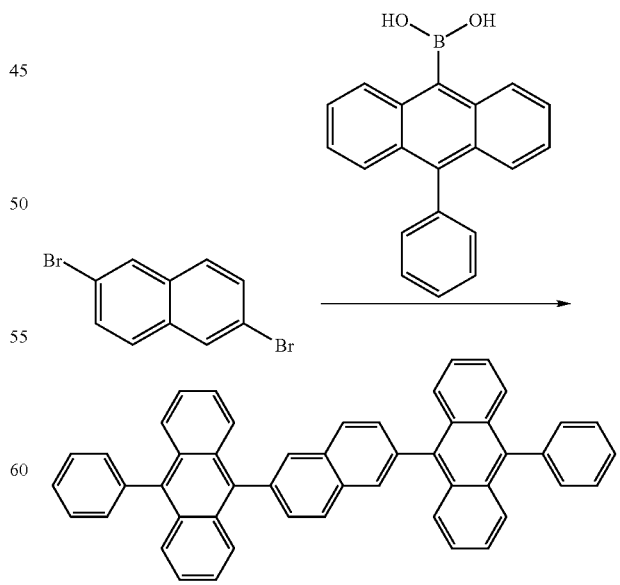

17

Under N₂ atmosphere, 2,6-dibromonaphthalene (1 g, 3.5 mmol), 10-phenylanthracene-9-boronic acid (2.62 g, 8.75 mmol), and Pd(PPh₃)₄ (0.3 g, 0.3 mmol) were added to a 2 M aqueous solution of potassium carbonate (70 mL) and THF (150 mL). The mixture was refluxed under stirring for about 24 hours. After completing the reaction, the mixture was cooled to normal temperature. The organic layer was separated from the reaction mixture, and filtered to obtain a solid. The solid was recrystallized from THF and EtOH to prepare a compound 17 (1.7 g, 77%). MS [M]=632.

EXAMPLE 8

Preparation of Compound 18

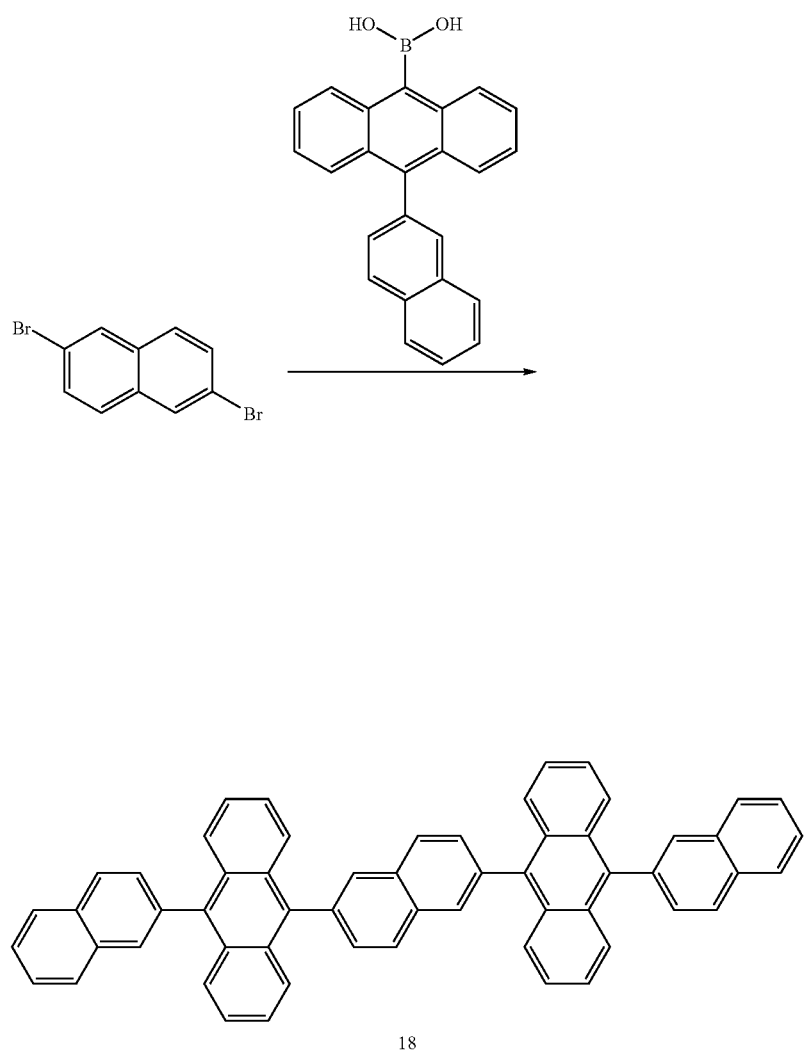

Under N₂ atmosphere, 2,6-dibromonaphthalene (1.5 g, 5.2 mmol), 10-(2-naphthyl) anthracene-9-boronic acid (4.0 g, 11.4 mmol), and Pd(PPh₃)₄ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, and filtered to obtain a solid. The solid was recrystallized from THF and EtOH to prepare a compound 18 (2.5 g, 66%). MS [M+H]=733.

EXAMPLE 9

Preparation of Compound 19

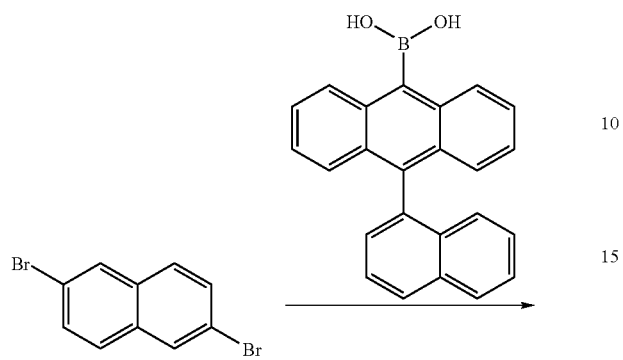

Under $N_2$ atmosphere, 2,6-dibromonaphthalene (1.5 g, 5.2 mmol), 10-(1-naphthyl) anthracene-9-boronic acid (4.0 g, 11.4 mmol), and $Pd(PPh_3)_4$ (0.3 g, 0.26 mmol) were added to a 2 M aqueous solution of potassium carbonate (80 mL) and anisole (100 mL). The mixture was refluxed under stirring for about 12 hours. After completing the reaction, the mixture was cooled to normal temperature. The organic layer was separated from the reaction mixture, and filtered to obtain a solid. The solid was recrystallized from THF and EtOH to prepare a compound 19 (2.9 g, 78%). MS [M+H]=733

EXAMPLE 10

Preparation of Compound 22

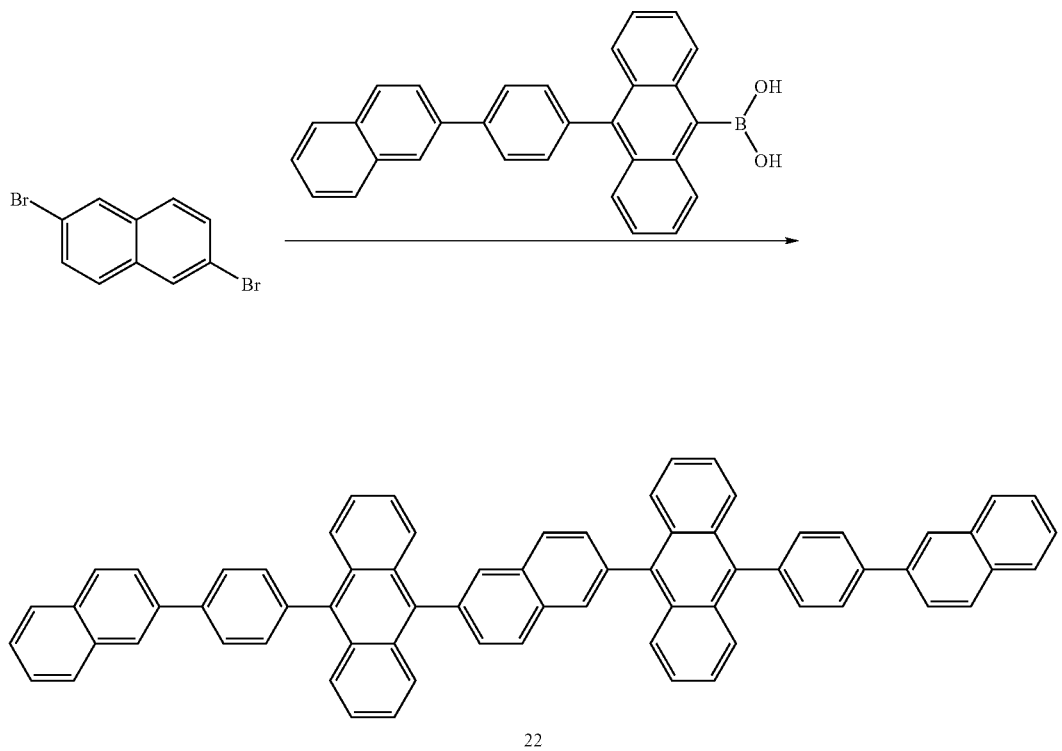

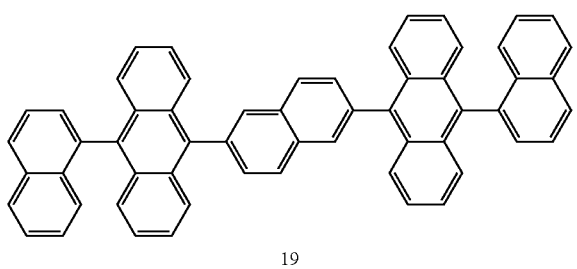

Under $N_2$ atmosphere, 2,6-dibromonaphthalene (1 g, 3.5 mmol), the compound 5e (3.27 g, 7.69 mmol) prepared in 5-E of Example 5, and $Pd(PPh_3)_4$ (0.2 g, 0.18 mmol) were added to a 2 M aqueous solution of potassium carbonate (100 mL) and anisole (100 mL). The mixture was refluxed under stirring for about 24 hours. After completing the reaction, the mixture was cooled to normal temperature. The organic layer was separated from the reaction mixture, and filtered to obtain a solid. The solid was recrystallized from THF and EtOH to prepare a compound 22 (2.3 g, 75%). MS [M]=884

EXAMPLE 11

Preparation of Compound 24

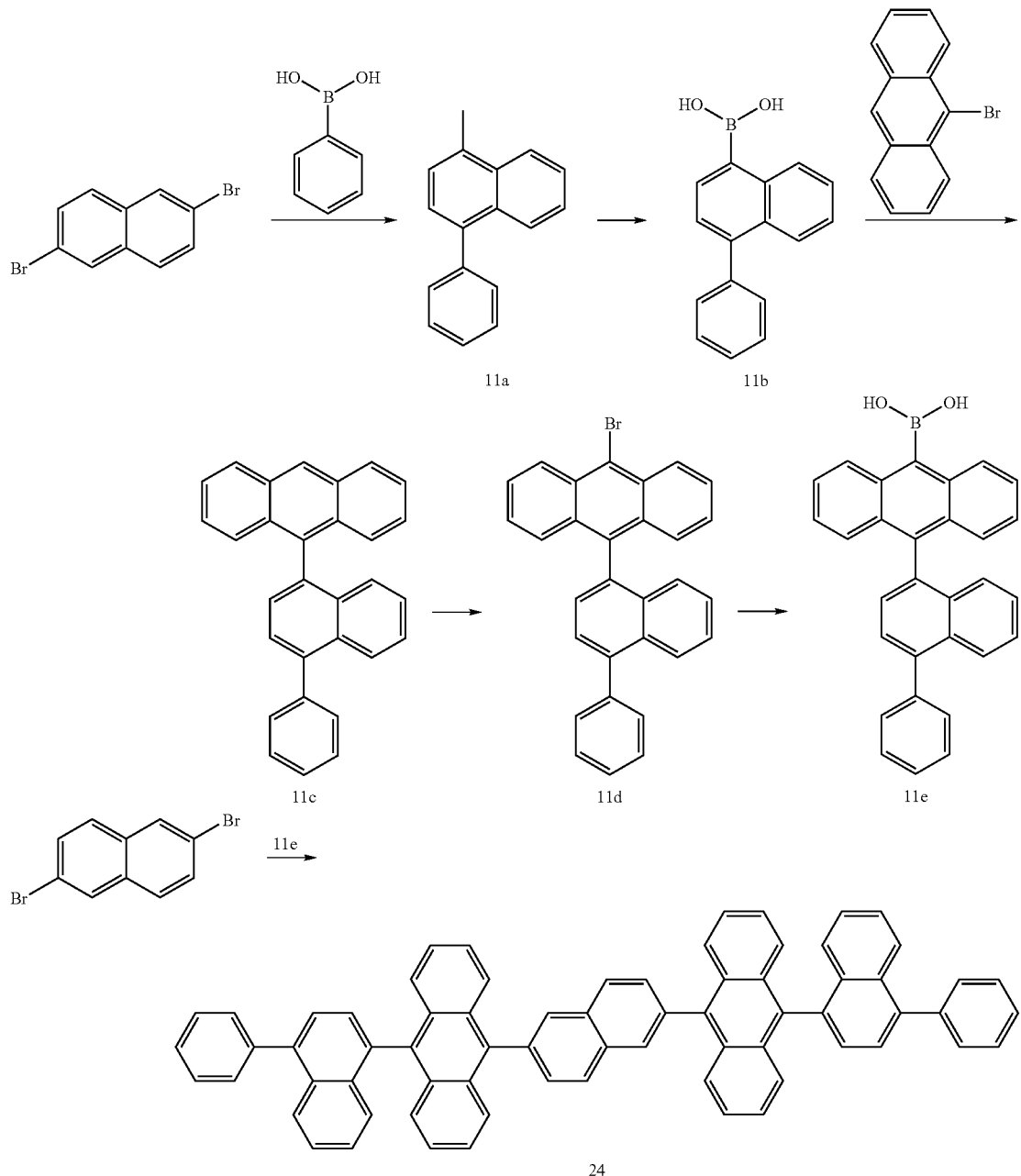

11-A. Preparation of Compound 11a

Under $N_2$ atmosphere, 2,6-dibromonaphthalene (20 g, 70 mmol), phenyl boronic acid (8.52 g, 70 mmol), and $Pd(PPh_3)_4$ (4.0 g, 3.5 mmol) were added to a 2 M aqueous solution of potassium carbonate (200 mL) and THF (300 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare a compound 11a (9.0 g, 45%). MS [M]=283

11-B. Preparation of Compound 11b

Under $N_2$ atmosphere, to a compound 11a (9.0 g, 31.7 mmol) prepared in 11-A, dehydrated ether (100 mL) and dehydrated toluene (100 mL) were added, and cooled to −64° C. in ice bath. A 2.5 M butyl lithium/hexane solution (12 mL) was added dropwise thereto for 30 minutes, and subjected to reaction at −64° C. for 2 hours. Boronic acid trimethyl ester (9 mL) was added dropwise thereto for 15 minutes, and then stirred at room temperature for 12 hours. After ice cooling, 2 N hydrochloric acid (200 mL) was added at 10° C. or lower and stirred for 24 hours. The mixture was separated, dried over magnesium sulfate, and concentrated under reduced pressure. The residue was recrystallized from EtOH to prepare a compound 11b (3.9 g, 50%).

11-C. Preparation of Compound 11c

Under N₂ atmosphere, 9-bromoanthracene (3 g, 11.7 mmol), the compound 11b (3.5 g, 14.1 mmol) prepared in 11-B, and Pd(PPh₃)₄ (0.68 g, 0.58 mmol) were added to a 2 M aqueous solution of potassium carbonate (100 mL) and THF (100 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was recrystallized from THF and EtOH to prepare a compound 11c (4.0 g, 90%). MS [M]=380

11-D. Preparation of Compound 11d

Under N₂ atmosphere, a compound 11c (4, 10.5 mmol) prepared in 11-C was dissolved in chloroform (60 mL). Acetic acid (80 mL) was added thereto, and Br₂ (0.56 mL, 11.0 mmol) was added dropwise at 0° C. The temperature of the mixture was raised to ambient temperature, and stirred for 5 hours. After completing the reaction, the resultant was concentrated, and recrystallized from EtOH to prepare a compound 11d (4.2 g, 86%). MS [M]+=459

11-E. Preparation of Compound 11e

Under N₂ atmosphere, to compound 11d (4 g, 8.7 mmol) prepared in 11-D, dehydrated ether (80 mL) and dehydrated toluene (40 mL) were added, and cooled to −64° C. in ice bath. A 2.5 M butyl lithium/hexane solution (6 mL) was added dropwise thereto for 30 minutes, and subjected to reaction at −64° C. for 2 hours. Boronic acid trimethylester (9 mL) was added dropwise thereto for 15 minutes, and then stirred at room temperature for 12 hours. After ice cooling, 2 N hydrochloric acid (35 mL) was added at 10° C. or lower and toluene (10 mL) was added. The mixture was separated, dried over magnesium sulfate, and concentrated under reduced pressure. The residue was recrystallized from hexane to prepare a yellow solid. To the solid, conc. hydrochloric acid (4 mL) and tetrabutylammonium bromide (0.04 g, 0.16 mmol) were added, and dissolved in THF (40 mL). The mixture was subjected to reaction at room temperature for 12 hours. After completing the reaction, the mixture was solidified in H₂O and filtered to prepare a compound 11e (1.8 g, 50%).

11-F. Preparation of Compound 24

Under N₂ atmosphere, 2,6-dibromonaphthalene (1 g, 3.5 mmol), the compound 11e (3.27 g, 7.69 mmol) prepared in 11-E, and Pd(PPh₃)₄ (0.2 g, 0.18 mmol) were added to a 2 M aqueous solution of potassium carbonate (100 mL) and anisole (100 mL). The mixture was refluxed under stirring, for about 24 hours. After completing the reaction, the mixture was cooled to normal temperature. The organic layer was separated from the reaction mixture, and filtered to obtain a solid. The solid was recrystallized from THF and EtOH to prepare a compound 24 (2.3 g, 75%). MS [M]=884

EXAMPLE 12

Preparation of Compound 25

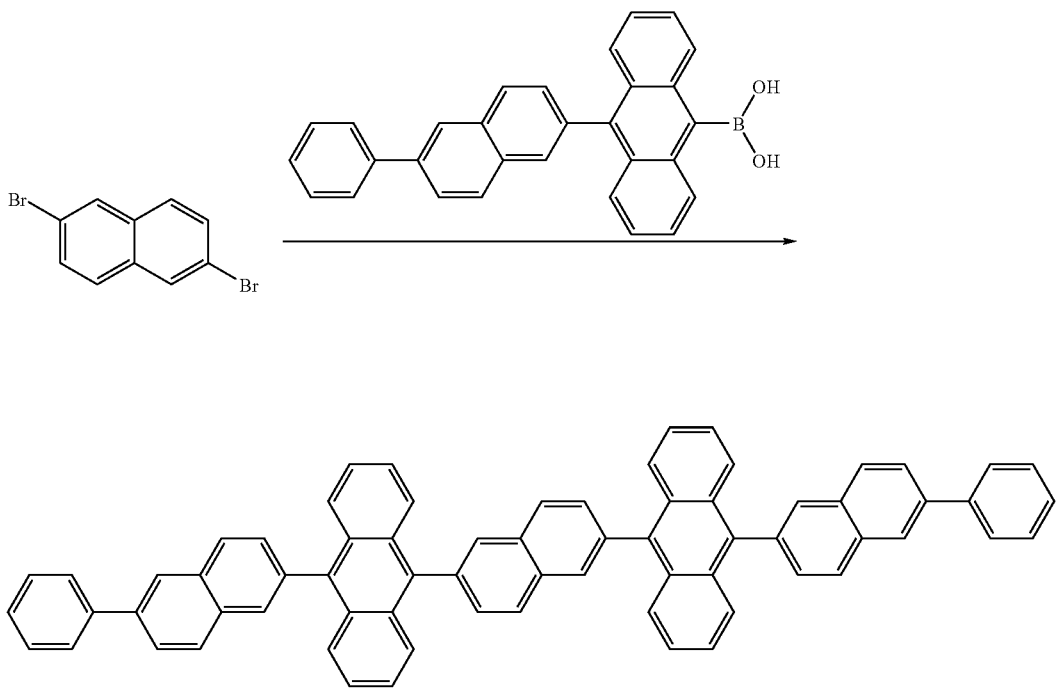

25

Under N₂ atmosphere, 2,6-dibromonaphthalene (1 g, 3.5 mmol), the compound 6e (3.27 g, 7.69 mmol) prepared in 6-E of Example 6, and Pd(PPh₃)₄ (0.2 g, 0.18 mmol) were added to a 2 M aqueous solution of potassium carbonate (100 mL) and anisole (100 mL). The mixture was refluxed under stirring for about 24 hours. After completing the reaction, the mixture was cooled to normal temperature. The organic layer was separated from the reaction mixture, and filtered to obtain a solid. The solid was recrystallized from THF and EtOH to prepare a compound 25 (2.45 g, 83%). MS [M]=884

EXAMPLE 13

Preparation of Compound 30

13-A. Preparation of Compound 13a

Under $N_2$ atmosphere, 1,3-dibromophenyl (10 g, 42.2 mmol), 2-naphthyl boronic acid (5.16 g, 42.2 mmol), and $Pd(PPh_3)_4$ (2.4 g, 2.1 mmol) were added to a 2 M aqueous solution of potassium carbonate (50 mL) and THF (300 mL). The mixture was refluxed under stirring for about 24 hours. After completing the reaction, the mixture was cooled to normal temperature. The organic layer was separated from

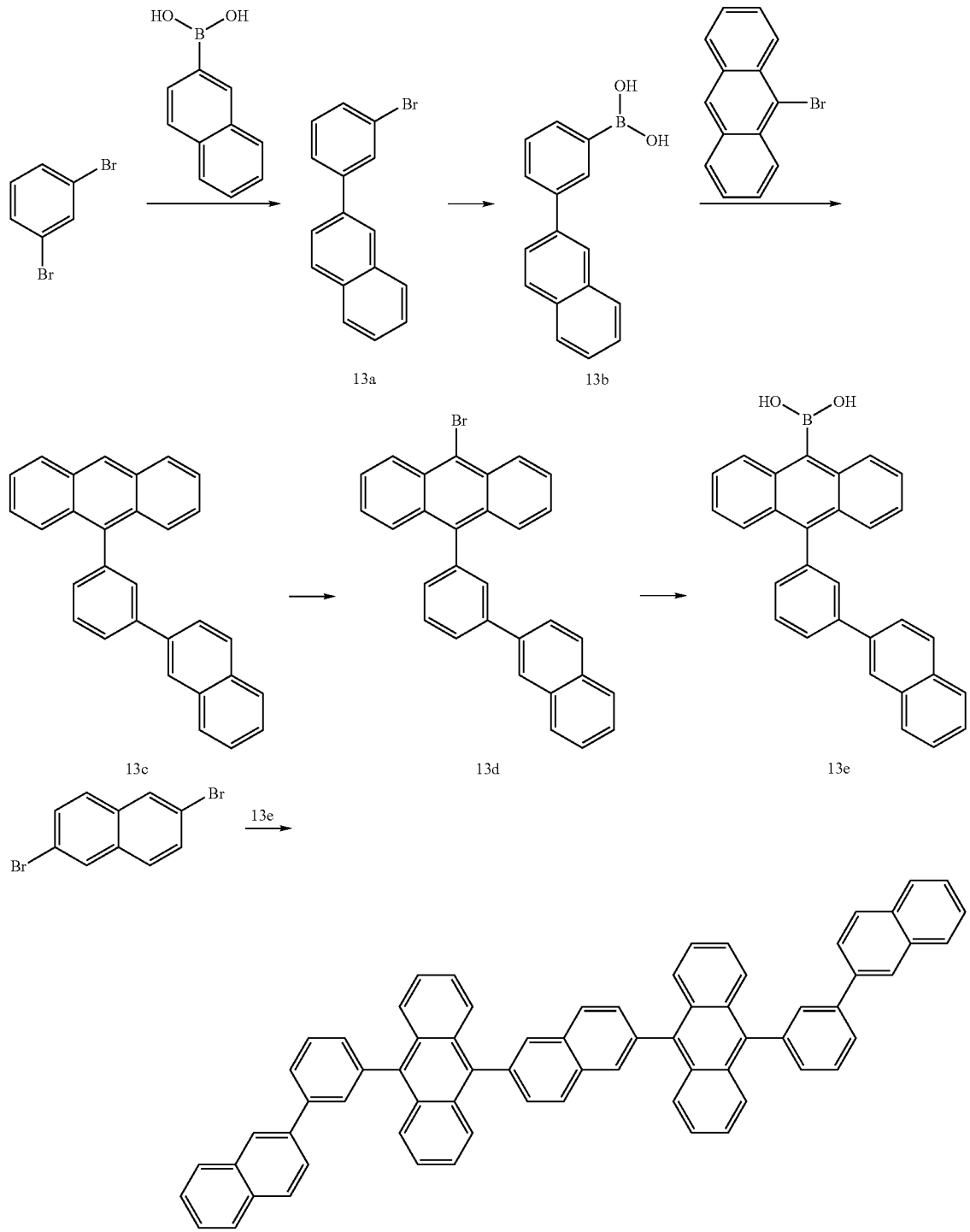

the reaction mixture, dried over magnesium sulfate, and distilled under reduced pressure. The resultant was purified by column chromatography to prepare a compound 13a (4.6 g, 47%). MS [M]=233

13-B. Preparation of Compound 13b

Under $N_2$ atmosphere, to a compound 13a (4 g, 14.1 mmol) prepared in 13-A, dehydrated ether (80 mL) and dehydrated toluene (80 mL) were added, and cooled to −64° C. in ice bath. A 2.5 M butyl lithium/hexane solution (6 mL) was added dropwise thereto for 30 minutes, and subjected to reaction at −64° C. for 2 hours. Boronic acid triisoester (9 mL) was added dropwise thereto for 15 minutes, and then stirred at room temperature for 12 hours. After ice cooling, 2 N hydrochloric acid (35 mL) was added at 10° C. or lower and toluene (10 mL) was added. The mixture was separated, dried over magnesium sulfate, and concentrated under reduced pressure. The residue was recrystallized from EtOH to prepare a compound 13b (1.75 g, 50%).

13-C. Preparation of Compound 13c

Under $N_2$ atmosphere, 9-bromoanthracene (5 g, 19.4 mmol), the compound 5b (4.6 g, 23.3 mmol), Pd(PPh$_3$)$_4$ (1.1 g, 0.97 mmol) were added to a 2 M aqueous solution of potassium carbonate (30 mL) and THF (300 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The resultant was recrystallized from THF and EtOH to prepare a compound 13c (5.4 g, 84%). MS [M]=330

13-D. Preparation of Compound 13d

Under $N_2$ atmosphere, a compound 13c (5 g, 15.1 mmol) was dissolved in chloroform (100 mL). Acetic acid (100 mL) was added thereto, and Br$_2$ (0.8 mL, 15.9 mmol) was added dropwise at 0° C. The temperature of the mixture was raised to ambient temperature, and stirred for 5 hours. After completing the reaction, the resultant was concentrated, and recrystallized from EtOH to prepare a compound 13d (4.4 g, 71%). MS [M]+=408

13-E. Preparation of Compound 13e

Under $N_2$ atmosphere, to a compound 13d (4 g, 9.8 mmol), dehydrated ether (40 mL) and dehydrated toluene (40 mL) were added, and cooled to −64° C. in ice bath. A 2.5 M butyl lithium/hexane solution (6 mL) was added dropwise thereto for 30 minutes, and subjected to reaction at −64° C. for 2 hours. Boronic acid trimethylester (9 mL) was added dropwise thereto for 15 minutes, and then stirred at room temperature for 12 hours. After ice cooling, 2 N hydrochloric acid (35 mL) was added at 10° C. or lower and toluene (10 mL) was added. The mixture was separated, dried over magnesium sulfate, and concentrated under reduced pressure. The residue was recrystallized from hexane to prepare a yellow solid. To the solid, conc. hydrochloric acid (4 mL) and tetrabutylammonium bromide (0.02 g, 0.1 mmol) were added, and dissolved in THF (40 mL). The mixture was subjected to reaction at room temperature for 12 hours. After completing the reaction, the mixture was solidified in H$_2$O and filtered to prepare a compound 13e (1.8 g, 50%).

13-F. Preparation of Compound 30

Under $N_2$ atmosphere, 2,6-dibromonaphthalene (1 g, 3.5 mmol), the compound 13e (2.88 g, 7.69 mmol), Pd(PPh$_3$)$_4$ (0.2 g, 0.18 mmol) were added to a 2 M aqueous solution of potassium carbonate (100 mL) and anisole (300 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 30 (1.9 g, 70%). MS [M]=884

EXAMPLE 14

Preparation of Compound 33

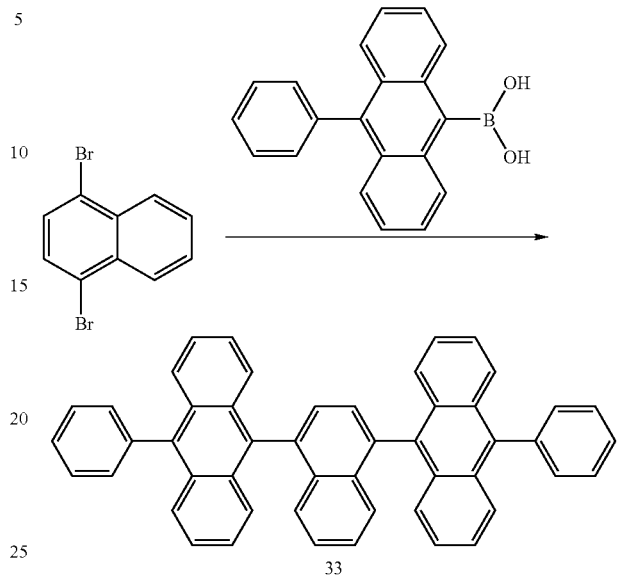

Under $N_2$ atmosphere, 1,4-dibromonaphthalene (1 g, 3.5 mmol), 10-phenylanthracene-9-boronic acid (2.62 g, 8.75 mmol), Pd(PPh$_3$)$_4$ (0.3 g, 0.3 mmol) were added to a 2 M aqueous solution of potassium carbonate (70 mL) and THF (150 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 33 (1.7 g, 77%). MS [M]=632

EXAMPLE 15

Preparation of Compound 34

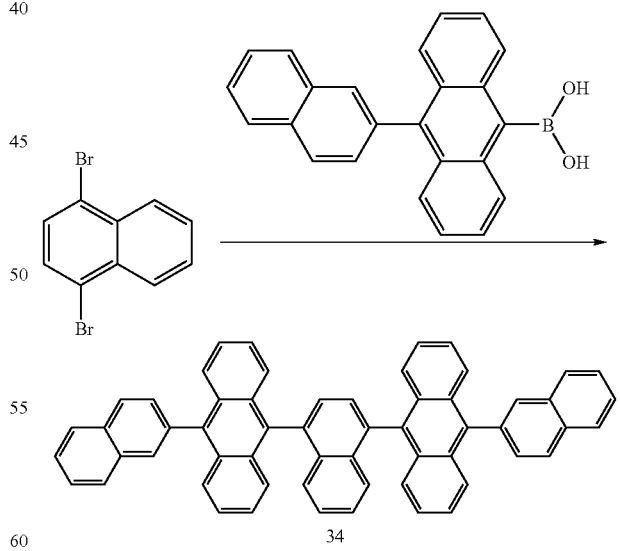

Under $N_2$ atmosphere, 1,4-dibromonaphthalene (1.5 g, 5.2 mmol), 10-(2-naphthyl)anthracene-9-boronic acid (4.0 g, 11.4 mmol), Pd(PPh$_3$)$_4$ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 34 (2.5 g, 66%). MS [M+H]=733

EXAMPLE 16

Preparation of Compound 35

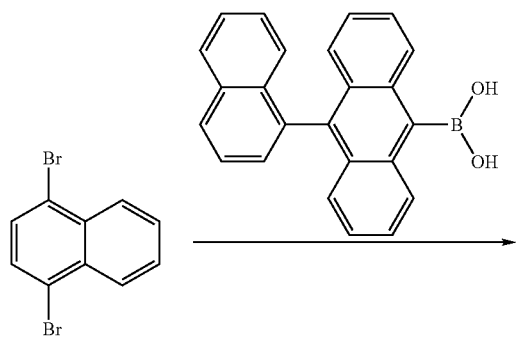

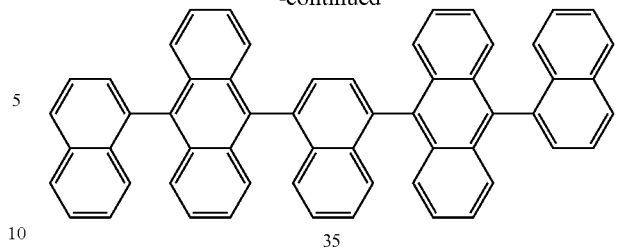

35

Under $N_2$ atmosphere, 1,4-dibromonaphthalene (1.5 g, 5.2 mmol), 10-(1-naphthyl)anthracene-9-boronic acid (4.0 g, 11.4 mmol), $Pd(PPh_3)_4$ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 35(2.3 g, 63%). MS [M+H]=733

EXAMPLE 17

Preparation of Compound 38

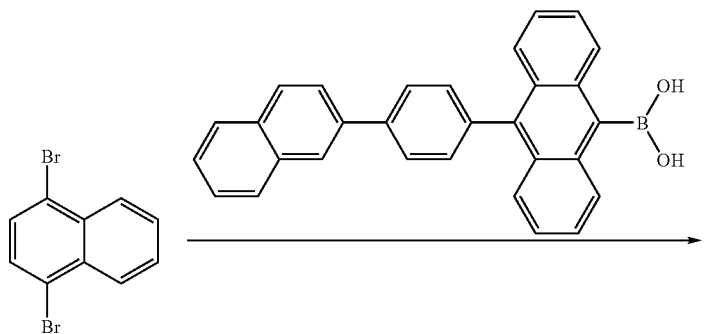

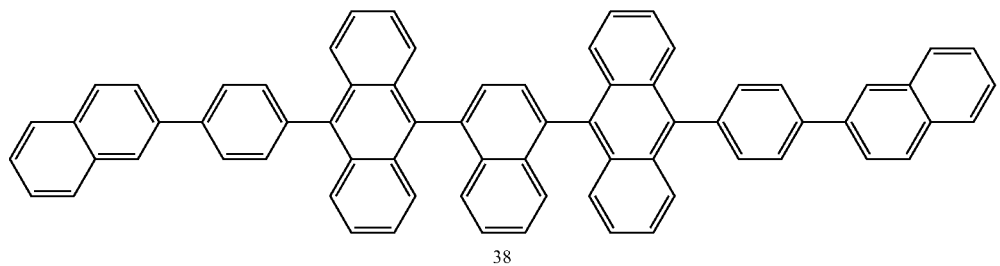

38

Under $N_2$ atmosphere, 1,4-dibromonaphthalene (1 g, 3.5 mmol), the compound 5e (3.27 g, 7.69 mmol) prepared in 5-E of Example 5, and $Pd(PPh_3)_4$ (0.2 g, 0.18 mmol) were added to a 2 M aqueous solution of potassium carbonate (100 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 38(2.3 g, 75%). MS [M]=884

EXAMPLE 18

Preparation of Compound 41

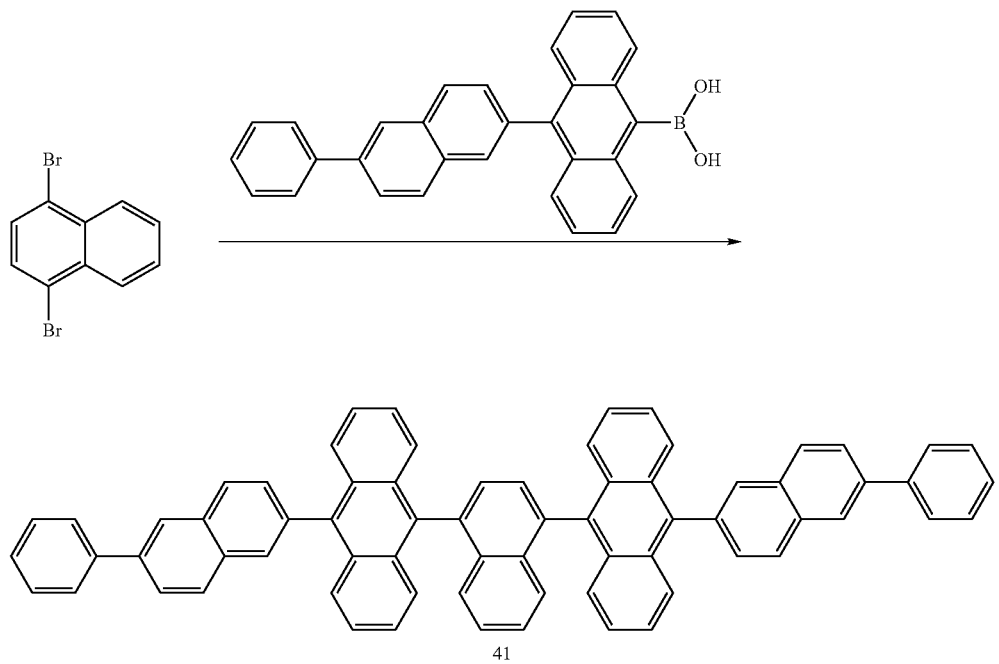

Under N₂ atmosphere, 1,4-dibromonaphthalene (1 g, 3.5 mmol), the compound 6e (3.27 g, 7.69 mmol) prepared in 6-E of Example 6, and Pd(PPh₃)₄ (0.2 g, 0.18 mmol) were added to a 2 M aqueous solution of potassium carbonate (100 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 41 (2.45 g, 83%). MS [M]=884

EXAMPLE 19

Preparation of Compound 46

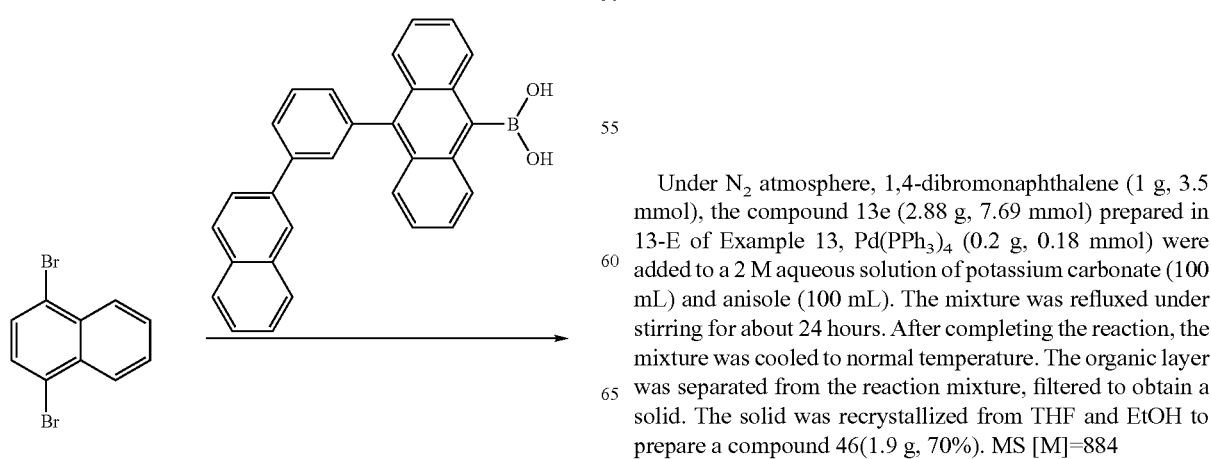

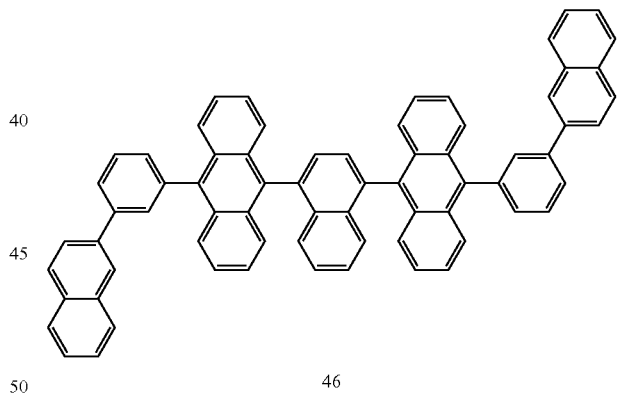

Under N₂ atmosphere, 1,4-dibromonaphthalene (1 g, 3.5 mmol), the compound 13e (2.88 g, 7.69 mmol) prepared in 13-E of Example 13, Pd(PPh₃)₄ (0.2 g, 0.18 mmol) were added to a 2 M aqueous solution of potassium carbonate (100 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 46(1.9 g, 70%). MS [M]=884

EXAMPLE 20

Preparation of Compound 50

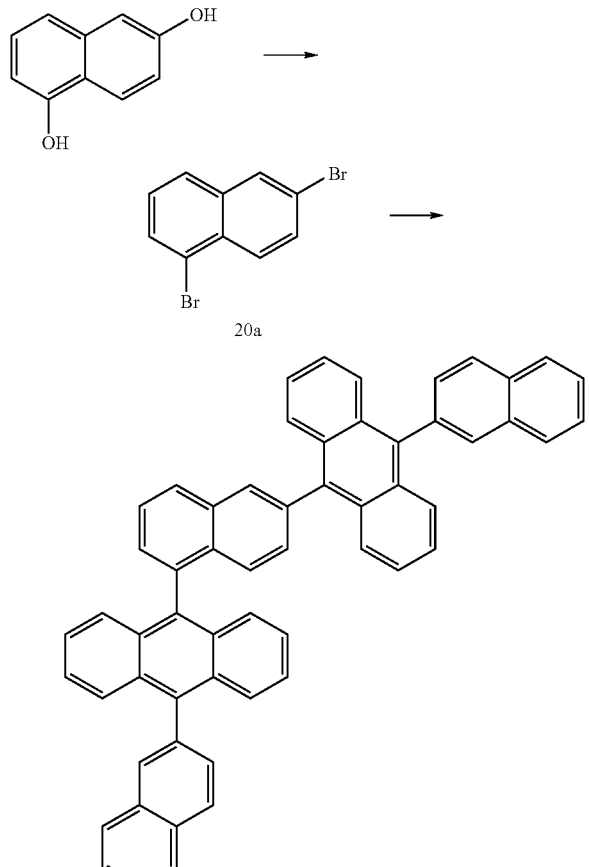

EXAMPLE 21

Preparation of Compound 65

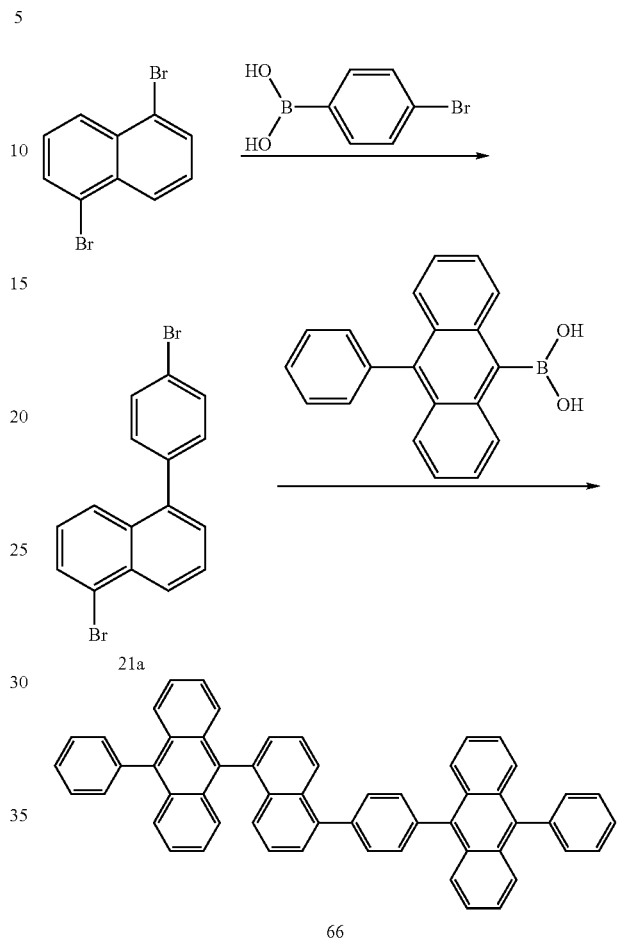

20-A. Preparation of Compound 20a

To 1,6-dihydroxynaphthalene (1.2 g, 7.68 mmol), acetonitrile (50 mL), $PBr_3$ (2.91 g, 10.8 mmol) was added, and heated under stirring for 48 hours. The mixture was cooled to normal temperature and then was added methanol (100 mL) to precipitate a solid. After the solid was filtered, washed with methanol sufficiently and dried to prepare a compound 20a 1,6-dibromonaphthalene (1.6 g, 74%). [M]=286

20-B. Preparation of Compound 50

Under $N_2$ atmosphere, 1,6-dibromonaphthalene (1.5 g, 5.2 mmol), 10-(2-naphthyl) anthracene-9-boronic acid (4.0 g, 11.4 mmol), $Pd(PPh_3)_4$ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 50 (2.5 g, 66%). MS [M+H]=733

21-A. Preparation of Compound 21a

Under $N_2$ atmosphere, 1,5-dibromonaphthalene (5 g, 17.5 mmol), 4-bromophenylboronic acid (3.5 g, 17.5 mmol), $Pd(PPh_3)_4$ (1.0 g, 0.88 mmol) were added to a 2 M aqueous solution of potassium carbonate (10 mL) and THF (200 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare a compound 21a (4.6 g, 73%). MS [M]=362

21-B. Preparation of Compound 65

Under $N_2$ atmosphere, a compound 21a (1 g, 2.8 mmol) prepared in 21-A, 10-phenyl anthracene-9-boronic acid (3.8 g, 6.1 mmol), $Pd(PPh_3)_4$ (0.16 g, 0.14 mmol) were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 65 (1.5 g, 75%). MS [M]=708

EXAMPLE 22

Preparation of Compound 66

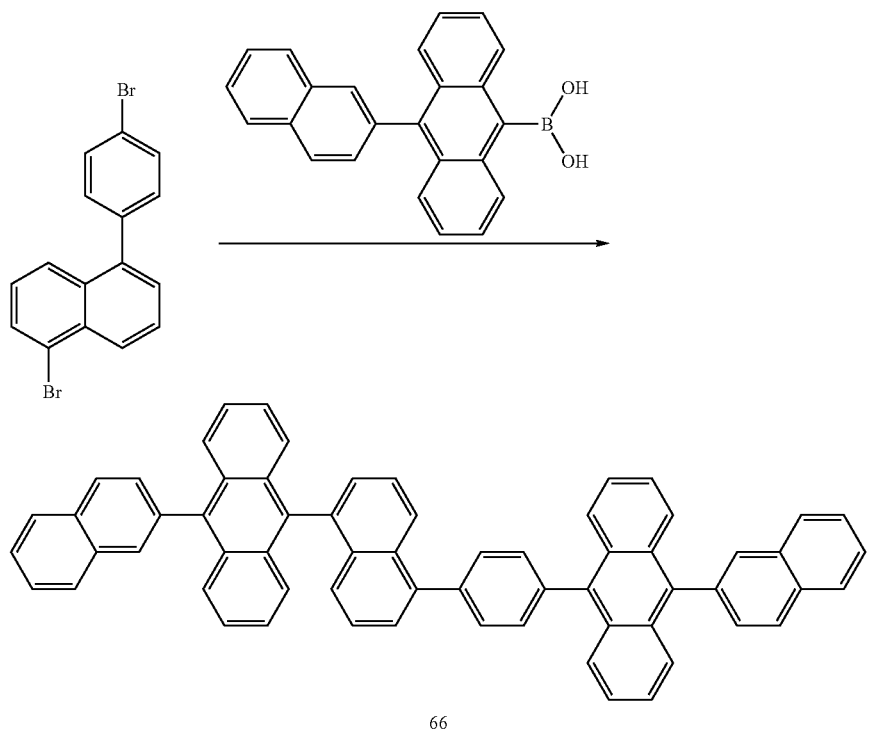

Under N$_2$ atmosphere, a compound 21a (1 g, 2.8 mmol) prepared in 21-A of Example 21, 10-(2-naphthyl)anthracene-9-boronic acid (2.1 g, 6.1 mmol), Pd(PPh$_3$)$_4$ (0.16 g, 0.14 mmol) were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 66 (1.8 g, 78%). MS [M]=808

EXAMPLE 23

Preparation of Compound 68

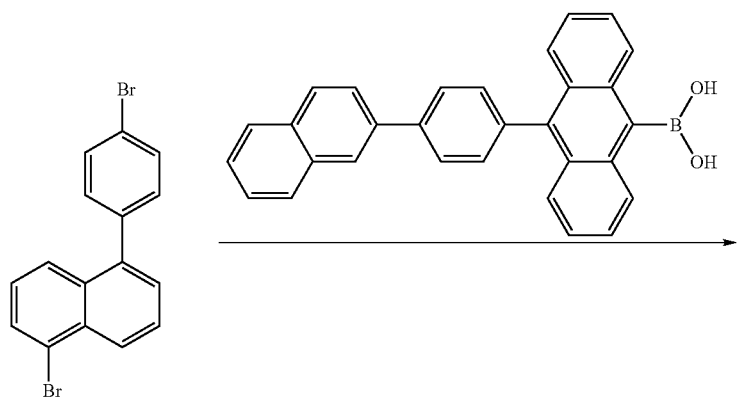

-continued

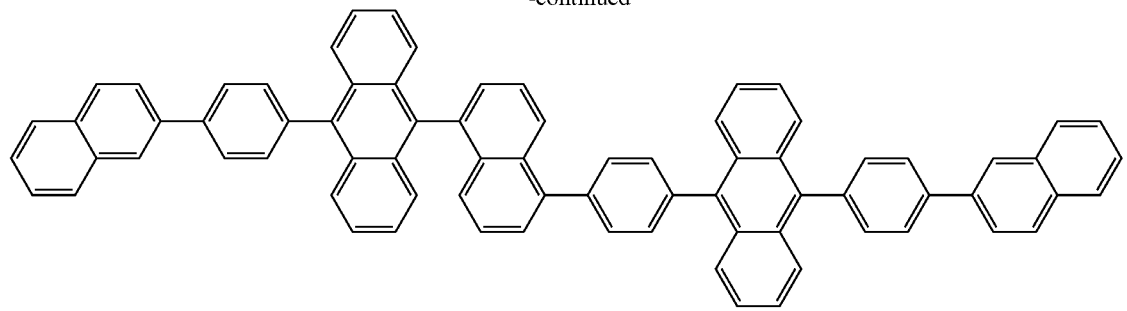

68

Under N₂ atmosphere, a compound 21a (1 g, 2.8 mmol) prepared in 21-A of Example 21, a compound 5e (2.6 g, 6.1 mmol) prepared in 5-E of Example 5, and Pd(PPh₃)₄ (0.2 g, 0.18 mmol) were added to a 2 M aqueous solution of potassium carbonate (100 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 68 (2.0 g, 74%). MS [M]=960

EXAMPLE 24

Preparation of Compound 78

24-A. Preparation of Compound 24a

Under N₂ atmosphere, 2,6-dibromonaphthalene (5 g, 17.5 mmol), 4-bromophenylboronic acid (3.5 g, 17.5 mmol), Pd(PPh₃)₄ (1.0 g, 0.88 mmol) were added to a 2 M aqueous solution of potassium carbonate (10 mL) and THF (200 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare compound 24a (4.7 g, 75%). MS [M]=362

24-B. Preparation of Compound 78

Under N₂ atmosphere, a compound 24a (1 g, 2.8 mmol) prepared in 24-A, 10-(2-naphthyl)anthracene-9-boronic acid (2.1 g, 6.1 mmol), and Pd(PPh₃)₄ (0.16 g, 0.14 mmol) were added to a 2 M aqueous solution of potassium carbonate (20

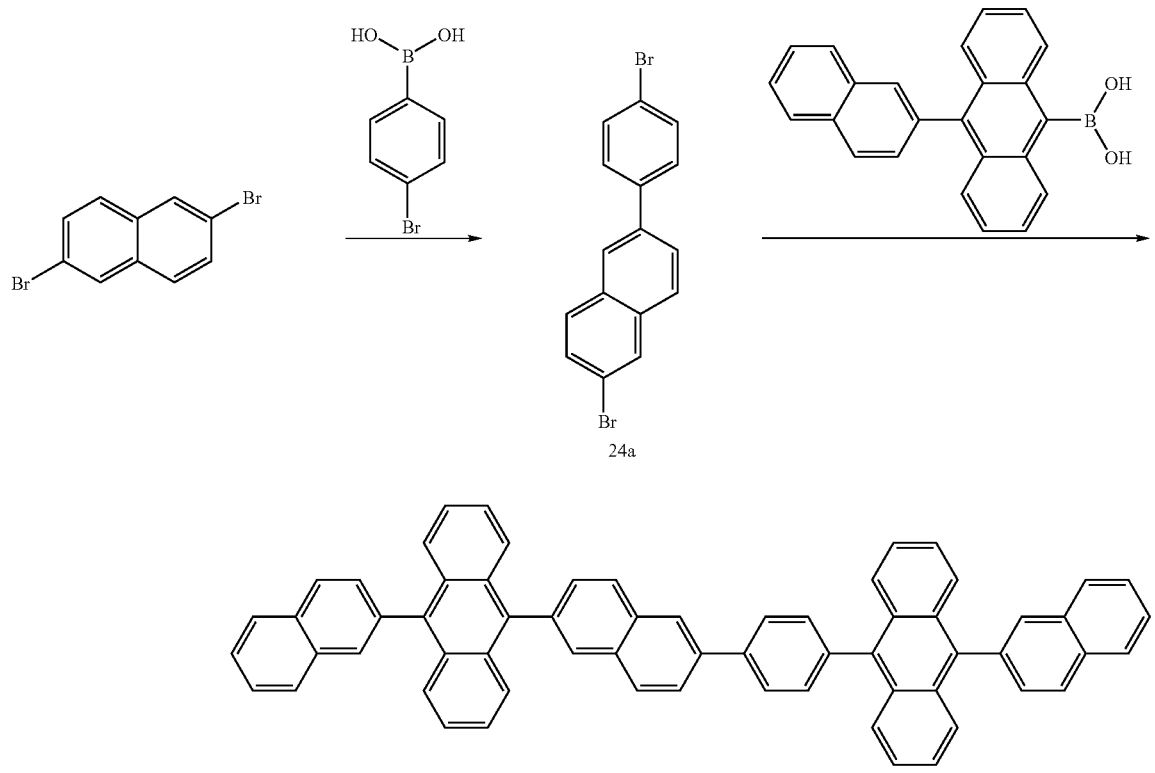

mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 78 (1.7 g, 75%). MS [M]=808

EXAMPLE 25

Preparation of Compound 81

25-B. Preparation of Compound 81

Under $N_2$ atmosphere, a compound 25a (1 g, 2.8 mmol) prepared in 25-A, 10-phenyl anthracene-9-boronic acid (3.8 g, 6.1 mmol), and Pd(PPh$_3$)$_4$ (0.16 g, 0.14 mmol) were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 81 (1.5 g, 75%). MS [M]=708

EXAMPLE 26

Preparation of Compound 85

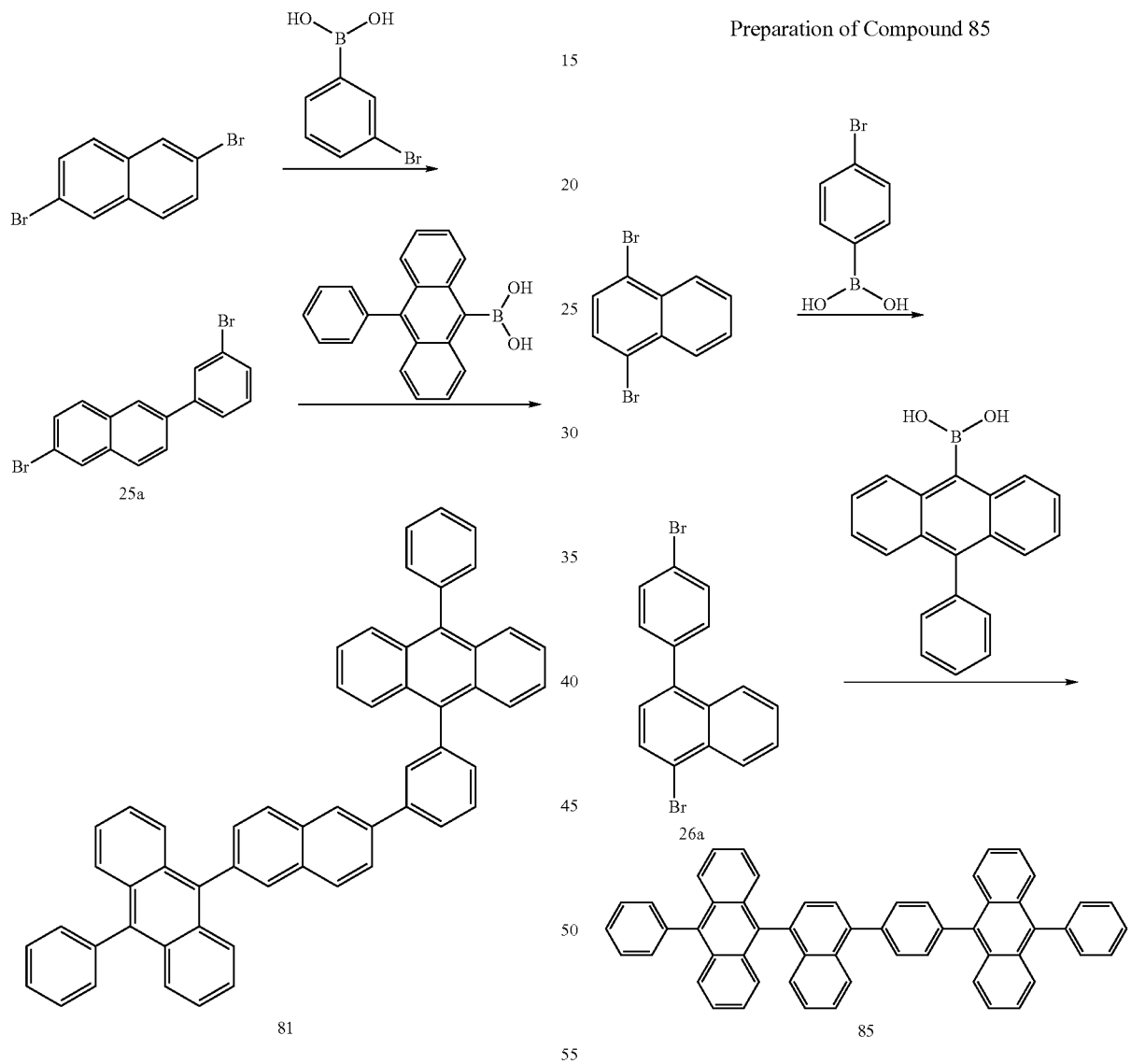

25-A. Preparation of Compound 25a

Under $N_2$ atmosphere, 2,6-dibromonaphthalene (5 g, 17.5 mmol), 3-bromophenylboronic acid (3.5 g, 17.5 mmol), and Pd(PPh$_3$)$_4$ (1.0 g, 0.88 mmol) were added to a 2 M aqueous solution of potassium carbonate (10 mL) and THF (200 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare 25a (4.8 g, 75%). MS [M]=362

26-A. Preparation of Compound 26a

Under $N_2$ atmosphere, 1,4-dibromonaphthalene (5 g, 17.5 mmol), 4-bromophenylboronic acid (3.5 g, 17.5 mmol), and Pd(PPh$_3$)$_4$ (1.0 g, 0.88 mmol) were added to a 2 M aqueous solution of potassium carbonate (10 mL) and THF (200 mL). The mixture was refluxed under stirring for about 24 hours. After, completing the reaction, the mixture was cooled to normal temperature. The organic layer was separated from the reaction mixture, dried over magnesium sulfate, and distilled under reduced pressure. The residue was purified by column chromatography to prepare compound 26a (4.8 g, 75%). MS [M]=362

26-B. Preparation of Compound 85

Under N₂ atmosphere, a compound 26a (1 g, 2.8 mmol) prepared in 26-A, 10-phenyl anthracene-9-boronic acid (3.8 g, 6.1 mmol), and Pd(PPh₃)₄ (0.16 g, 0.14 mmol) were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 85 (1.5 g, 75%). MS [M]=708

EXAMPLE 27

Preparation of Compound 86

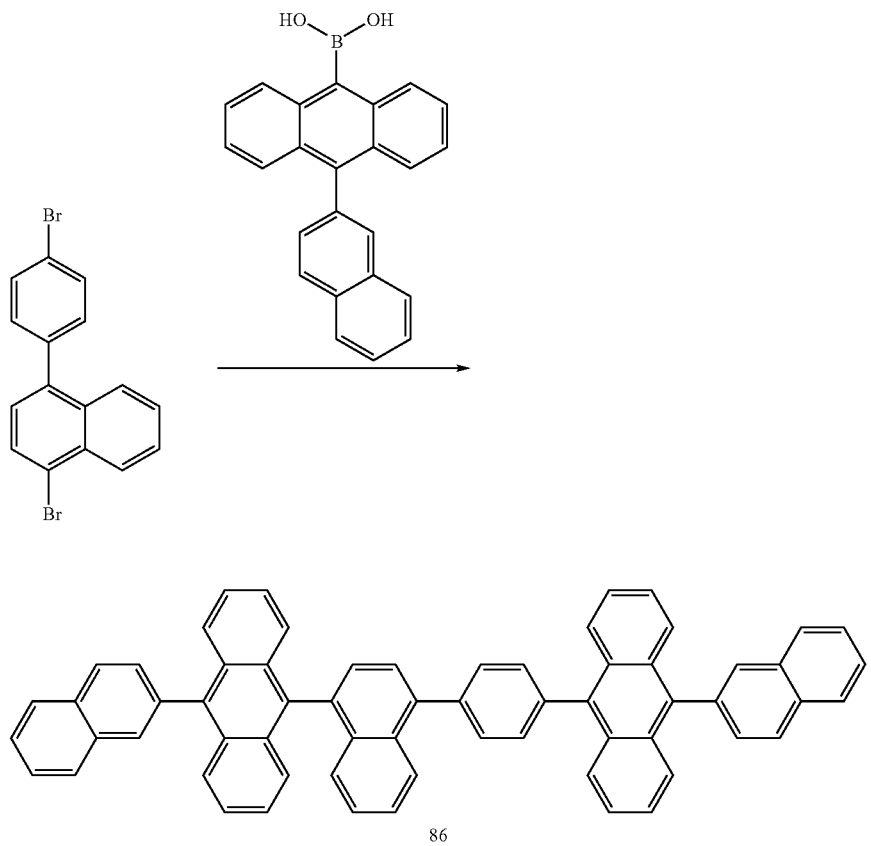

Under N₂ atmosphere, a compound 26a (1 g, 2.8 mmol) prepared in 26-A of Example 26, 10-(2-naphthyl)anthracene-9-boronic acid (2.1 g, 6.1 mmol), and Pd(PPh₃)₄ (0.16 g, 0.14 mmol) were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 86 (1.8 g, 78%). MS [M]=808

EXAMPLE 28

Preparation of Compound 89

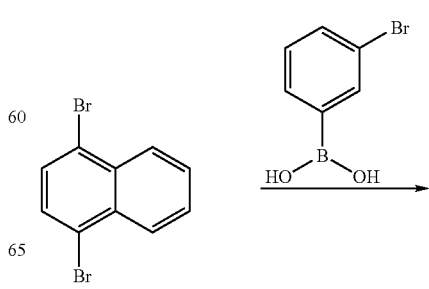

-continued

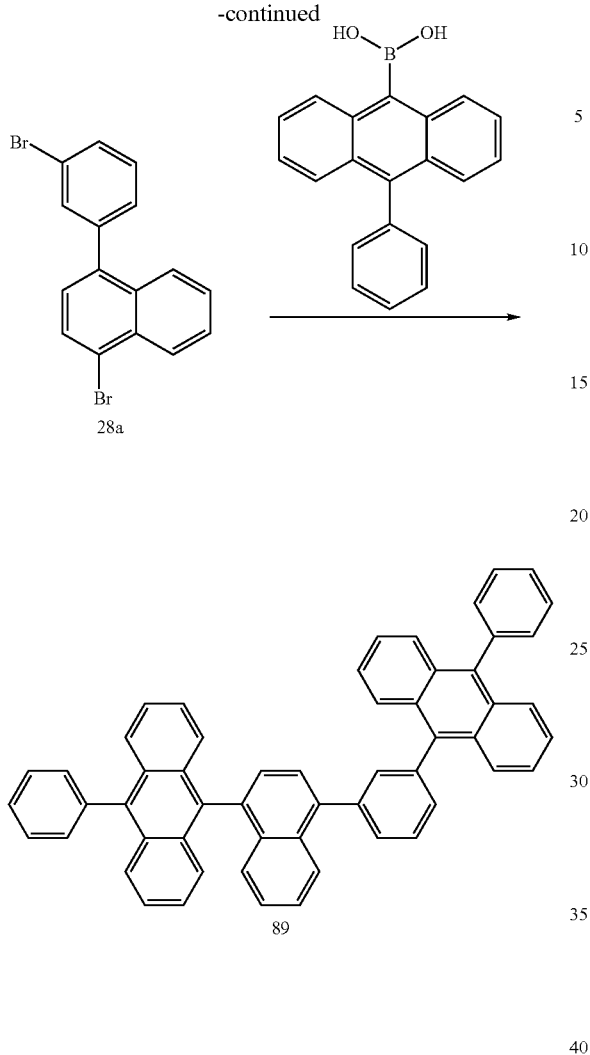

EXAMPLE 29

Preparation of Compound 90

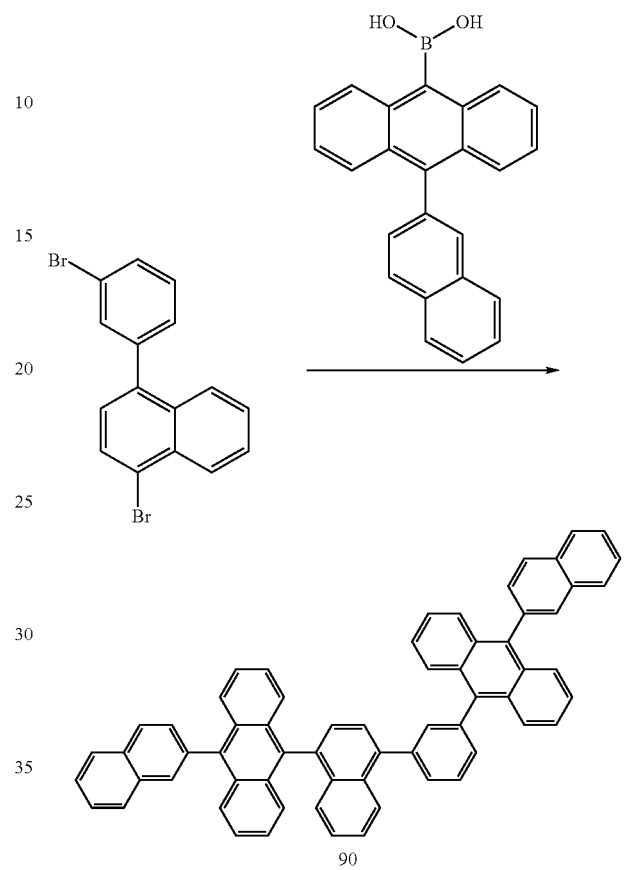

28-A. Preparation of Compound 28a

Under N₂ atmosphere, 1,4-dibromonaphthalene (5 g, 17.5 mmol), 3-bromophenylboronic acid (3.5 g, 17.5 mmol), and Pd(PPh₃)₄ (1.0 g, 0.88 mmol) were added to a 2 M aqueous solution of potassium carbonate (10 mL) and THF (200 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare compound 28a (4.8 g, 75%). MS [M]=362

28-B. Preparation of Compound 89

Under N₂ atmosphere, a compound 28a (1 g, 2.8 mmol) prepared in 28-A, 10-phenyl anthracene-9-boronic acid (3.8 g, 6.1 mmol), and Pd(PPh₃)₄ (0.16 g, 0.14 mmol) were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 89(1.5 g, 75%). MS [M]=708

Under N₂ atmosphere, a compound 28a (1 g, 2.8 mmol) prepared in 28-A of Example 28, 10-(2-naphthyl)anthracene-9-boronic acid (2.1 g, 6.1 mmol), and Pd(PPh₃)₄ (0.16 g, 0.14 mmol) were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 90 (1.8 g, 78%). MS [M]=808

EXAMPLE 30

Preparation of Compound 102

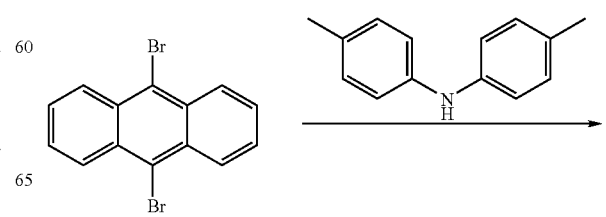

-continued

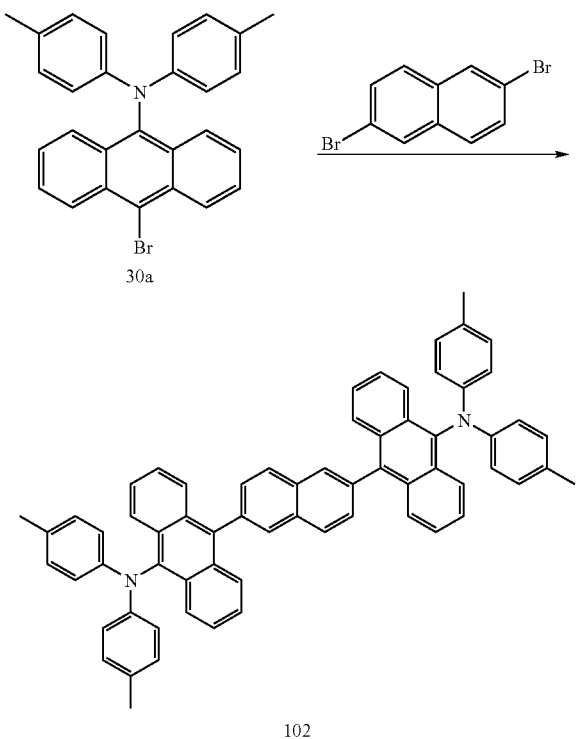

30-A. Preparation of Compound 30a

Under N$_2$ atmosphere, 9,10-dibromoanthracene (5 g, 14.9 mmol) and p-tolylamine (2.9 g, 14.9 mmol) were dissolved in toluene (80 mL). NaOtBu (1.6 g, 16.4 mmol) was added thereto, and stirred for 10 minutes. To the mixture, Pd(dba)$_2$ (0.17 g, 0.3 mmol) and tri-t-butylphosphine (0.06 g, 0.3 mmol) were added, and refluxed for 30 minutes with raising temperature. After washing with saline water, the organic layer was extracted from ethyl acetate. The moisture was removed over anhydrous magnesium sulfate. The solvent was removed under reduced pressure and the resultant was recrystallized from THF and EtOH to prepare a compound 30a (2.7 g, 40%). MS [M] 452

30-B. Preparation of Compound 102

Under N$_2$ atmosphere, 2,6-dibromonaphthalene (5 g, 17.5 mmol) and magnesium (0.9 g) were added to THF (300 mL) to prepare a Grignard reagent. To the mixture, bis(triphenylphosphine)nickel chloride (1.4 g) was added. A compound 30a (17 g, 38.5 mmol) prepared in 30-A was dissolved in THF (120 mL) and then was added thereto. The mixture was stirred at 60° C. for 12 hours. The temperature was raised to ambient temperature. To the reaction solution, 3% of hydrochloric acid was added to precipitate. The precipitate was filtered, dissolved in THF and was purified by column chromatography to prepare a compound 102 (5.8 g, 38%). MS [M] 870

EXAMPLE 31

Preparation of Compound 110

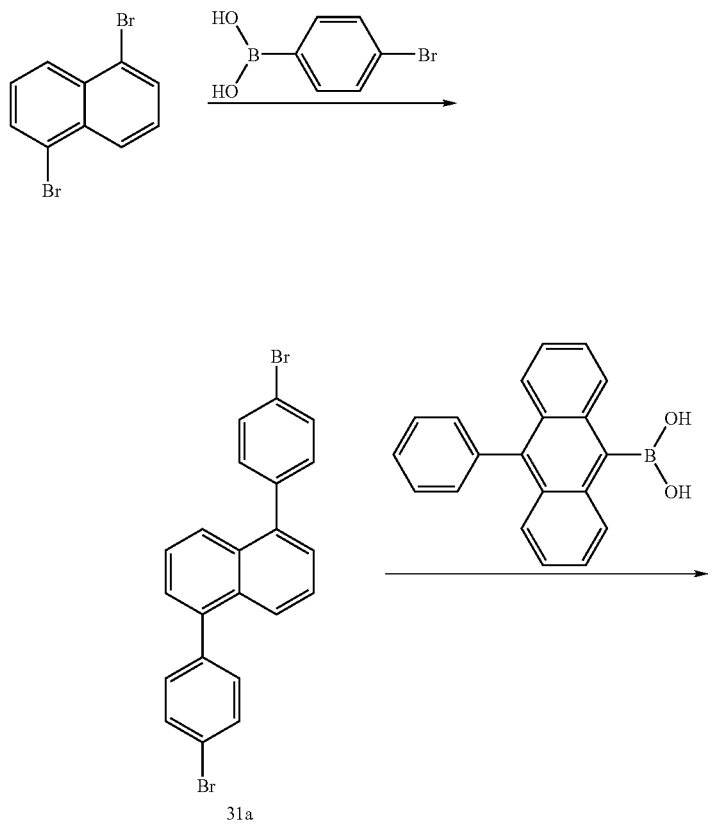

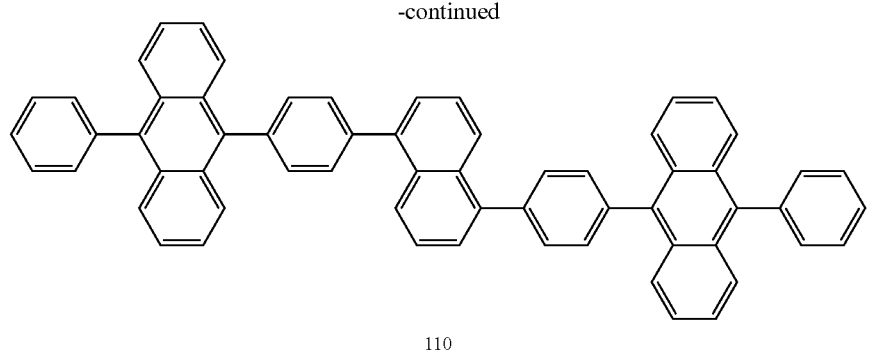

110

31-A. Preparation of Compound 31a

Under $N_2$ atmosphere, 1,5-dibromonaphthalene (5 g, 17.5 mmol), 4-bromophenylboronic acid (7.03 g, 35 mmol), and $Pd(PPh_3)_4$ (1.0 g, 0.88 mmol) were added to a 2 M aqueous solution of potassium carbonate (10 mL) and THF (200 mL). The mixture was refluxed under stirring for about 12 hours. After completing the reaction, the mixture was cooled to normal temperature. The organic layer was separated from the reaction mixture, dried over magnesium sulfate, and distilled under reduced pressure. The residue was purified by column chromatography to prepare compound 31a (3.8 g, 50%). MS [M+H]=438

2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 110 (1.5 g, 70%). MS [M+H]+=784

EXAMPLE 32

Preparation of Compound 111

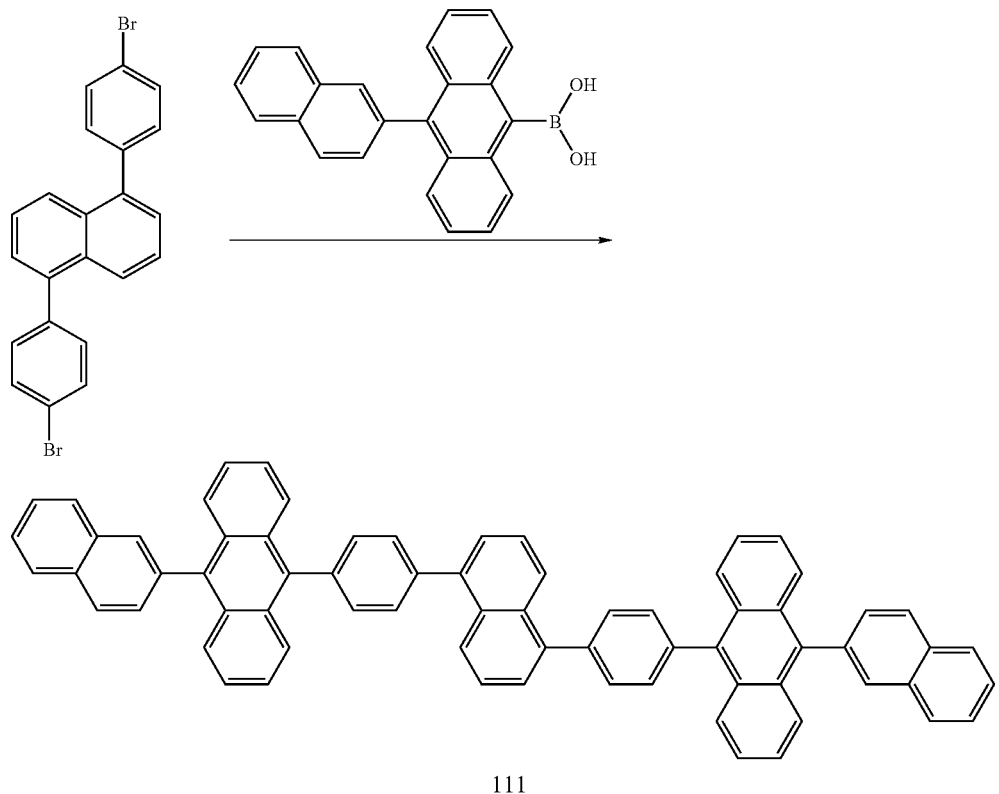

111

31-B. Preparation of Compound 110

Under $N_2$ atmosphere, a compound 31a (1.2 g, 2.8 mmol) prepared in 31-A, 10-phenyl anthracene-9-boronic acid (3.8 g, 6.1 mmol), $Pd(PPh_3)_4$ (0.16 g, 0.14 mmol) were added to a Under $N_2$ atmosphere, a compound 31a (2.28 g, 5.2 mmol) prepared in 31-A of Example 31, 10-(2-naphthyl)anthracene-9-boronic acid (4.0 g, 11.4 mmol), and $Pd(PPh_3)_4$ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 111 (2.5 g, 66%). MS [M+H]+=884

EXAMPLE 33

Preparation of Compound 122 solution of potassium carbonate (10 mL) and THF (200 mL). The mixture was refluxed under stirring for about 12 hours. After completing the reaction, the mixture was cooled to normal temperature. The organic layer was separated from the reaction mixture, dried over magnesium sulfate, and distilled under reduced pressure. The residue was purified by column chromatography to prepare a compound 33a (3.8 g, 50%). MS [M+H]+=438

33-B. Preparation of Compound 122

Under $N_2$ atmosphere, a compound 33a (1.2 g, 2.8 mmol) prepared in 33-A, 10-phenyl anthracene-9-boronic acid (3.8 g, 6.1 mmol), Pd(PPh$_3$)$_4$ (0.16 g, 0.14 mmol) were added to a 2 M aqueous solution of potassium carbonate (20 mL) and

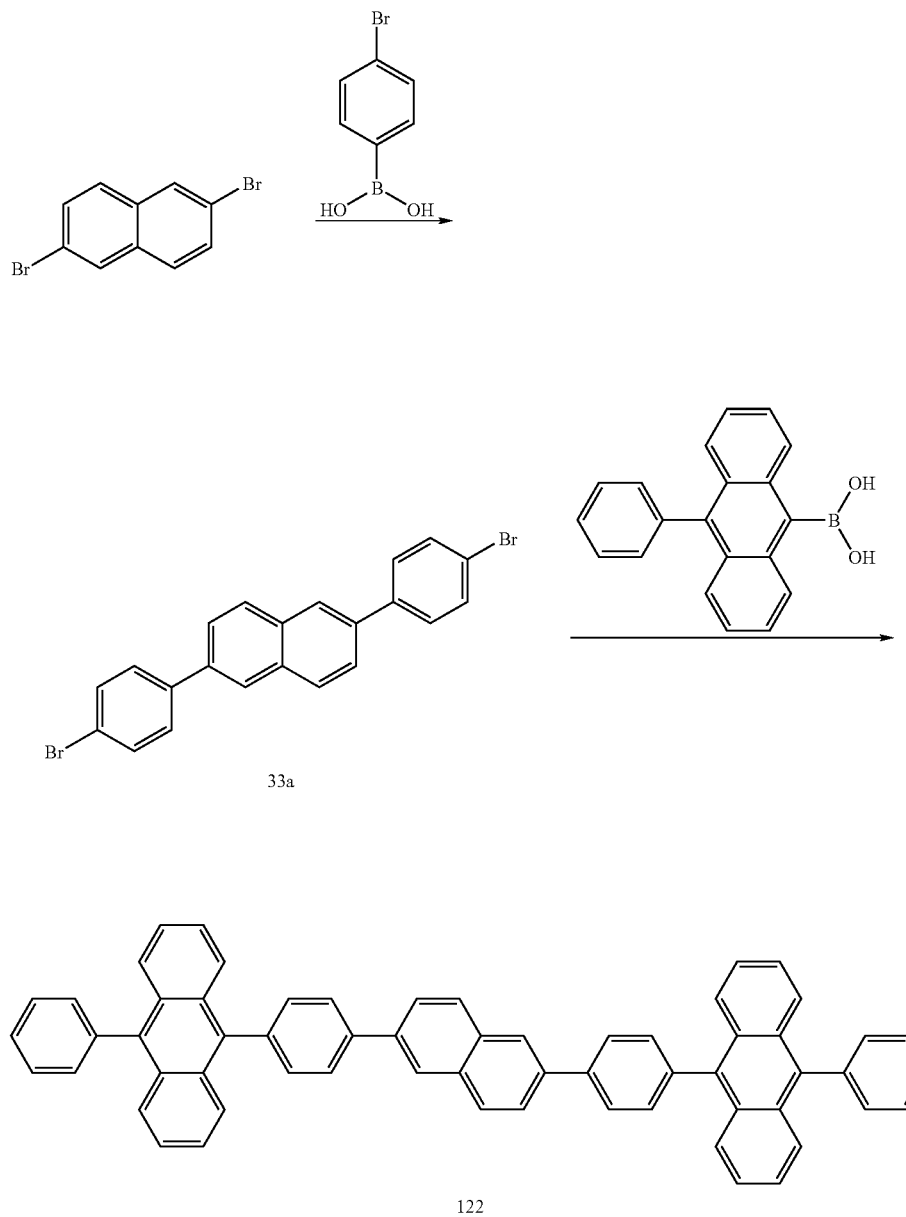

33-A. Preparation of Compound 33a

Under $N_2$ atmosphere, 2,6-dibromonaphthalene (5 g, 17.5 mmol), 4-bromophenylboronic acid (7.03 g, 35 mmol), and Pd(PPh$_3$)$_4$ (1.0 g, 0.88 mmol) were added to a 2 M aqueous anisole (100 mL). The mixture was refluxed under stirring for about 24 hours. After completing the reaction, the mixture was cooled to normal temperature. The organic layer was separated from the reaction mixture, filtered to obtain a solid.

The solid was recrystallized from THF and EtOH to prepare a compound 122 (1.5 g, 70%). MS [M+H]+=784

EXAMPLE 34

Preparation of Compound 123

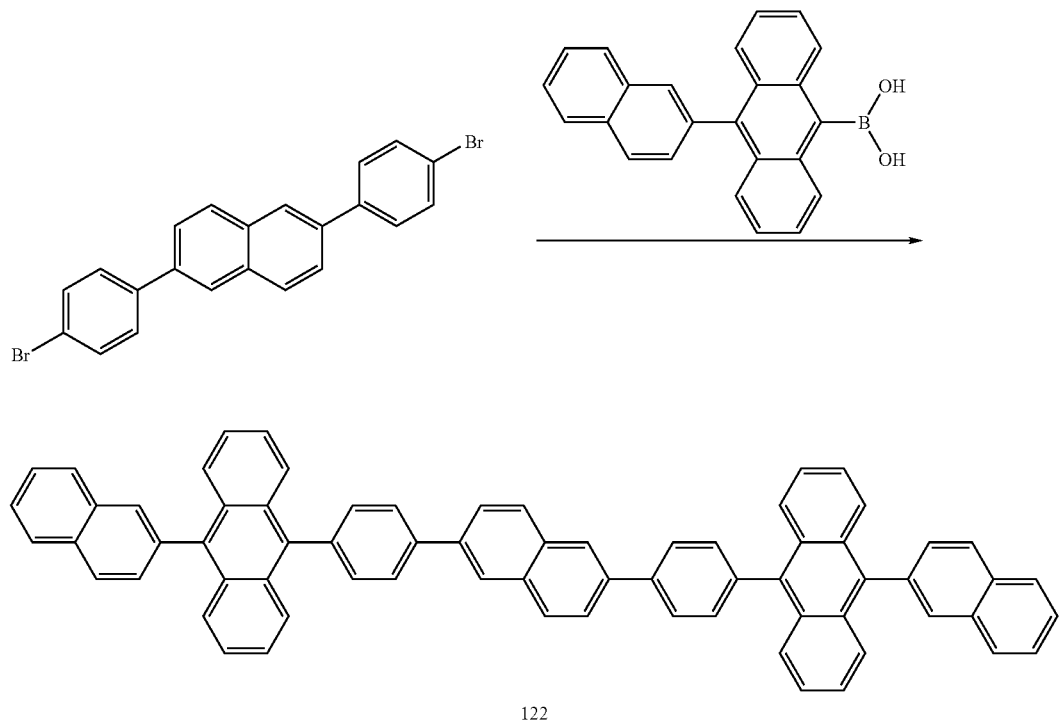

122

Under N₂ atmosphere, a compound 33a (2.28 g, 5.2 mmol) prepared in 33-A of Example 33, 10-(2-naphthyl)anthracene-9-boronic acid (4.0 g, 11.4 mmol), and Pd(PPh₃)₄ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 123 (2.5 g, 66%). MS [M+H]+=884

EXAMPLE 35

Preparation of Compound 134

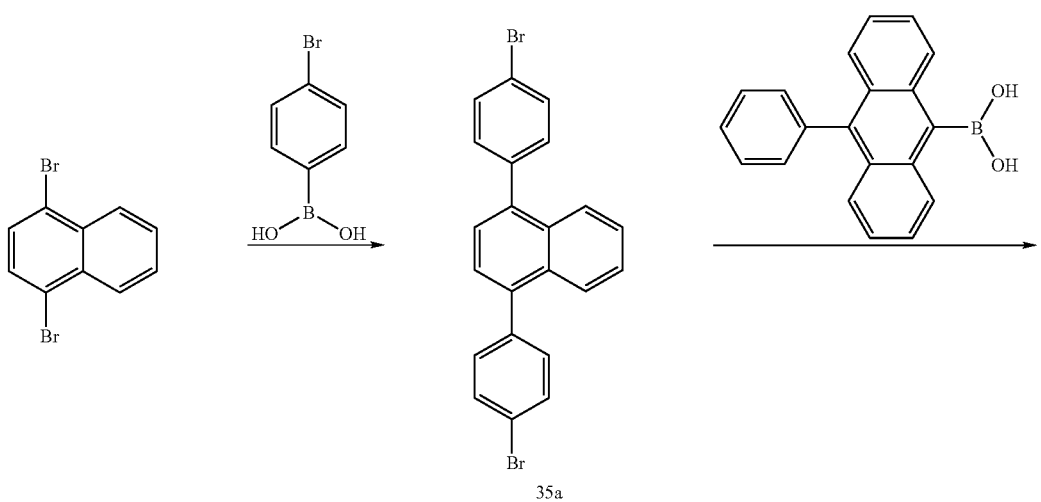

35a

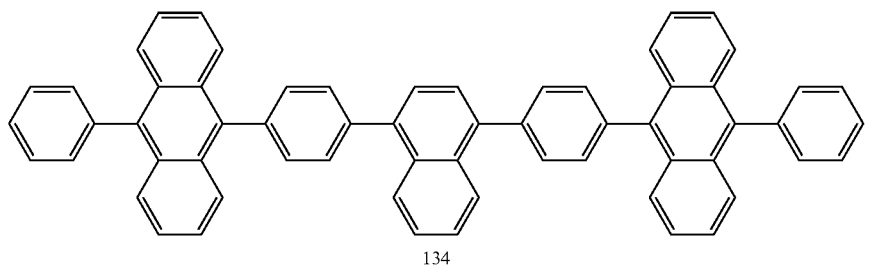

134

35-A. Preparation of Compound 35a

Under $N_2$ atmosphere, 1,4-dibromonaphthalene (5 g, 17.5 mmol), 4-bromophenylboronic acid (7.03 g, 35 mmol), and Pd(PPh$_3$)$_4$ (1.0 g, 0.88 mmol) were added to a 2 M aqueous solution of potassium carbonate (10 mL) and THF (200 mL). The mixture was refluxed under stirring for about 12 hours. After completing the reaction, the mixture was cooled to normal temperature. The organic layer was separated from the reaction mixture, dried over magnesium sulfate, and distilled under reduced pressure. The residue was purified by column chromatography to prepare a compound 35a (3.8 g, 50%). MS [M+H]+=438

35-B. Preparation of Compound 134

Under $N_2$ atmosphere, a compound 35a (1.2 g, 2.8 mmol) prepared in 35-A, 10-phenyl anthracene-9-boronic acid (3.8 g, 6.1 mmol), and Pd(PPh$_3$)$_4$ (0.16 g, 0.14 mmol) were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 134 (1.5 g, 70%). MS [M+H]+=784

EXAMPLE 36

Preparation of Compound 135

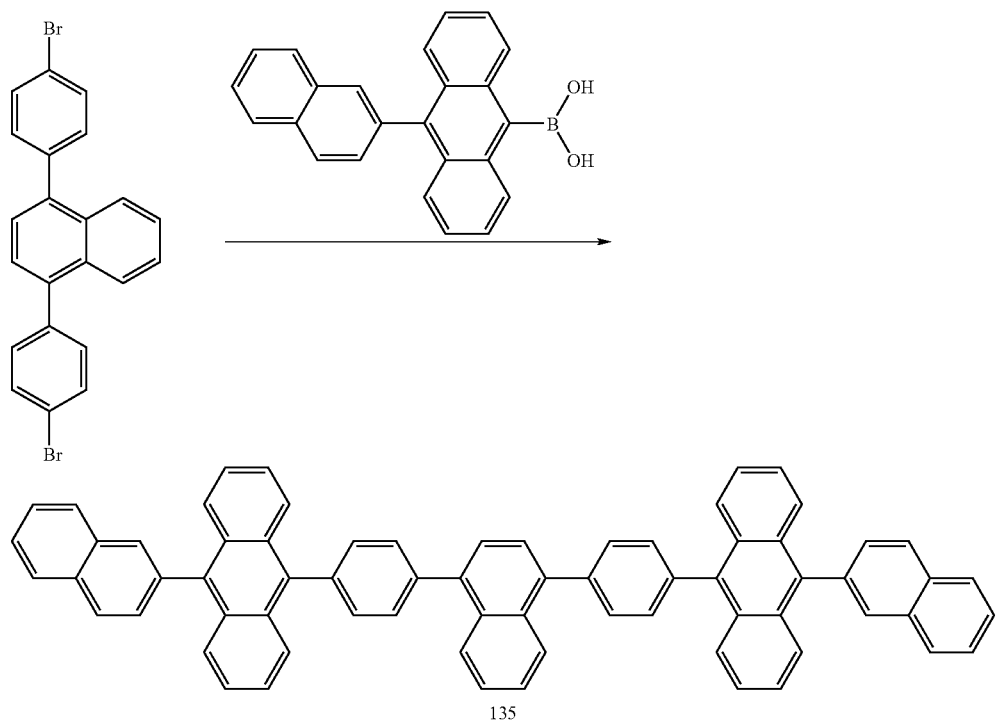

135

Under $N_2$ atmosphere, a compound 35a (2.28 g, 5.2 mmol) prepared in 35-A of Example 35, 10-(2-naphthyl)anthracene-9-boronic acid (4.0 g, 11.4 mmol), and Pd(PPh$_3$)$_4$ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 135 (2.5 g, 66%). MS [M+H]+=884

EXAMPLE 37

Preparation of Compound 146

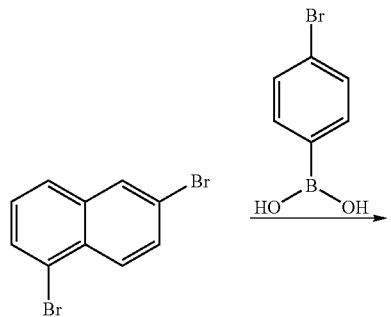

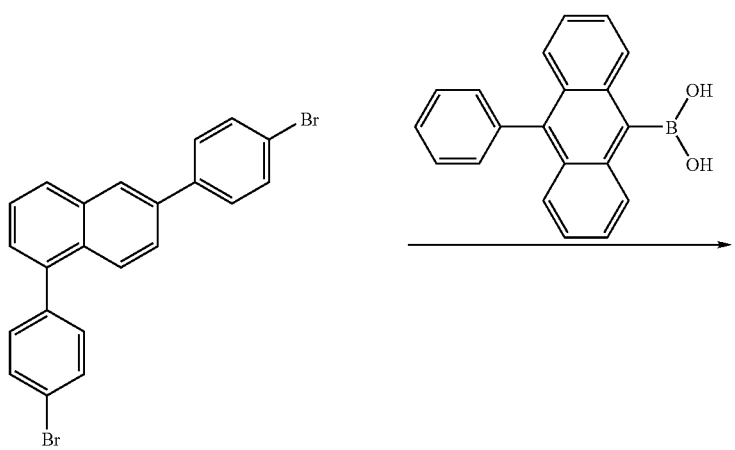

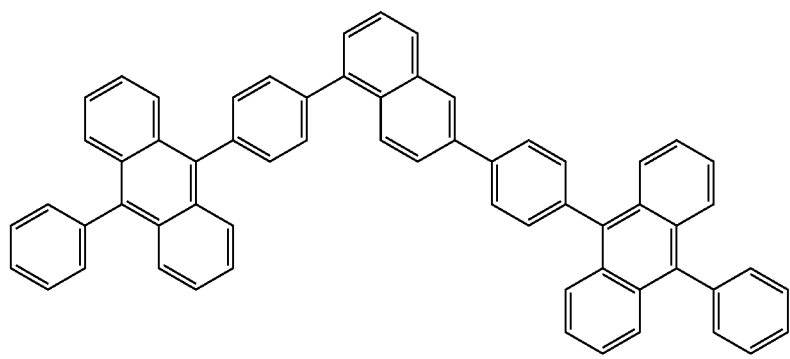

146

37-A. Preparation of Compound 37a

Under $N_2$ atmosphere, 1,6-dibromonaphthalene (5 g, 17.5 mmol), 4-bromophenylboronic acid (7.03 g, 35 mmol), and Pd(PPh$_3$)$_4$ (1.0 g, 0.88 mmol) were added to a 2 M aqueous solution of potassium carbonate (10 mL) and THF (200 mL). The mixture was refluxed under stirring for about 12 hours. After completing the reaction, the mixture was cooled to normal temperature. The organic layer was separated from the reaction mixture, dried over magnesium sulfate, and distilled under reduced pressure. The residue was purified by column chromatography to prepare a compound 37a (3.8 g, 50%). MS [M+H]+=438

37-B. Preparation of Compound 146

Under $N_2$ atmosphere, a compound 37a (1.2 g, 2.8 mmol) prepared in 37-A, 10-phenyl anthracene-9-boronic acid (3.8 g, 6.1 mmol), Pd(PPh$_3$)$_4$ (0.16 g, 0.14 mmol were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 146 (1.5 g, 70%). MS [M+H]+=784

EXAMPLE 38

Preparation of Compound 147

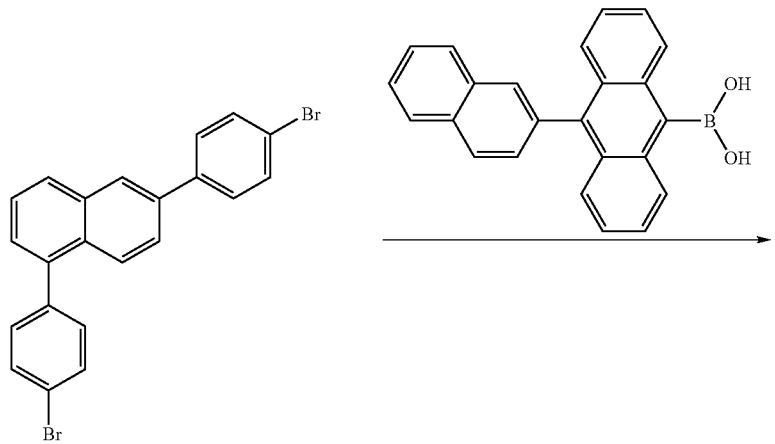

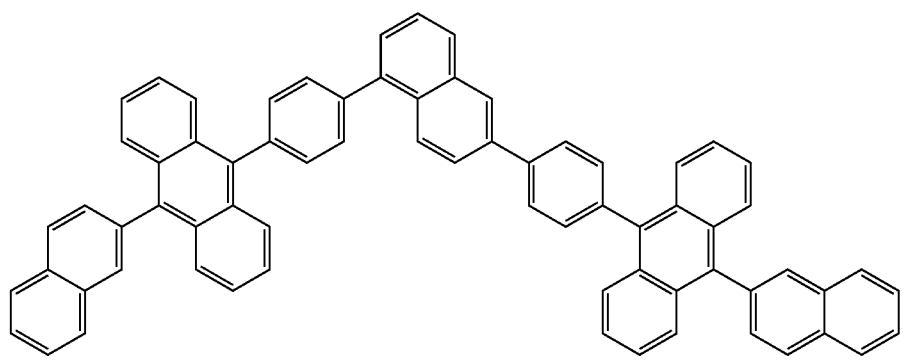

147

Under $N_2$ atmosphere, a compound 37a (2.28 g, 5.2 mmol) prepared in 37-A of Example 37, 10-(2-naphthyl)anthracene-9-boronic acid (4.0 g, 11.4 mmol), and $Pd(PPh_3)_4$ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 147 (2.5 g, 66%). MS [M+H]+=884

EXAMPLE 39

Preparation of Compound 158

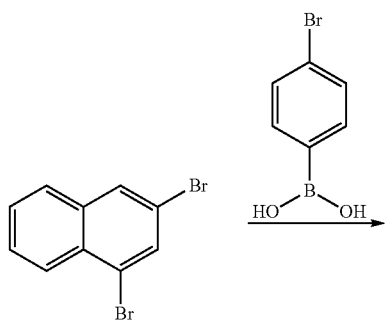

-continued

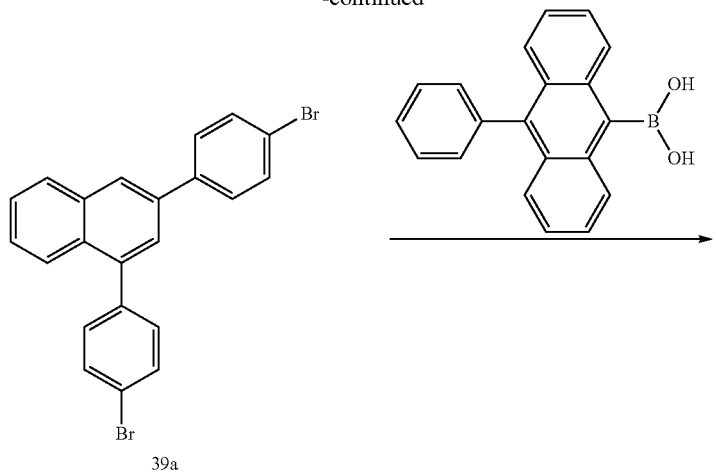

39a

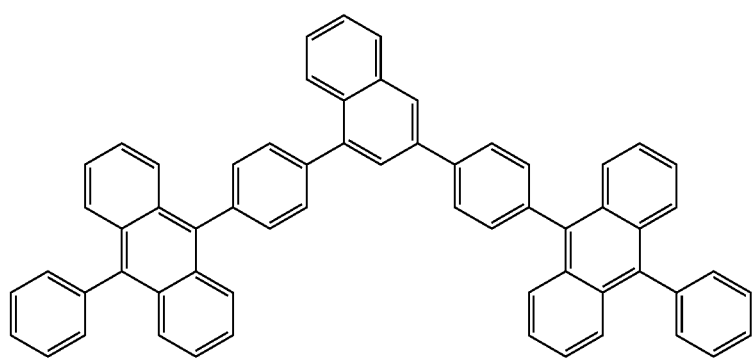

158

39-A. Preparation of Compound 39a

Under $N_2$ atmosphere, 1,3-dibromonaphthalene (5 g, 17.5 mmol), 4-bromophenylboronic acid (7.03 g, 35 mmol), and Pd(PPh$_3$)$_4$ (1.0 g, 0.88 mmol) were added to a 2 M aqueous solution of potassium carbonate (10 mL) and THF (200 mL). The mixture was refluxed under stirring for about 12 hours. After completing the reaction, the mixture was cooled to normal temperature. The organic layer was separated from the reaction mixture, dried over magnesium sulfate, and distilled under reduced pressure. The residue was purified by column chromatography to prepare a compound 39a (3.8 g, 50%). MS [M+H]+=438

39-B. Preparation of Compound 158

Under $N_2$ atmosphere, a compound 39a (1.2 g, 2.8 mmol) prepared in 39-A, 10-phenyl anthracene-9-boronic acid (3.8 g, 6.1 mmol), and Pd(PPh$_3$)$_4$ (0.16 g, 0.14 mmol) were added to a 2 M aqueous solution of potassium carbonate (20 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 158 (1.5 g, 70%). MS [M+H]+=784

EXAMPLE 40

Preparation of Compound 159

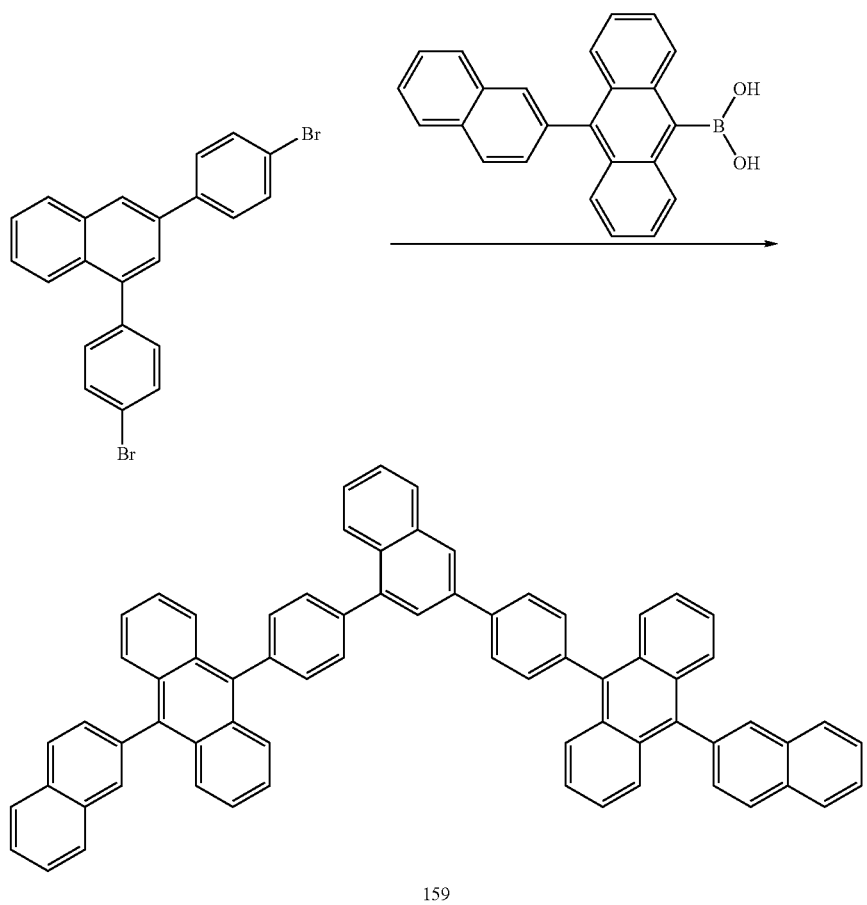

Under $N_2$ atmosphere, a compound 39a (2.28 g, 5.2 mmol) prepared in 39-A of Example 39, 10-(2-naphthyl)anthracene-9-boronic acid (4.0 g, 11.4 mmol), and $Pd(PPh_3)_4$ (0.3 g, 0.26 mmol) were added to a 2 M aqueous solution of potassium carbonate (80 mL) and anisole (100 mL). The mixture was refluxed under stirring for about 24 hours. After completing the reaction, the mixture was cooled to normal temperature. The organic layer was separated from the reaction mixture, filtered to obtain a solid. The solid was recrystallized from THF and EtOH to prepare a compound 159 (2.5 g, 66%). MS [M+H]+=884

EXAMPLE 41

Preparation of Compound 170

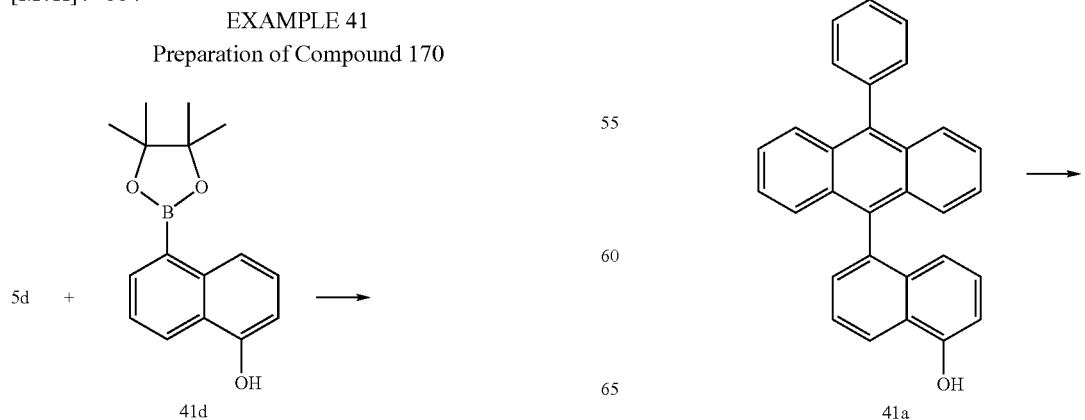

-continued

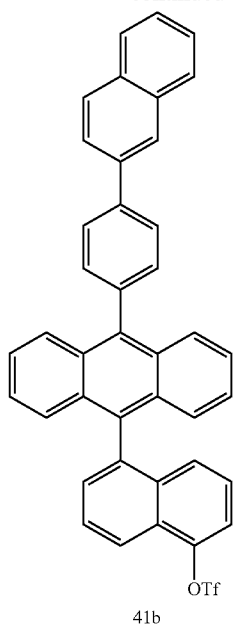

41b

-continued

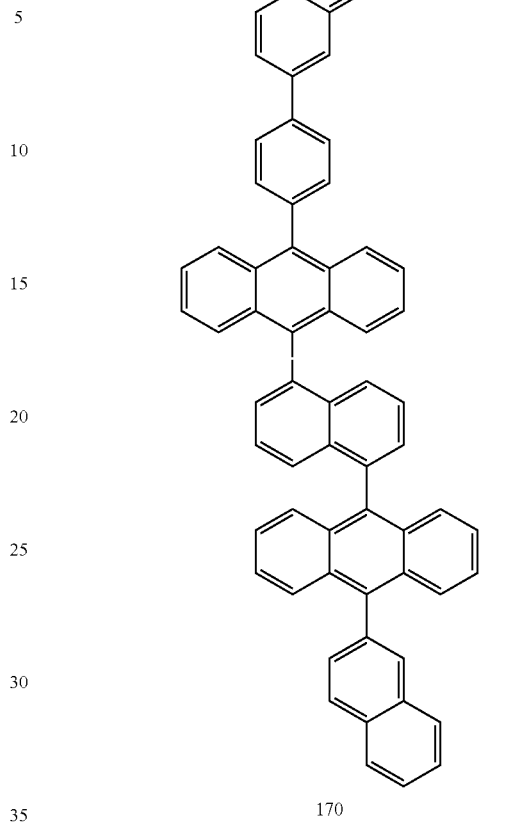

170

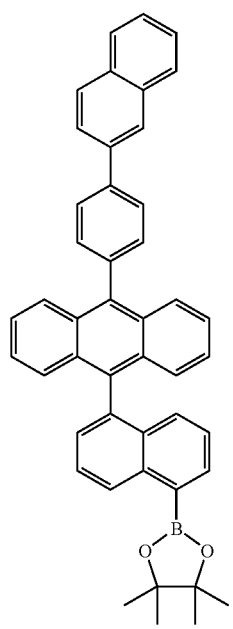

41c

41-A. Preparation of Compound 41a

Under N₂ atmosphere, a compound 5d (32 g, 70 mmol) prepared in 5-D of Example 5, 41d (18.9 g, 70 mmol), and Pd(PPh₃)₄ (4.0 g, 3.5 mmol) were added to a 2 M aqueous solution of potassium carbonate (200 mL) and THF (300 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare a compound 41a (29.3 g, 80%). MS [M]=522

41-B. Preparation of Compound 41b

Under N₂ atmosphere, a compound 41a (26.1 g, 50 mmol) prepared in 41-A and Et₃N (6.1 g, 60 mmol) were dissolved in MC (200 ml) and cooled to 0° C. Trifluoromethane sulfonic anhydride (16.9 g, 60 mmol) was slowly added thereto. The mixture was stirred at ambient temperature for 2 hours and washed with 1 N—HCl.

The organic layer was separated, dried over magnesium sulfate, and distilled under reduced pressure. The residue was purified by column chromatography to prepare a compound 41b (26.1 g, 80%). MS [M]=654

41-C. Preparation of Compound 41c

Under N$_2$ atmosphere, a compound 41b (6.5 g, 10 mmol) prepared in 41-B, pinacol diboron (3.0 g, 12 mmol), and KOAc (2.94 g, 30 mmol), 1,4-dioxane (100 ml) were mixed together and then heated at 50° C. PdCl$_2$(dppf) (4.0 g, 3.5 mmol) was added thereto and refluxed under stirring for about 24 hours. After completing the reaction, the mixture was cooled to normal temperature. Water (100 ml) and MC (100 ml) was added thereto. The organic layer was separated, dried over magnesium sulfate, and distilled under reduced pressure. The residue was purified by column chromatography to prepare a compound 41c (5.7 g, 90%). MS [M]=632

41-D. Preparation of Compound 170

Under N$_2$ atmosphere, 41c (3.2 g, 5 mmol), 10-(2-naphthyl)-9-bromo anthracene (2.3 g, 6 mmol), and Pd(PPh$_3$)$_4$ (0.17 g, 0.15 mmol) were added to a 2 M aqueous solution of potassium carbonate (20 mL) and THF (50 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare a compound 170 (2.8 g, 70%). MS [M]=809

Example 42

Preparation of Compound 171

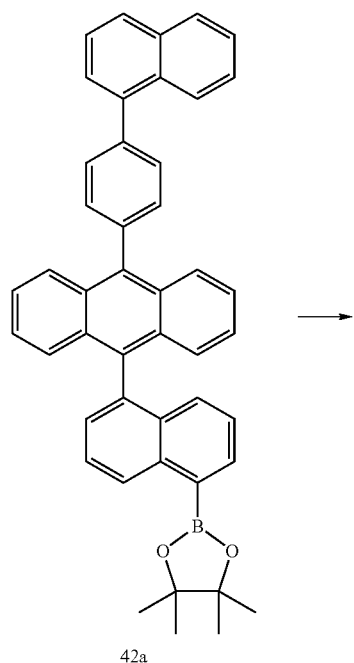

42a

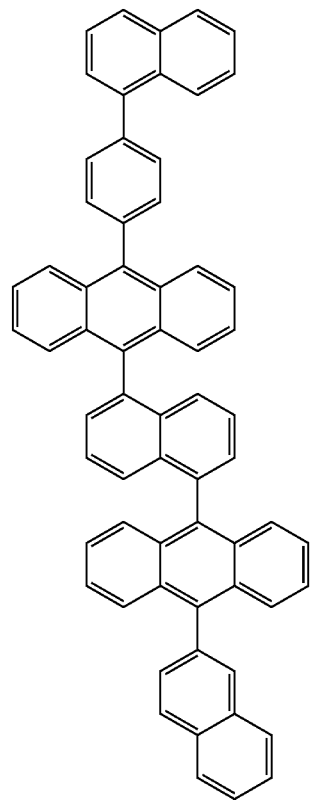

171

Under N$_2$ atmosphere, 42a (3.2 g, 5 mmol), 10-(2-naphthyl)-9-bromo anthracene (2.3 g, 6 mmol), and Pd(PPh$_3$)$_4$ (0.17 g, 0.15 mmol) were added to a 2 M aqueous solution of potassium carbonate (20 mL) and THF (50 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare a compound 171 (2.8 g, 70%). MS [M]=809

Example 43

Preparation of Compound 174

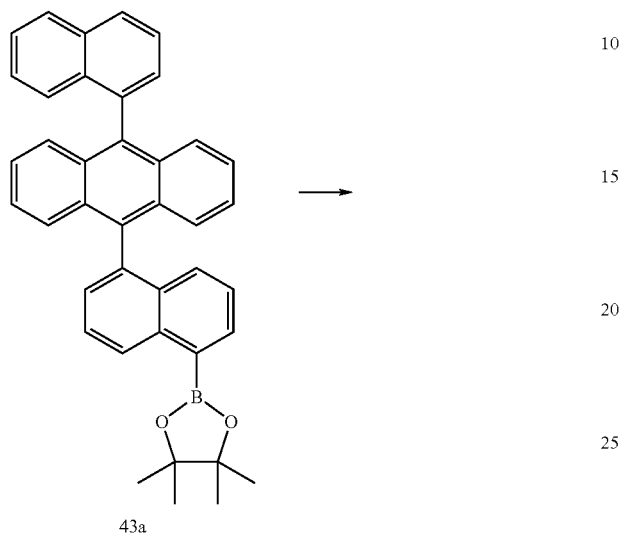

43a

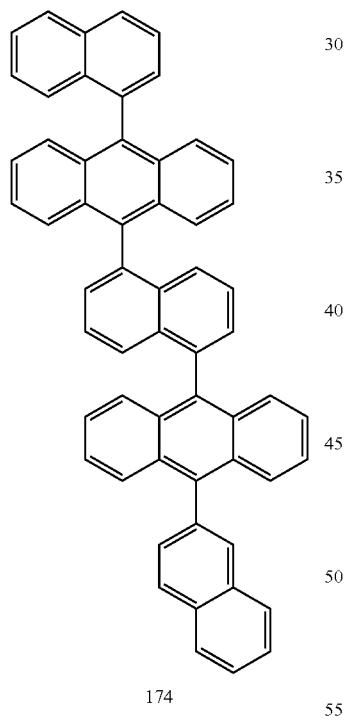

174

Under N₂ atmosphere, 43a (2.8 g, 5 mmol), 10-(2-naphthyl)-9-bromo anthracene (2.3 g, 6 mmol), and Pd(PPh₃)₄ (0.17 g, 0.15 mmol) were added to a 2 M aqueous solution of potassium carbonate (20 mL) and THF (50 mL). The mixture was refluxed under stirring for about 24 hours. After completing the reaction, the mixture was cooled to normal temperature. The organic layer was separated from the reaction mixture, dried over magnesium sulfate, and distilled under reduced pressure. The residue was purified by column chromatography to prepare a compound 174 (2.6 g, 70%). MS [M]=809

Example 44

Preparation of Compound 228

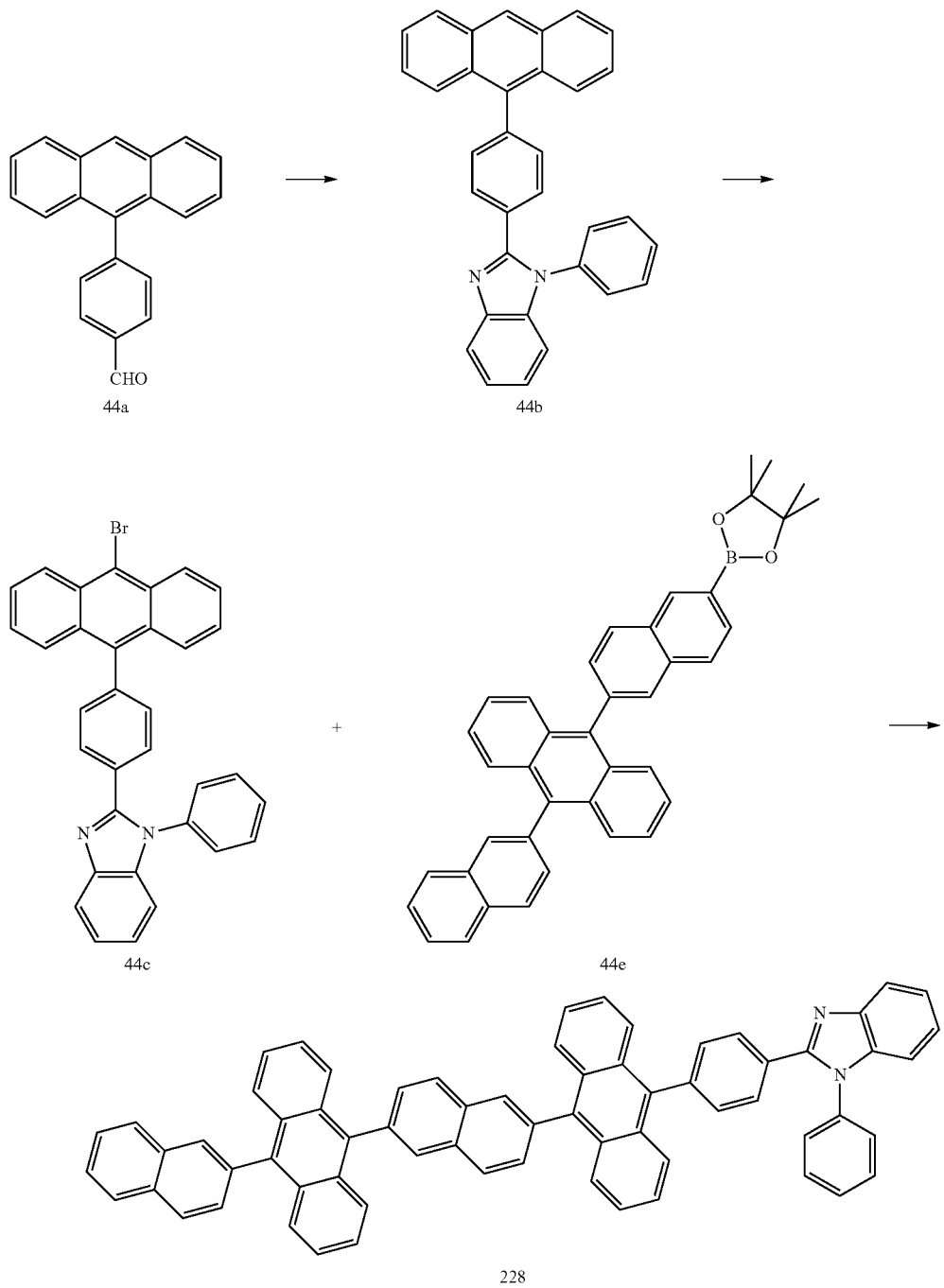

44-A. Preparation of Compound 44a 9-bromoanthracene (10 g, 38.9 mmol) and 3-formylbenzeneboronic acid (5.6 g, 46.7 mmol) was dissolved in tetrahydrofuran (100 mL). A 2 M aqueous solution of potassium carbonate and tetra bistriphenylphosphino palladium (900 mg, 0.78 mmol) was added thereto and heated under stirring for 5 hours. The mixture was cooled to normal temperature and the aqueous layer was removed. The resultant was dried over anhydrous magnesium sulfate, concentrated under reduced pressure and recrystallized from petrol ether to prepare a compound 44a (9 g, 82%). MS [M+H]$^+$=283

44-B. Preparation of Compound 44b

A compound 44a (9 g, 31.9 mmol) prepared in 44-A and N-phenyl-1,2-diamino benzene (5.87 g, 31.9 mmol) were added in dimethylacetamide (DMAC, 50 mL) and heated under stirring for 24 hours. The mixture was cooled to normal temperature and precipitated in distilled water. The precipitated was filtered and purified by column chromatography using tetrahydrofuran:hexane=1:6 to prepare a compound 44b (5 g, 36%). MS: [M+H]$^+$=447

44-C. Preparation of Compound 44c

A compound 44b (5 g, 11.2 mmol) prepared in 44-B was added to dimethylformaldehyde (DMF, 50 mL) and stirred for 30 minutes. N-bromosuccinimide (NBS, 2 g, 11.2 mmol) was slowly added thereto and stirred for 3 hours. The solid was filtered to prepare compound 44c (5.1 g, 87%). MS [M+H]$^+$=525

44-D. Preparation of Compound 228

A compound 44e (4.5 g, 8.0 mmol) and a compound 44c (3.5 g, 6.7 mmol) of 44-C were completely dissolved in tetrahydrofuran (100 mL). 2M potassium carbonate and tetrabistriphenyl phosphino palladium (155 mg, 0.013 mmol) was added thereto and heated under stirring for 5 hours. The mixture was cooled to normal temperature and the aqueous layer was removed. The resultant was dried over anhydrous magnesium sulfate, concentrated under reduced pressure and purified by column chromatography using tetrahydrofuran: hexane=1:6 to prepare a compound 228 (2.7 g, 78%). MS: [M+H]$^+$=875

Example 45

Preparation of Compound 229

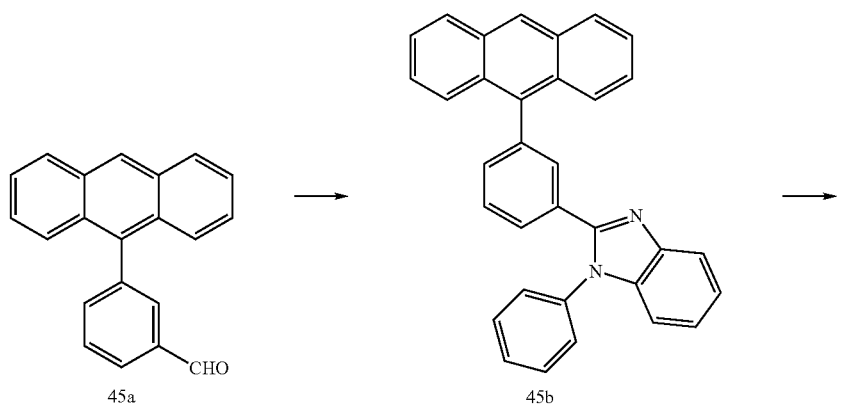

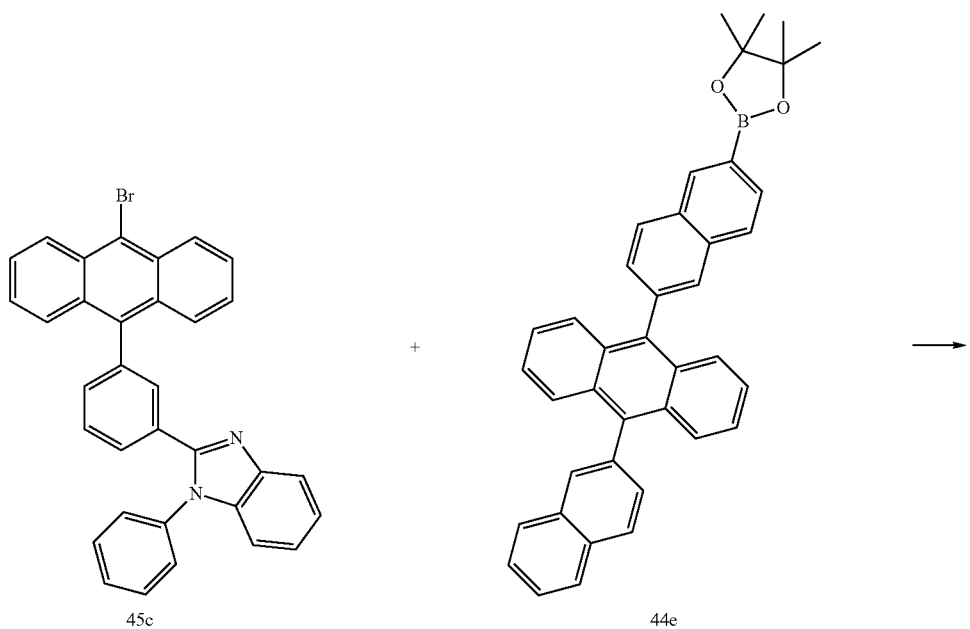

-continued

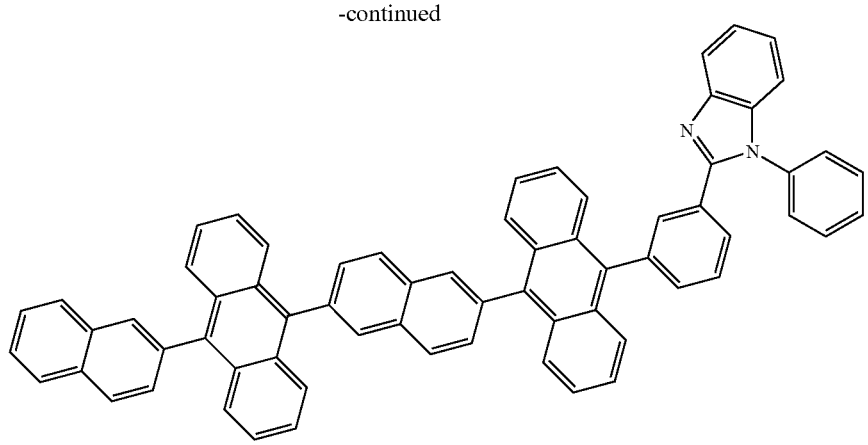

229

45-A. Preparation of Compound 45a 9-bromoanthracene (10 g, 38.9 mmol) and 3-formylbenzeneboronic acid (5.6 g, 46.7 mmol) were completely dissolved in tetrahydrofuran (100 mL). A 2 M aqueous solution of potassium carbonate and tetrabistriphenyl phosphino palladium (900 mg, 0.78 mmol) was added thereto, and heated under stirring for 5 hours. The mixture was cooled to normal temperature and the aqueous layer was removed. The resultant was dried over anhydrous magnesium sulfate, concentrated under reduced pressure and recrystallized from petrol ether to prepare a compound 45a (7.2 g, 66%). MS: $[M+H]^+=283$ 45-B. Preparation of Compound 45b A compound 45a (7.2 g, 25.5 mmol) prepared in Example 45-A and N-phenyl-1,2-diamino benzene (4.69 g, 25.5 mmol) were added in dimethylacetamide (DMAC, 50 mL) and heated under stirring for 24 hours. The mixture was cooled to normal temperature and precipitated in distilled water. The precipitated was filtered and purified by column chromatography using tetrahydrofuran:hexane=1:6 to prepare a compound 45b (4.3 g, 38%). MS: $[M+H]^+=447$ 45-C. Preparation of Compound 45c A compound 45b (4.3 g, 9.63 mmol) prepared in Example 45-B was added to dimethylformaldehyde (DMF, 50 mL) and stirred for 30 minutes. And then N-bromosuccinimide (NBS, 1.72 g, 11.2 mmol) was slowly added, and stirred for 3 hours. The solid was filtered to prepare a compound 45c (3.1 g, 61%). MS: $[M+H]^+=526$ 45-D. Preparation of Compound 229

A compound 44d (2.25 g, 4.0 mmol) and a compound 45c (1.75 g, 3.35 mmol) prepared in Example 45-C were completely dissolved in tetrahydrofuran (50 mL). A 2 M aqueous solution of potassium carbonate and tetrakis(triphenylphosphino)palladium (78 mg, 0.007 mmol) were added thereto and heated under stirring for 5 hours. The mixture was cooled to normal temperature and precipitated in distilled water. The mixture was cooled to normal temperature and the aqueous layer was removed. The resultant was dried over anhydrous magnesium sulfate, concentrated under reduced pressure and purified by column chromatography using tetrahydrofuran:hexane=1:6 to prepare a compound 229 (1.7 g, 98%). MS: $[M+H]^+=875$

EXPERIMENTAL EXAMPLE 1

A glass substrate on which a thin film of ITO (indium tin oxide) was coated to a thickness of 1000 Å was immersed in distilled water having a detergent dissolved therein to wash the substrate with ultrasonic waves. At this time, the detergent was a product commercially available from Fisher Co. and the distilled water was distilled water that had been twice filtered by using a filter commercially available from Millipore. Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried.

On the ITO transparent electrode thus prepared, 3,6-bis-2-naphthylphenylamino-N-[4-(2-naphthylphenyl)amino phenyl]carbazole (800 Å), 4,4'-bis[N-(1-naphthyl)-N-phenylamino]biphenyl(NPB) (300 Å), a host material (300 Å) of the following Table 2, and 9,10-bis-2-naphthyl-2-[4-(N-phenylbenzoimidazoyl)phenyl]anthracene (300 Å) was sequentially coated by thermal vacuum deposition to form a hole injecting layer, a hole transporting layer, a light emitting layer, an electron transporting layer in this order. An amine compound (D3, D4) was used as a dopant material of the light emitting layer.

Lithium fluoride (LiF) and aluminum were sequentially deposited on the electron transporting layer to thicknesses of 12 Å and 2000 Å respectively, to form a cathode and to prepare an organic light emitting device.

In the above process, the deposition rate of the organic material was maintained at 0.4 to 0.7 Å/sec and the deposition rate of lithium fluoride was maintained at 0.3 Å/sec and the deposition rate of aluminum was maintained at 2 Å/sec in cathode, respectively. The degree of vacuum upon deposition was maintained at $2\times10^{-7}$ to $5\times10^{-8}$ torr.

(D3)

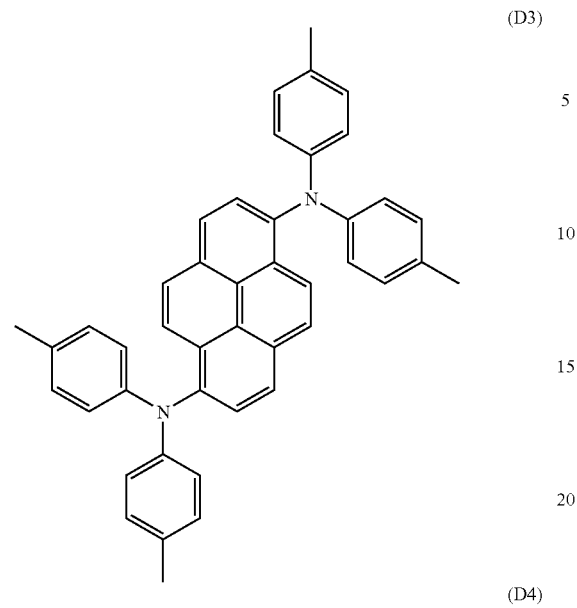

(D4)

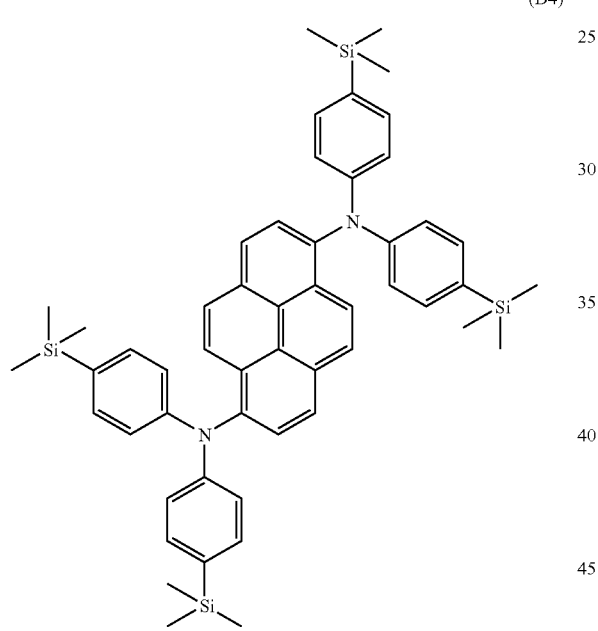

When an electric current was applied to the device thus prepared, the result followed by table 2 was obtained.

TABLE 2

| Experimental Example No. | Host material | Dopant material | Doping conc. (wt %) | Voltage (V) | Current efficiency (cd/A) | Luminous efficiency (1 m/W) | Color coordinate(x, y) |
|---|---|---|---|---|---|---|---|
| 1-1 | Compound 1 | D4 | 4 | 8.7 | 6.8 | 1.9 | (0.154, 0.181) |
| 1-2 | Compound 2 | D3 | 4 | 8.4 | 8.7 | 3.2 | (0.137, 0.283) |
| 1-3 | Compound 2 | D4 | 4 | 8.6 | 7.3 | 2.6 | (0.134, 0.171) |
| 1-4 | Compound 18 | D3 | 4 | 8.6 | 9.3 | 3.4 | (0.151, 0.330) |
| 1-5 | Compound 34 | D3 | 4 | 8.4 | 8.4 | 3.2 | (0.153, 0.315) |
| 1-6 | Compound 110 | D4 | 4 | 8.7 | 7.0 | 2.5 | (0.135, 0.188) |
| 1-7 | Compound 111 | D3 | 4 | 8.6 | 7.4 | 2.7 | (0.179, 0.273) |
| 1-8 | Compound 118 | D4 | 4 | 8.3 | 7.3 | 2.7 | (0.144, 0.188) |
| 1-9 | Compound 119 | D4 | 4 | 8.7 | 5.2 | 1.9 | (0.136, 0.199) |
| 1-10 | Comparative Compound 1 | D4 | 4 | 8.9 | 5.7 | 2.1 | (0.160, 0.246) |

[Comparative compound 1]

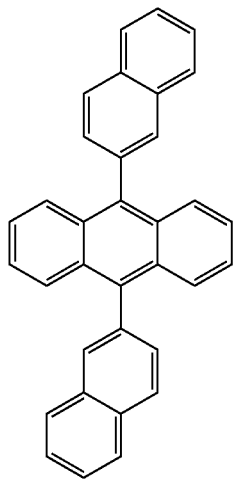

The values shown in Table 2 was measured at a current density of 100 mA/cm².

The invention claimed is:

1. An anthracene derivative represented by the following formula 1:

[Formula 1]

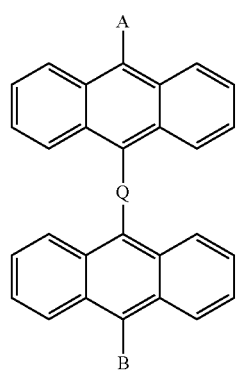

wherein A and B may be the same as or different from each other, and are each a phenyl or a naphthyl group, and Q is a group of the following structural formula:

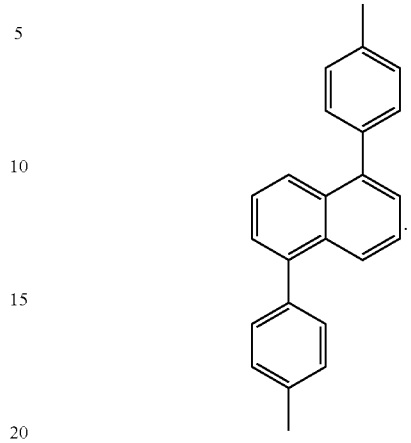

2. A method for preparing the anthracene derivative according to claim 1, wherein the anthracene derivative is prepared by subjecting a dibromoaryl compound and an anthracene boronic acid compound to a Suzuki coupling reaction in the presence of a Pd catalyst.

3. The anthracene derivative according to claim 1, wherein the compound of the formula 1 is selected from the group consisting of the following structural formulae:

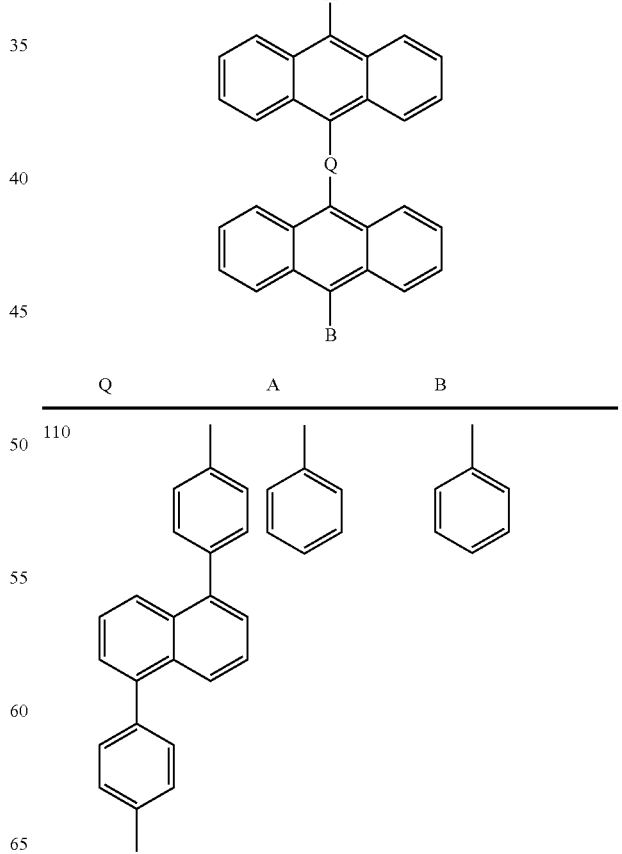

217
-continued

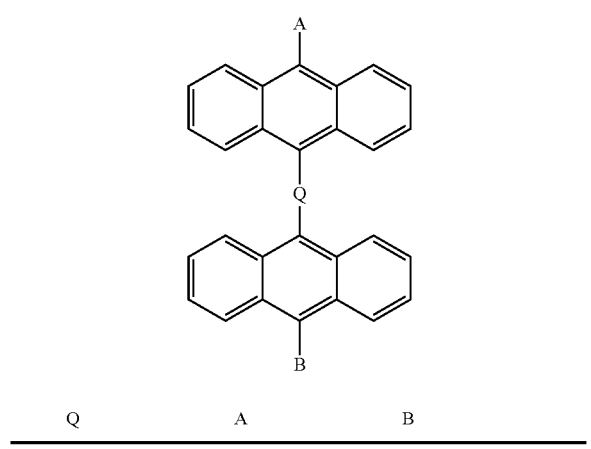

| Q | A | B |
|---|---|---|
111

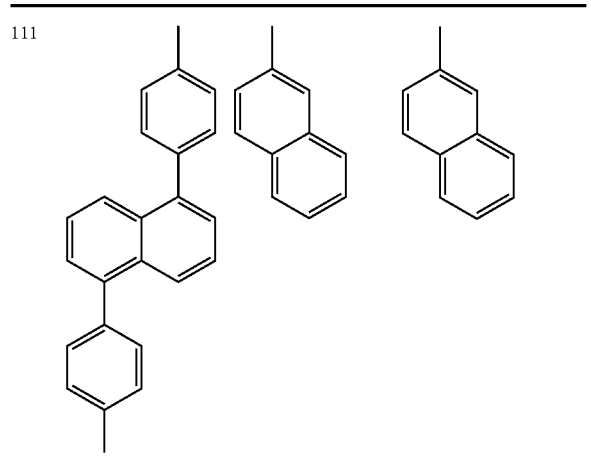

112

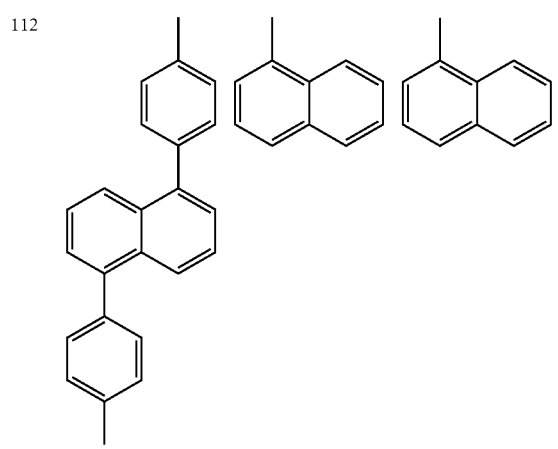

218
-continued

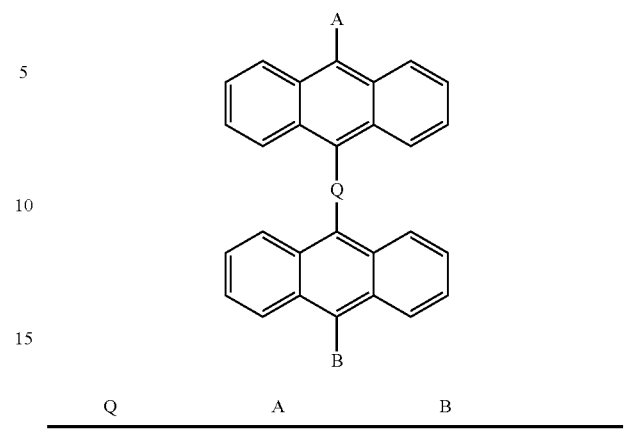

| Q | A | B |
|---|---|---|

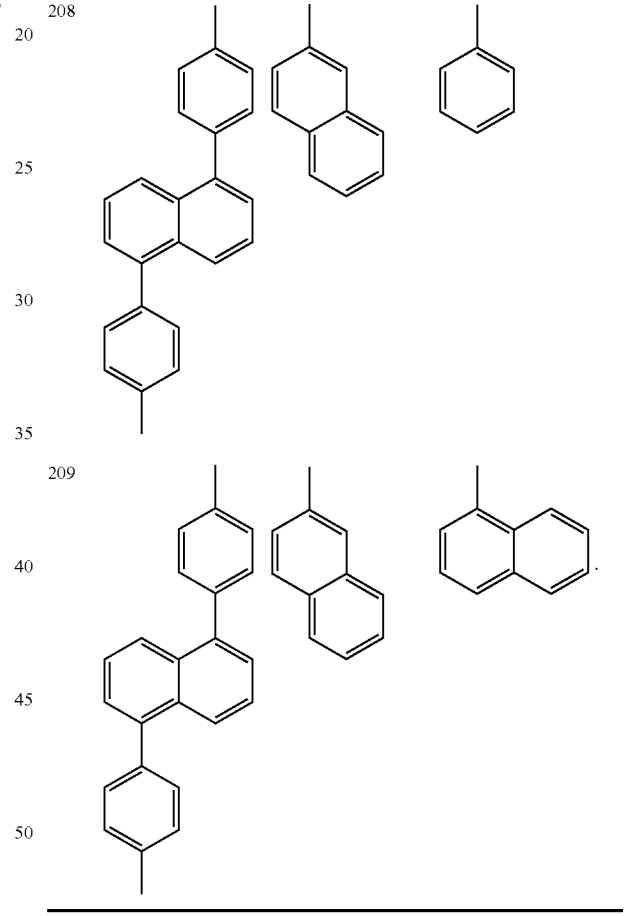

4. An organic electronic device comprising a first electrode, a second electrode, and organic material layers interposed therebetween, wherein at least one layer of the organic material layers comprises the anthracene derivative according to claim 3.

5. An organic electronic device comprising a first electrode, a second electrode, and organic material layers interposed therebetween, wherein at least one layer of the organic material layers comprises the anthracene derivative according to claim 1.

6. The organic electronic device according to claim 5, wherein the organic material layer comprises a hole injecting layer and a hole transporting layer, and the hole injecting layer and the hole transporting layer comprise the anthracene derivative.

7. The organic electronic device according to claim 5, wherein the organic material layer comprises a light emitting layer, and the light emitting layer comprises the anthracene derivative.

8. The organic electronic device according to claim 5, wherein the organic material layer comprises an electron transporting layer, and the electron transporting layer comprises the anthracene derivative.

9. The organic electronic device according to claim 5, wherein the organic electronic device is selected from the group consisting of an organic light emitting device, an organic photovoltaic cell, an organic photoconductor (OPC) and an organic transistor.

* * * * *